US010125401B2

(12) United States Patent
Audonnet et al.

(10) Patent No.: US 10,125,401 B2
(45) Date of Patent: Nov. 13, 2018

(54) HIGH RESOLUTION MELT GENOTYPING OF IBV, CSFV AND NDV

(71) Applicants: MERIAL LIMITED, Duluth, GA (US); Asia-Pacific Special Nutrients Sdn. Bhd., Selangor (MY)

(72) Inventors: Jean-Christophe Audonnet, Lyons (FR); Seetha Jaganathan, Kuala Lumpur (MY)

(73) Assignee: ASIA-PACIFIC SPECIAL NUTRIENTS SDN. BHD. (MY)

( * ) Notice: Subject to any disclaimer, the term of this patent is extended or adjusted under 35 U.S.C. 154(b) by 0 days.

(21) Appl. No.: 14/109,104

(22) Filed: Dec. 17, 2013

(65) Prior Publication Data

US 2014/0178860 A1    Jun. 26, 2014

Related U.S. Application Data

(60) Provisional application No. 61/738,688, filed on Dec. 18, 2012.

(51) Int. Cl.
    *C12Q 1/70*    (2006.01)
(52) U.S. Cl.
    CPC .............. *C12Q 1/70* (2013.01); *C12Q 1/701* (2013.01)
(58) Field of Classification Search
    None
    See application file for complete search history.

(56) References Cited

U.S. PATENT DOCUMENTS

| | | | | |
|---|---|---|---|---|
| 5,654,144 A * | 8/1997 | Mann | ...................... | C12Q 1/689 204/456 |
| 7,387,887 B2 | 6/2008 | Wittwer et al. | | |
| 7,582,429 B2 | 9/2009 | Wittwer et al. | | |
| 2002/0160357 A1 | 10/2002 | Jackwood et al. | | |
| 2003/0104395 A1 * | 6/2003 | McLaughlin | .......... | C12Q 1/686 435/6.16 |
| 2009/0191538 A1 * | 7/2009 | Donegan et al. | .................. | 435/5 |
| 2010/0112557 A1 | 5/2010 | Tobler | | |
| 2011/0097353 A1 | 4/2011 | Sellers et al. | | |

FOREIGN PATENT DOCUMENTS

| | | |
|---|---|---|
| WO | WO 2008/052742 | 5/2008 |
| WO | WO2010/017440 | 2/2010 |

OTHER PUBLICATIONS

Antal M, Farkas T, Germán P, Belák S, Kiss I. Real-time reverse transcription-polymerase chain reaction detection of Newcastle disease virus using light upon extension fluorogenic primers. J Vet Diagn Invest. Jul. 2007; 19(4):400-4.*
Fuller CM, Brodd L, Irvine RM, Alexander DJ, Aldous EW. Development of an L gene real-time reverse-transcription PCR assay for the detection of avian paramyxovirus type 1 RNA in clinical samples. Arch Virol. Jun. 2010; 155(6):817-23. Epub Mar. 16, 2010.*
Gadberry MD, Malcomber ST, Doust AN, Kellogg EA. Primaclade—a flexible tool to find conserved PCR primers across multiple species. Bioinformatics. Apr. 1, 2005; 21(7):1263-4. Epub Nov. 11, 2004.*
Hines NL, Killian ML, Pedersen JC, Reising MM, Mosos NA, Mathieu-Benson C, Miller CL. An rRT-PCR assay to detect the matrix gene of a broad range of avian paramyxovirus serotype-1 strains. Avian Dis. Jun. 2012; 56(2):387-95. Erratum in: Avian Dis. Mar. 2014; 58(1):194.*
Liu WQ, Tian MX, Wang YP, Zhao Y, Zou NL, Zhao FF, Cao SJ, Wen XT, Liu P, Huang Y. The different expression of immune-related cytokine genes in response to velogenic and lentogenic Newcastle disease viruses infection in chicken peripheral blood. Mol Biol Rep. Apr. 2012; 39(4):3611-8. Epub Jul. 5, 2011.*
Nidzworski D, Rabalski L, Gromadzka B. Detection and differentiation of virulent and avirulent strains of Newcastle disease virus by real-time PCR. J Virol Methods. Apr. 2011; 173(1):144-9. Epub Dec. 28, 2010.*
Pham HM, Konnai S, Usui T, Chang KS, Murata S, Mase M, Ohashi K, Onuma M. Rapid detection and differentiation of Newcastle disease virus by real-time PCR with melting-curve analysis. Arch Virol. Dec. 2005; 150(12):2429-38. Epub Aug. 1, 2005.*
Steyer A, Rojs OZ, Krapez U, Slavec B, Barlic-Maganja D. A diagnostic method based on MGB probes for rapid detection and simultaneous differentiation between virulent and vaccine strains of avian paramyxovirus type 1. J Virol Methods. Jun. 2010; 166(1-2):28-36. Epub Feb. 17, 2010.*
Tong S, Chern SW, Li Y, Pallansch MA, Anderson LJ. Sensitive and broadly reactive reverse transcription-PCR assays to detect novel paramyxoviruses. J Clin Microbiol. Aug. 2008; 46(8):2652-8. Epub Jun. 25, 2008.*
Zheng L, Gibbs MJ, Rodoni BC. Quantitative PCR measurements of the effects of introducing inosines into primers provides guidelines for improved degenerate primer design. J Virol Methods. Nov. 2008; 153(2):97-103. Epub Sep. 17, 2008.*
Ciammaruconi A, Grassi S, Faggioni G, De Santis R, Pittiglio V, D'Amelio R, Vergnaud G, Lista F. A rapid allele variant discrimination method for Yersinia pestis strains based on high-resolution melting curve analysis. Diagn Microbiol Infect Dis. Sep. 2009; 65(1):7-13.*
Gundry CN, Vandersteen JG, Reed GH, Pryor RJ, Chen J, Wittwer CT. Amplicon melting analysis with labeled primers: a closed-tube method for differentiating homozygotes and heterozygotes. Clin Chem. Mar. 2003; 49(3):396-406.*
Reed GH, Kent JO, Wittwer CT. High-resolution DNA melting analysis for simple and efficient molecular diagnostics. Pharmacogenomics. Jun. 2007; 8(6):597-608.*

(Continued)

*Primary Examiner* — Samuel C Woolwine
*Assistant Examiner* — Olayinka A Oyeyemi
(74) *Attorney, Agent, or Firm* — Judy Jarecki-Black; Richard Seeger; Merial Inc.

(57) ABSTRACT

The present invention relates to methods of differentiating and characterizing IBV, CSFV and NDV strains, and identifying new strains using high resolution melt technology. The present invention also provides primers and kits for use with such methods.

5 Claims, 27 Drawing Sheets

Specification includes a Sequence Listing.

(56) References Cited

OTHER PUBLICATIONS

Tong SY, Giffard PM. Microbiological applications of high-resolution melting analysis. J Clin Microbiol. Nov. 2012; 50(11):3418-21. Epub Aug. 8, 2012.*
Wittwer CT, Reed GH, Gundry CN, Vandersteen JG, Pryor RJ. High-resolution genotyping by amplicon melting analysis using LCGreen. Clin Chem. Jun. 2003; 49(6 Pt 1):853-60.*
Utagawa E, Hara M, Takahashi K, Watanabe M, Wakita T. Development of a rapid high-throughput method for high-resolution melting analysis for routine detection and genotyping of noroviruses. J Clin Microbiol. Feb. 2009; 47(2):435-40. Epub Dec. 10, 2008.*
Vossen RH, Aten E, Roos A, den Dunnen JT. High-resolution melting analysis (HRMA): more than just sequence variant screening. Hum Mutat. Jun. 2009; 30(6):860-6.*
Poh et al. 2011. Detection of Enteroviruse from clinical specimens. Diagnostic Virology Protocols, methods in Molecular Biology. vol. 665. Springer Science and Business Media, pp. 65-77.*
Mitchell SL, Wolff BJ, Thacker WL, Ciembor PG, Gregory CR, Everett KD, Ritchie BW, Winchell JM. Genotyping of Chlamydophila psittaci by real-time PCR and high-resolution melt analysis. J Clin Microbiol. Jan. 2009; 47(1):175-81. Epub Nov. 12, 2008. (Year: 2009).*
Papin JF, Vahrson W, Larson L, Dittmer DP. Genome-wide real-time PCR for West Nile virus reduces the false-negative rate and facilitates new strain discovery. J Virol Methods. Oct. 2010; 169(1):103-11. Epub Jul. 14, 2010. (Year: 2010).*
Robertson T, Bibby S, O'Rourke D, Belfiore T, Lambie H, Noormohammadi AH. Characterization of Chlamydiaceae species using PCR and high resolution melt curve analysis of the 16S rRNA gene. J Appl Microbiol. Dec. 1, 2009; 107(6):2017-28. (Year: 2009).*
Steer PA, Kirkpatrick NC, O'Rourke D, Noormohammadi AH. Classification of fowl adenovirus serotypes by use of high-resolution melting-curve analysis of the hexon gene region. J Clin Microbiol. Feb. 2009; 47(2):311-21. Epub Nov. 26, 2008. (Year: 2009).*
Wolff BJ, Thacker WL, Schwartz SB, Winchell JM. Detection of macrolide resistance in Mycoplasma pneumoniae by real-time PCR and high-resolution melt analysis. Antimicrob Agents Chemother. Oct. 2008; 52(10):3542-9. Epub Jul. 21, 2008. (Year: 2008).*
Choi et al., Antigenic and immunogenic investigation of the virulence motif of the Newcastle disease virus fusion protein, J. Vet. Sci. 11(3), 205-211,2010.
Chou et al., A Comparison of High-Resolution Melting Analysis with Denaturing High-Performance Liquid Chromatography for Mutation Scanning, Am J Clin Pathol, 124:330-338, 2005.
De wit et al., Infectious bronchitis virus variants a review of the history, current situation and control measures, Avian Pathology 40(3), 223-235, 2011.
Dolz et al., Antigenic and molecular characterization of isolates of the Italy 02 infectious bronchitis virus genotype, Avian Path 35(2), 77-85, 2006.
Dong et al., Marker vaccine strategies and candidates csfv marker vaccines, Vaccine 25, 205-230, 2007.
Ducatez et al., Characterzation of a new genotype and serotype of infectious bronchitis virus in Western Africa, J Gen Virol 90, 2679-2685, 2009.
Farkas et al., Real-Time PCR-Based Pathotyping of Newcastle Disease Virus by Use of TaqMan Minor Groove Binder Probes, J Clin Mirobiol 47(7):2114-2123, 2009.
Geerligs et al., Efficacy and safety of an attenuated live QX-like infectious bronchitis virus strain as a vaccine for chicken, Avian Path 40(1), 93-102, 2011.
Ghorashi et al., Differentiation of Mycoplasma gallisepticum strains using PCR and high-resolution melting curve analysis, Microbiology 156, 1019-1029, 2010.
Hewson et al., Rapid detection and non-subjective characterisation of infectious bronchitis virus isolates using high-resolution melt curve analysis and a mathematical model, Arch Virol 154:649-660, 2009.
Hewson et al., Application of high-resolution melt curve analysis for classifcation of infectious bronchitis viruses in field specimens, Aust vet J., 88(10), 408-413, 2010.
Hoffmann et al., Validation of a real time RT PCR assay for sensitive and specific detection of classical swine fever, J Virol M, 130, 36-44, 2005.
Huang et al., Development of a RT multipex RT PCR for the detection and genotyping of classical swine feber virus, J Virol Methods 160, 111-118, 2009.
Ignjatovic et al., Isolation of a variant infectious bronchitis virus in Australia that further illustrates diversity among emerging strains, Arch Virol, 151:1567-1585, 2006.
Ishikawa et al., High-resolution melting curve analysis for MEDAKA analysis, BMC Molecular Biology 11:70, 2010.
Ivanyi, Classical swine fever: new control and eradication methods, Rev. sci. tech. Off. int. Epiz. 3(3), 465-486, 1984.
Jackwood, The relationship of severe acute respiratory syndrome coronavirus with avian and other coronaviruses, Avian Dis 50:315-320, 2006.
Jia et al., A novel variant of avian infectious bronchitis virus resulting from recombination among three different strains, Arch Virol 140:259-271, 1995.
Jindal et al., Phylogenetic analysis of newcastle disease viruses isolated from waterfowl in the Upper Midwest regions of the US, J Virol 6:191, 2009.
Krape et al., Molecular analysis of infectious bronchitis viruses isolated in Slovenia between 1990 and 2005: a retrospective study, Virus Genes 41:414-416, 2010.
Kumar et al., Experimental avian paramyxovirus serotype-3 infection in chickens and turkeys, Vet. Res. 41:72, 2010.
Kusters et al., Phylogeny of antigenic coronavirus IBV, Virology 169, 217-221, 1989.
Larussa et al., Restriction fragment length polymorphism of polymerase chain reaction products from vaccine and wild-type varicella-zoster virus isolates, J Virol 66(2), p. 1016-1020, 1992.
Leifer et al., Molecular epidemiology of current classical swine fever virus isolates of wild board in Germany, J Gen Virol 91, 2687-2697, 2010.
Leifer et al., Escape of classical swine fever C-strain vaccine virus from detection by C-strain specific real-time RT-PCR caused by a point mutation in the primer-binding site, J Virol Methds 166, 98-100, 2010.
Li et al., A multiplex nested RT PCR for the detection and differentiation of wild type viruses from C strain vaccine of classical swine fever virus, J Virol M 143, 16-22, 2007.
Liu et al., A new genotype of nephopathogenic infectious bronchitis virus circulating in vaccinated and non vaccinated flocks in China, Avian Pathology 33(3), 321-327, 2004.
Liu et al., Complete genome sequence analysis of a predominant IBV strain in China, Virus Genes 38:56-65, 2009.
Liu et al., Genetic diversity of avian infectious bronchitis coronavirus strains isolated in China between 1995 and 2004, Arch Virol 151:1133-1148, 2006.
Liu et al., Isolation of avian infectious bronchitis coronavirus from domestic peafowl (Pavo cristatus) and teal (Anas), J Gen Virol 86, 719-725, 2005.
Liu et al., Molecular charac and pathogenicity of infectious bronchitis Coronaviruses: complicated evolution and epidemiology in China caused by cocirculation of multiple types of infectious bronchitis coronaviruses, Intervirology 52:223-234, 2009.
Liu et al., Two real time PCR assays of classical swine fevere virus, developed for the genetic differentiation of naturaly infected from vaccinated wild boars, J Virol M 159, 131-133, 2009.
Lohr, Serologic Differences btween strains of IBV from New Zealand, Australia, and the United States, Avian Diseases 20(3), 478-482, 1976.
Loparev et al., Improved indentification and differentiation of Varicella-Zoster Virus (VZV) wild-type strains and an attenuated

(56) References Cited

OTHER PUBLICATIONS varicella vaccine strain using a VZV open reading frame 62-based PCR, J Clin Microbiol 38(9), p. 3156-3160, 2000.
Mardani et al., Naturally occurring recombination between distant strains of infectious bronchitis virus, Arch Virol 155:1581-1586, 2010.
Miller et al., Antigenic differences among Newcastle disease virus strains of different genotypes used in vaccine formulation affect viral shedding afer a virulent challenge, Vaccine 25, 7238-7246, 2007.
Miller et al., Comparison of Viral Shedding Following Vaccination with Inactivated and Live Newscatle Disease Vaccines Formulated with Wild-Type and Recombinant Viruses, Av Dis 53:39-49, 2009.
Miller et al., Evolutionary dynamics of Newcastle disease virus, Virology 391, 64-72, 2009.
Miller et al., Newcastle disease Evolution of genotypes and the related diagnostic challenges, Infection, Genetics and Evolution 10, 26-35, 2010.
Moenning et al., Clinical Signs and Epidemiology of Classical Swine Fever: A review of New Knowledge, Vet J 165, 11-20, 2003.
Moormann et al., Infectious RNA transcribed from an engineered full length cDNA template of the genome of a pestivirus, J Virol 70(2), p. 763-770, 1996.
Muradrasol et al., Prevalence and Phylogeny of Coronaviruses in Wild Birds from the Bering Strait Area (Beringia), Plos One 5(10), e13640, 2010.
Ovchinnikova et al., Molecular characterization of infectious bronchitis virus isolates from Russia and neighbouring countries: identification of intertypic recombination in the S1 gene, Avian Path 40(5), 507-514, 2011.
Pan et al., Rapid detection and differentiation of wild-type and three attenuated lapinized vaccine strains of classical swine fever virus by reverse transcription polymerase chain reaction, J Vet Diagn Invest 20:448-456, 2008.
Parchariyanon et al., Genetic grouping of classical swine fever virus by restriction fragment length polymorphism of the E2 gene, J Virol Methods 87, 145-149, 2000.
Parker et al., Genotyping of varicella-zoster virus and the discrimination of Oka vaccine strain by TaqMan real-time PCR, J Clin Mirobiol 44(11), p. 3911-3914, 2006 Paton et al., Classical swine fever virus: a ring test to evaluate RT PCR detection methods, Vet Microbiol 73, 159-174, 2000.
Perez et al., Development and validation of novel SYBR green RTPCR assay for the detection of CSFV on different real time PCR platforms, J Virol M 174, 53-59, 2011.
Pohuang et al., Detection and molecular characterization of IBV isolated from recent outbreaks in broiler flocks in Thailand, J Vet Sci 10(3), 219-223, 2009.
Postel et al., Improved strategy for phylogenetic analysis of CSFV based on full ength E2 encoding sequences, Vet Res 43:50, 2012.
Ravindra et al., Newscatle disease virus as an oncolytic agent, Indian J Med Res 130, pp. 507-513, 2009.
Reed et al., High-resolution DNA melting analysisfor simple and efficient molecular diagnostics, Pharmacogenomics 8(6), 597-608, 2007 2007.
Schweiger et al., Differentiation of vaccine and wild type poliovirus using PCR and restriction enzyme analysis, Arch Virol 134:39-50, 1994.
Si et al., A multiplex reverse transcription-nested polymerase chain reaction for detection and differentiation of wild-type and vaccine strains of canine distemper virus, J Virol 7:86, 2010.
Steer et al., Classification of Fowl Adenovirus Serotypes by Use of HRM Curve Analysis of the Hexon Gene Region, J clin Microbiol 47(2), p. 311-321, 2009.
Sun et al., Phylogenetic analysis of IB coronaviruses newly isolated in China, and pathogenicity and evaluation of protection induced by Massachusetts serotype H120 vaccine against QX-like strains, Avian Path 40(1), 43-54, 2011.
Susta et al., Pathogenicity evaluation of different NDV chimeras in 4-week-old chickens, Trop Animal Health 2010.

Tan et al., Detection and differentiation of velogenic and lentogenic NDV by SYBR green I real-time PCR with nucleocapsid gene-specific primers, J Vet Med 160, 149-156, 2009.
Tan et al., Sequence and phylogenetic analysis of NDV genotypes isolated in Malaysia between 2004 and 2005, Arch Virol 155:63-70, 2010.
Terregino et al., Pathgenicity of a QX strain of infectious bronchitis virus in specific pathogen free and commercial broiler chickens, and evaluation of protection induced by a vaccination programme based on the Ma5 and 4/91 serotypes, Avian Path 37(5), 487-493, 2008.
Tignon, et al., Development and inter laboratory validaiton study of an improved new qPCR assay with interna control for detection of african swine fever virus, J Virol M 178, 161-170, 2011.
Toi et al., Differentiation between vaccine and wild type varicella-zoster virus genotypes by HRM analysis on single nucleotide polymorphisms, J Clin Virol 43, 18-24, 2008.
Tu et al., Phylogenetic comparison of CSFV in China, Virus Res 81, 29-37, 2001.
Tumpey et al., Diagnostic approach for differentiating inf3ected from vaccinated poultry on the basis of antibodies to NS1, the nonstructural protein of influenza A virus, J Clin Microbiol 43(2), p. 676-683, 2005.
Van Gennip et al., Determinants of virulence of CSFV strain brescia, J Virol 78(16), p. 8812-8823, 2004.
Van Oirschot, Vaccinology of CSF from lab to field, Vet Microbiol 96, 367-384, 2003.
Vossen et al., High-resolution melting analysis (HRMA)—more than just sequence variant screening, Human Mutation 30(6), 860-866, 2009.
Wang et al., Isolation and Identification of IBV from Chickens in Sichuan, China, Avian Diseases 41:279-282, 1997.
Weiss et al., Coronavirus Pathogenesis and the Emerging Pathogen Severe Acute Respiratory Syndrome Coronavirus, Microbiol. Mol. Biol. Rev 69(4), p. 635-664, 2005.
Wen et al., Evaluation of a real time RT PCR assay using minor groove binding probe for the detection of Chinese wild type CSFV, J Virol M 176, 96-102, 2011.
Wise et al., Development of a Real Time RT PCR for detection of NDV RNA in Clinical Samples, J. Clin. Microbiol. 42(1), 329-338, 2004.
Worthington et al., A RT PCR survey of IBV genotypes in Western Europe from 2002 to 2006, Avian Path 37(3), 247-257, 2008.
Wu et al., Development and valiation of a prokaryotically expressed foot-and-mouth disease virus non-structural protein 2C'3AB-based Immunochromatographic strip to differentiate between infected and vaccinated animals, Virology Journal 8:186, 2011.
Xu et al., Development of a multiplex PCR for simultaneous detection of 6 swine DNA and RNA viruses, J Virol Methods 183, 69-74, 2012.
Ye at al., Sensitivity and specificity of HRM analysis in screening unknown SNPs and genotyping a known mutation, Animal Science 28(2), 161-170, 2010.
Zhou et al., High-Resolution DNA melting analysis for simultaneous mutation scanning and genotyping in solution, Clinical Chem 51:10, 1770-1777, 2005.
Zulperi et al., Sequence and phylogenetic analysis of S1, S2, M and N genes of IBV isolates from Malaysia, Virus Genes 38:383-391, 2009.
Adi et al. Isolation and Chracterization of a pathogenic Newcastle disease virus from a natural case in Indonesia, J. Vet. Med. Sci. 72(3):313-319, 2010.
Adzhar et al., Universal oligonucleotides for the detection of infectious bronchitis virus by polymerase chain reaction, Avian Pathology, 25:817-836, 1996.
Aldous et al. Detection and differentiation of newcastle disease virus (avian paramyxovirus type 1), Avian Pathology 30, 117-128,2011.
Avellaneda et al., Differentiation of infected and vaccinated animals (DIVA) using the NS1 proein of avian influenza virus, Avian Disease 54:278-286, 2010.
Baaske et al. Melting curve analysis in a snap shot, App Physics Letters 91, 133901, 2007.

(56) References Cited

OTHER PUBLICATIONS

Bayry et al. Emergence of a Nephropathogenic Avian Infectious Bronchitis Virus with a Novel Genotype in India, J Clin Mirbiol, 43(2), p. 916-918, 2005.

Berhanu et al., Molecular characterization of partial fusion gene and C-terminus extension length of haemagglutinin-neuraminidase gene of recently isolated Newcastle disease virus isolates in Malaysia, Virol J., 7:183, 2010.

Blome et al. Genetic differentiation of infected from vaccinated animals after implementation of an emergency vaccination strategy against classical swine fever in wild boar, Vet Microbiol 153, 373-376, 2011.

Bochkov et al., Molecular epizootiology of avian infctious bronchitis in Russia,Avian Pathology, 35(2):379-393, 2006.

Bochkov et al. Phylogenetic analysis of partial S1 and N gene sequences of infectious bronchitis virus isolates from Italy revealed genetic diversity and recombination, Virus Genes 35:65-71, 2007.

Bricker, PCR as a diagnostic tool for brucellosis, Vet Microbiol 90, 435-446, 2002.

Cavanagh et al Sequence analysis of strains of avian infectious bronchitis coronavirus isolated during the 1960s in the UK, Arch Virol 130:471-476,1992.

Cavanagh et al., Longitudinal field studies of infectious bronchitis virus and avian pneumovirus in boilers using type-specific polymerase chain reactions, Avian Pathology , 28, 593-605,1999.

Cho et al., High-Resolution Melting Curve Analysis of Genomic and Whole-Genome Amplified DNA, Clinical chemistry 54:12, 2008.

Cho et al., Development of a reverse-transcription polymerase chain reaction assay with fluorogenic probes to discriminate Korean wild-type and vaccine isolates of classical swine fever virus, Can J Vet Res, 70:226-229, 2006.

Jackwood MW et al., "Detection of infecriour bronchitis virus by real-time reverse transcriptase-polymerase chain reaction and identification of a quasispecies in the beaudette strain", Avian Diseases, 2003, vol. 47, No. 3, pp. 718-724.

Hyuk Moo Kwon et al., "Molecular cloning and sequence comparison of the S1 glycoprotein of the gray and JMK strains of avian infectious bronchitis virus", Virus Genes, 1995, vol. 99, No. 3, pp. 2192-2129.

\* cited by examiner

Figure 1A

| SEQ ID NO | Type | Description |
|---|---|---|
| 1 | primer | XCE2-ª primer for IBV |
| 2 | primer | XCE2-ᵇ primer for IBV |
| 3 | primer | XCE3- primer for IBV |
| 4 | primer | BCE1+ primer for IBV |
| 5 | primer | DCE1+ primer for IBV |
| 6 | primer | MCE1+ primer for IBV |
| 7 | DNA | S1 sequence of IB-QX strain amplified by PCR |
| 8 | primer | Forward primer for CSFV |
| 9 | primer | Reverse primer for CSFV |
| 10 | DNA | Sequence of PCR product of CSFV of LBK |
| 11 | DNA | Sequence of PCR product of CSFV of VRI |
| 12 | DNA | Sequence of PCR product of CSFV of Pestiffa |
| 13 | DNA | Sequence of PCR product of CSFV of MVP |
| 14 | DNA | Sequence of PCR product of CSFV of QYHC |
| 15 | DNA | Sequence of PCR product of CSFV of ZBC |
| 16 | DNA | Sequence of PCR product of CSFV of YSC |
| 17 | primer | Forward primer 1 for NDV |
| 18 | primer | Reverse primer 1 for NDV |
| 19 | DNA | NDV strain clone30 (Genbank Accession No. Y18898) |
| 20 | DNA | NDV strain Mukteswar (Genbank Accession No. JF950509) |
| 21 | DNA | NDV strainB1 (Genbank Accession No. AF309418) |
| 22 | DNA | NDV strain VG/GA (Genbank Accession No. EU289028) |
| 23 | DNA | NDV strain KBNP-C4152R2L (Genbank Accession No. EU140955) |
| 24 | protein | NDV strain clone30 (Genbank Accession No. CAB51325.1 |
| 25 | protein | NDV strain Mukteswar (Genbank Accession No. AEL75038) |
| 26 | protein | NDV strain B1 (Genbank Accession No. AAG36978.1) |
| 27 | protein | NDV strain VG/GA (Genbank Accession No. ABZ80389.1) |
| 28 | protein | NDV strain KBNP (Genbank Accession No. ABV60359.1) |
| 29 | Primer | Forward primer for IB-QX for IBV |
| 30 | Primer | Reverse primer for IB-QX for IBV |
| 31 | Primer | Forward primer 2 for NDV |
| 32 | Primer | Reverse primer 2 for NDV |
| 33 | peptide | F fusion of NDV cleavage site motif 1 |
| 34 | peptide | F fusion of NDV cleavage site motif 2 |
| 35 | peptide | F fusion of NDV cleavage site motif 3 |
| 36 | DNA | M5365 (Genbank Accession No. FJ518780.1) |
| 37 | DNA | V9/04 (Genbank Accession No. FJ518779.1) |
| 38 | DNA | THA50151 (Genbank Accession No. GQ503613.1) |
| 39 | DNA | THA40151(Genbank Accession No. GQ503612.1) |
| 40 | DNA | THA20151(Genbank Accession No. GQ503610.1) |

Figure 1B

| SEQ ID NO | Type | Description |
|---|---|---|
| 41 | DNA | THA90151(Genbank Accession No. GQ503617.1) |
| 42 | DNA | THA60151(Genbank Accession No. GQ503614.1) |
| 43 | DNA | AF193423 (Genbank Accession No. AF193423.1) |
| 44 | DNA | AY043312 (Genbank Accession No. AY043312.1) |
| 45 | protein | F fusion cleavage motif 4 |
| 46 | protein | F fusion cleavage motif 5 |

Sensitivity of real-time PCR assay for IBV

Amplification Curve – IB-QX (Specificity)

Melting peak (Tm) - IB-QX (Specificity)

Figure 5

SEQ ID NO:7 (S1 sequence of IB-QX strain)

```
1   GTTCTGCACAAGGGTGCACTGTTGGTGTTATTAAGGATGTTTATAATCAAAGTGTGGCTTCCATAGCTATGACAGCACCT  80
81  CTTCAGGGTATGGCTTGGTCTAAGGCACAATTCTGTAGTGCACACTGTAACTTTTCTGAAATTACAGTTTTTGTCACACA  160
161 TTTGTTATAGTAGTGGTAGTG  180
```

BLAST results

| Accession Number | Description | Max Score | Total Score | Query coverage | E-value | Max identity |
|---|---|---|---|---|---|---|
| EU914939.1 | Infectious bronchitis virus isolate UK/AV2150/07 spike glycoprotein S1 gene, partial cds | 333 | 333 | 100% | 2e-88 | 100% |
| FJ807928.1 | Infectious bronchitis virus isolate K1255/03 S1 glycoprotein (S1) gene, partial cds | 327 | 327 | 100% | 1e-86 | 99% |
| FJ807927.1 | Infectious bronchitis virus isolate K1019/03 S1 glycoprotein (S1) gene, partial cds | 327 | 327 | 100% | 1e-86 | 99% |
| HM486955.1 | Infectious bronchitis virus isolate K426/08 S1 glycoprotein gene, partial cds | 322 | 322 | 100% | 5e-85 | 99% |
| EF621389.1 | Infectious bronchitis virus isolate Kr/D75/05 S1 glycoprotein, partial gene, partial cds | 322 | 322 | 100% | 5e-85 | 99% |

Figure 6

Comparison of the previously reported nepropathogenic IB (MH5365/95) with sequences in Genbank

| Accession Number | Description | Max Score | Total Score | Query coverage | E-value | Max identity |
|---|---|---|---|---|---|---|
| GQ503613.1 | Infectious bronchitis virus isolate THA50151 S1 glycoprotein (S1) gene | 2976 | 2326 | 98% | 0.0 | 93% |
| GQ503612.1 | Infectious bronchitis virus isolate THA40151 S1 glycoprotein (S1) gene | 2326 | 2326 | 98% | 0.0 | 93% |
| GQ503610.1 | Infectious bronchitis virus isolate THA20151 S1 glycoprotein (S1) gene | 2326 | 2326 | 98% | 0.0 | 93% |
| GQ503617.1 | Infectious bronchitis virus isolate THA90151 S1 glycoprotein (S1) gene | 2326 | 2320 | 98% | 0.0 | 93% |
| GQ503614.1 | Infectious bronchitis virus isolate THA60151 S1 glycoprotein (S1) gene | 2320 | 2320 | 98% | 0.0 | 93% |
| AF193423.1 | Avian infectious bronchitis virus S1 spike protein (S1) gene, partial gene | 2320 | 1936 | 100% | 0.0 | 88% |
| AY043312.1 | Avian infectious bronchits virus isolate A2 S1 protein (S1) gene | 1936 | 1925 | 100% | 0.0 | 88% |

Figure 7

| Seq-> | MH5365 | V9/04 | THA20151 | THA40151 | THA50151 | THA60151 | THA90151 | AY043312 | AF193423 |
|---|---|---|---|---|---|---|---|---|---|
| MH5365 | 100 | 80.5 | 92.8 | 92.8 | 92.8 | 92.8 | 92.8 | 88.3 | 88.7 |
| V9/04 | | 100 | 80.6 | 80.6 | 80.6 | 80.7 | 80.7 | 78.3 | 78.7 |
| THA20151 | | | 100 | 99.8 | 99.8 | 99.9 | 99.9 | 89 | 89.1 |
| THA40151 | | | | 100 | 99.7 | 99.8 | 99.8 | 88.9 | 89.1 |
| THA50151 | | | | | 100 | 99.8 | 99.8 | 89 | 89.3 |
| THA60151 | | | | | | 100 | 100 | 89 | 89.1 |
| THA90151 | | | | | | | 100 | 89 | 89.1 |
| AY043312 | | | | | | | | 100 | 98.1 |
| AF193423 | | | | | | | | | 100 |

HRM analysis to compare IB-QX, IBnC90, Mass and 793/B

HRM analysis to compare/detect IB-QX and IBnC90

Figure 10

Sequence ID: LBK (wild-type)  (SEQ ID NO:10)

```
  1   TAGCAAGACTGGGAATAGGTACATACCTGGAGAGGGCCACACCCTGCAAGGAAGACACTATGAAGAACTGGTGCTAGCAA    80
 81   GAAAGCAGGTCAACAACTTTCAAGGGACAGACAGGTATAATCTAGGTCCAATAGTCAATATGGTGCTAAGGAGGCTGAGA   160
161   GTCATGATGATGACCTTGATTGGCAGAGGGTATGAGGTGGTTAACCCGCGATCTGGACCCGCTATTAGGACTCTATTG    240
241   TAGATAACACTATTTATTTTATTTATTTACATATTACTATTTGTTTATTTATTTATTTATTGAATGAGTAAGAACTGGT   320
321   ACAAACTACCTCGTGTTACCACACTACACTCATTTTTAACAGCACTT   367
```

BLAST

| Accession Number | Description | Max Score | Total Score | Query coverage | E-value | Max identity |
|---|---|---|---|---|---|---|
| D49532.1 | Hog cholera virus (strain ALD) complete sequence, encoding a polyprotein | 538 | 538 | 100% | 1e-149 | 93% |
| AF326963.1 | Classical swine fever virus strain Eystrup, complete genome | 529 | 529 | 100% | 7e-147 | 93% |
| HM237795.1 | Classical swine fever virus strain CSFV/1.1/dp/CSF0382/XXXX/Koslov | 521 | 521 | 100% | 1e-144 | 92% |
| DQ127910.1 | Classical swine fever virus strain SWH, complete genome | 520 | 520 | 100% | 4e-144 | 92% |
| EU497410.1 | Classical swine fever virus strain J1(06), complete genome | 516 | 516 | 100% | 5e-143 | 92% |

Figure 11

Sequence of VR1 (wild-type) (SEQ ID NO:11)

```
1    TAGCAAGACTGGGAACAGGTACACCCCGGGGAAGGCCACACCCTGCAAGGAAGACACTATGAAGAACTGGTGCTAGCAA    80
81   GAAAGCAGGTCAACAACTTTCAAGGGACAGACAGGTATAATCTAGGTCCAATAGTCAATATGGTGCTAAGGAGGCTGAGA   160
161  GTCATGATGATGACCTTGATTGGGAGAGAGGGTATGAGCGTGGTTAACCCGCGATCTGGACCCGCTATTAGGACTCTATTG  240
241  TAGATAACACTATTTATTTTTATTTATTTAGATATTACTATTTGTTTATTTATTTATTTATTGAATGAGTAAGAACTGGT  320
321  ACAAACTACCTCCTGTTACCACACTACACTCATTTTTAACAGCACTT   367
```

BLAST

Sequences producing significant alignments:

| Accession Number | Description | Max Score | Total Score | Query coverage | E-value | Max identity |
|---|---|---|---|---|---|---|
| D49532.1 | Hog cholera virus (strain ALD) complete sequence, encoding a polyprotein | 510 | 510 | 100% | 2e-141 | 92% |
| AF326963.1 | Classical swine fever virus strain Eystrup, complete genome | 501 | 501 | 100% | 1e-138 | 91% |
| HM237795.1 | Classical swine fever virus strain CSFV/1.1/dp/CSF0382/XXXX/Koslov | 497 | 497 | 100% | 2e-137 | 91% |
| DQ127910.1 | Classical swine fever virus strain SWH, complete genome | 494 | 494 | 100% | 2e-136 | 91% |
| EU497410.1 | Classical swine fever virus strain J1(06), complete genome | 494 | 494 | 100% | 2e-136 | 91% |

Figure 12

Sequence of Pestiffa (SEQ ID NO:12)

```
1    GTAGCACGGGGGGGAAGGGAGACATACCCGGGGGCGAAACAGCTTGCACGCAAGACATTATGAAGAACTGGTGTTGGCA    80
81   AGAAAACACATCAACAACTTTCAAGGGACAGACAGGTACAACCTAGGCCCAATAGTCAACATGGTGTTAAGGAGGCTGAG   160
161  AGTCATGATGATGACGCTGATAGGGAGAGGGGTATGAGCGCGGGTAACCCGGGATCTGAACCCGCCAGTAGGACCCTATT   240
241  GTAGATAACACTAATTTTTTTTTTTTTTTTTTTTTTTAGATATTATTATTTATTTTTTTTTTTTTTTTAAAAAA         320
321  AAAAAAAATTTTTTAAACTACCTCAAGTTACCACATTACACTCATTTTTAGGGGGGGG   379
```

BLAST

| Accession Number | Description | Max Score | Total Score | Query coverage | E-value | Max identity |
|---|---|---|---|---|---|---|
| Z46258.1 | Hog cholera virus (Classical swine fever virus) "Chinese" strain (C-strain | 503 | 503 | 92% | 4e-139 | 93% |
| HM175885.1 | Classical swine fever virus strain C-ZJ-2008, complete genome | 496 | 496 | 92% | 7e-137 | 92% |
| AY805221.1 | Classical swine fever virus strain CC/HVRI, complete genome | 490 | 490 | 92% | 3e-135 | 92% |
| AY663656.1 | Classical swine fever virus, complete genome | 490 | 490 | 92% | 3e-135 | 92% |
| AY382481.1 | Classical swine fever virus, complete genome | 490 | 490 | 92% | 3e-135 | 92% |

Figure 13

Sequence of MVP (SEQ ID NO: 13)

```
1    TAGTTAGTACAAACACGGAAAAGGGTACACCCGGGAGGGCCCACCCCCTGCAGGGGAGACATTATGAAGAACTGGTG   80
81   TTGCCAAGAAAACAGATCAAAAACTTTCAGGGACAGACAGGTACAATCTAGGCCCAATAGTCAACATGGTGTTAAGGAG  160
161  GCTGAGAGTCATATTATTGCTCTTATTGGGGAGGGGGTATGAGCGCGGGCAACCGGGGATCTGGACCTGCCAGTAGGAC  240
241  CCTATTGTAGATAACACTAATTTTTTATTTATTTAGATATTATTATTTATTTATTTATTTATTTATTGAATGAGTAAGAA  320
321  CTGGTACAAACTACCTCAAGTTACCACACCTCCCTCCTTTTTTACAGCCCTTTTAAATGG  379
```

BLAST

| Accession Number | Description | Max Score | Total Score | Query coverage | E-value | Max identity |
|---|---|---|---|---|---|---|
| D49533.1 | Hog cholera virus (strain GPE-) complete sequence, encoding a polyprotein | 545 | 545 | 98% | 7e-152 | 93% |
| U90951.1 | Classical swine fever virus strain C-ZJ-2008, complete genome | 529 | 529 | 98% | 7e-147 | 92% |
| X87939.1 | Classical swine fever virus strain CC/HVRI, complete genome | 529 | 529 | 98% | 7e-147 | 92% |
| U45460.1 | Classical swine fever virus, complete genome | 521 | 521 | 98% | 1e-144 | 92% |
| D49532.1 | Classical swine fever virus, complete genome | 518 | 518 | 98% | 1e-143 | 92% |

Figure 14

Sequence of QYHC (SEQ ID NO: 14)

```
1    TGTAGCAAGACTGGGAATAGGTACATACCCGGAGAGGGTCACACCCTGCAAGGAAGACATTATGAAGAACTGGTGTTGGC    80
81   AAGAAAACAGATCAACAACTTTCAAGGGACAGACAGGTACAACCTAGGCCCAATAGTCAACATGGTGTTAAGGAGGCTGA    160
161  GAGTCATGATGATGACGCTGATAGGGAGAGGGGCATGAGCGCGGTAACCCGGGATCTGAACCCGCCAGTAGGACCCTAT    240
241  TGTAGATAACACTAATTTCTTTTTTCTTTTTATTTATTAGATATTATTATTTATTTATTTATTATTATTATGAATGAG    320
321  TAAGAACTGGTATAAACCCTCAAGTCACCACACTACACTCATTTTAACAGCACTTTA    379
```

BLAST

| Accession Number | Description | Max Score | Total Score | Query coverage | E-value | Max identity |
|---|---|---|---|---|---|---|
| AY805221.1 | Classical swine fever virus strain C/HVRI, complete genome | 678 | 678 | 99% | 0.0 | 99% |
| AY663656.1 | Classical swine fever virus, complete genome | 678 | 678 | 99% | 0.0 | 99% |
| AY382481.1 | Classical swine fever virus, complete genome | 678 | 678 | 99% | 0.0 | 99% |
| AF531433.1 | Classical swine fever virus strain HCV, complete genome | 678 | 678 | 99% | 0.0 | 99% |
| HM175885.1 | Classical swine fever virus strain, C-ZJ-2008, complete genome | 673 | 673 | 99% | 0.0 | 99% |

Figure 15

Sequence of ZBC (SEQ ID NO: 15)

```
1    TGTAGCAAGACTGGGAATAGGTACATCCCGGGGAAGGTCACAACATGCAAGGAAGACATTATGAAGAACTGGTGTTGGC    80
81   AAGAAAACAGATCAACAACTTTCAAGGGACAGACAGGTACAACCTAGGCCCAATAGTCAACATGTGTGTTAAGGAGGCTGA   160
161  GAGTCATGATGATGACGCTGATAGGGAGAGGGGCATGAGCGCGGGTAACCCGGGATCTGAACCCGCCAGTAGGACCCTAT   240
241  TGTAGATAACACTAATTTTCTTTTTCTTTTTTATTTATTTAGATATTATTATTTATTTATTTAFTTAFTTAFTGAATGA    320
321  GTAAGAACTGGTATAAACACCTCAAGACCACACTACACTCATTTTTAACAGCACTTTAA   379
```

BLAST

| Accession Number | Description | Max Score | Total Score | Query coverage | E-value | Max identity |
|---|---|---|---|---|---|---|
| AY805221.1 | Classical swine fever virus strain C/HVRI, complete genome | 649 | 649 | 99% | 0.0 | 98% |
| AY663656.1 | Classical swine fever virus, complete genome | 649 | 649 | 99% | 0.0 | 98% |
| AY382481.1 | Classical swine fever virus, complete genome | 649 | 649 | 99% | 0.0 | 98% |
| AF531433.1 | Classical swine fever virus strain HCV, complete genome | 649 | 649 | 99% | 0.0 | 98% |
| HM175885.1 | Classical swine fever virus strain, C-ZJ-2008, complete genome | 645 | 645 | 99% | 0.0 | 97% |

Figure 16

Sequence of YSC (SEQ ID NO: 16)

```
  1   GGGGCCCCCCTGGAAAAGTTAAACTCTCACGAGACATTCAATGAAGAACTGGTGTTGGCAAGAAAACAGATCAACAACT    80
 81   TTCAAGGGACAGACAGGTACAACCTACGCCCAATAGTCAACATGGTGTTAAGGAGGCTGAGAGTCATGATGATGACGCTG   160
161   ATAGGGAGAGGGCATGAGCGCGGGTAACCGGGATCTGAACCCGCCAGTAGGACCCTATTGTAGACAACACTAATCTCT    240
241   TTTTTTTTTTTTTTTTTTTTTTTTTTTTTTTTTTTAGATATTTTTTTTTTTTTTTTTTTTTTTTTTTTAAAAAAGCAA    320
321   AAACTGGTATAAACCCCCCCCCCCCCCCCCCGTTTTTTTTTAAAAAAACTTTAGC                             379
```

BLAST

| Accession Number | Description | Max Score | Total Score | Query coverage | E-value | Max identity |
|---|---|---|---|---|---|---|
| U45456.1 | Hog cholera virus strain Riems polyprotein gene, putative NS5 protein | 455 | 455 | 82% | 1e-124 | 93% |
| AY259122.1 | Classical swine fever virus strain Riems, complete genome | 398 | 398 | 65% | 2e-107 | 96% |
| Z46258.1 | Hog cholera virus (Classical swine fever virus) "Chinese" strain (C-strain) | 385 | 385 | 63% | 2e-103 | 95% |
| HM175885.1 | Classical swine fever virus strain C-ZJ-2008, complete genome | 383 | 383 | 63% | 6e-103 | 95% |
| AY805221.1 | Classical swine fever virus strain C/HVRI, complete genome | 381 | 381 | 63% | 2e-102 | 95% |

Figure 17

Differentiation of wild-type vs. vaccine-type of CSFV

Figure 8: The HRM assay was able to differentiate and group the vaccine-type (Pestiffa) and wild-type strains (LBK/VRI).

```
                190       200       210       220       230       240
            ....|....|....|....|....|....|....|....|....|....|....|....|
wildtype    TTGGGAGAGGGGTATGAGCGTGGTTAACCGCGATCTGGACCCGCTATTAGGACTCTATT
Pestiffa    TAGGGAGAGGGGCATGAGCGCGGGTAACCCGGGATCTGAACCCGCCAGTAGGACCCTATT 250       260       270       280       290       300
            ....|....|....|....|....|....|....|....|....|....|....|....|
wildtype    GTAGATAACACTA-----------TTTATTTTATTTATTTAGATATTACTATTTGTTT
Pestiffa    GTAGATAACACTAATTTTTTTTTTTTTTTTTTTTTTTTAGATATTATTATTTATTT 310       320       330       340       350       360
            ....|....|....|....|....|....|....|....|....|....|....|....|
wildtype    ATTTATTTATTTATTGAATGAGTAAGAACTGGTACAAACTACCTCGTGTTACCACACTAC
Pestiffa    TTTTTTTTTTTTTTAAAAAAAAAAAAAAATTTTTTTAAACTACCTCAAGTTACCACACTAC
```

Note:
Wild-type (LBK):   SEQ ID NO:10
Pestiffa:          SEQ ID NO:12

Figure 18

HRM assay to differentiate different vaccine-type CSFV

Figure 19

A portion of the nucleotide sequence alignment of the wild-type (LBK) and
the vaccine-types (Pestiffa, ZBC, YSC, QYHC and MVP)

```
                190       200       210       220       230       240
           ....|....|....|....|....|....|....|....|....|....|....|....|
wt_LBK     CCTTGATTGGGAGAGGGGTATGAGCGTGGTTAACCCGCGATCTGGACCCGCTATTAGGAC
vt_Pestiffa CGCTGATAGGGAGAGGGGCATGAGCGCGGGTAACCCGGGATCTGAACCCGCCAGTAGGAC
vt_ZBC     CGCTGATAGGGAGAGGGGCATGAGCGCGGGTAACCCGGGATCTGAACCCGCCAGTAGGAC
vt_YSC     CGCTGATAGGGAGAGGGGCATGAGCGCGGGTAACCCGGGATCTGAACCCGCCAGTAGGAC
vt_QYHC    CGCTGATAGGGAGAGGGGCATGAGCGCGGGTAACCCGGGATCTGAACCCGCCAGTAGGAC
vt_MVP     CCTTATTGGGGAGGGGGTATGAGCGCGGGCAACCCGGGATCTGGACCCGCCAGTAGGAC 250       260       270       280       290       300
           ....|....|....|....|....|....|....|....|....|....|....|....|
wt_LBK     TCTATTGTAGATAACAGTATTTAT---------------------TTTTATTTAT
vt_Pestiffa CCTATTGTAGATAACACTAATTTTTTTTTTTTTTTT---------------TTTTTTTTTT
vt_ZBC     CCTATTGTAGATAACACTAATTTTCTTTTTTCTT---------------TTTTATTTAT
vt_YSC     CCTATTGTAGACAACATAATCTTTTTTTTTTTTTTTTTTTTTTTTTTTTTTTTTT
vt_QYHC    CCTATTGTAGATAACACAATTTTCTTTTTTCTT---------------TTTTATTTAT
vt_MVP     CCTATTGTAGATAACACTAATT--------------------------TTTATTTAT 310       320       330       340       350       360
           ....|....|....|....|....|....|....|....|....|....|....|....|
wt_LBK     TTAGATATTACTATTTGTTTATTTATTTATTTATTGAATGAGTAAGAACTGGTACAAACT
vt_Pestiffa TTAGATATTATTATTTATTTTTTTTTTTTTTTTAAAAAAAAAAAAAATTTTTTTAAACT
vt_ZBC     TTAGATATTATTATTTATTTATTTATTTATTTATTAATGAGTAAGAACTGGTATAAAC-
vt_YSC     TTAGATATTTTTTTTTTTTTTTTTTTTTTTTTTAAAAAAGCAAAAACTGGTATAAACC
vt_QYHC    TTAGATATTATTATTTATTTATTTATTTATTTAT-GAATGAGTAAGAACTGGTATAAAC-
vt_MVP     TTAGATATTATTATTTATTTATTTATTTATTTATTGAATGAGTAAGAACTGGCACAAACT
```

LBK: SEQ ID NO:10
Pestiffa: SEQ ID NO:12
ZBC: SEQ ID NO:15
YSC: SEQ ID NO:16
QYHC: SEQ ID NO:14
MVP: SEQ ID NO:13

Figure 20

HRM assay of NDV vaccine strains

```
                      4870       4880       4890       4900       4910       4920
                 ....|....|....|....|....|....|....|....|....|....|....|....|....|
clone30          GTCTGTGACTACATCTGGAGGGGGGAGACAGGGGCGCCTTATAGGCGCCATTATTGGCGG
Mukteswar        GTCTGTGACTACATCCGGAGGAAGGAGACAGAGACGCTTTATAGGTGCCATTATTGGCAG
VG/GA            GTCTATGACTACATCTGGAGGGGGGAGACAGGGGCGCCTTATAGGCGCCATTATTGGCGG
KBNP-C4152R2L    GTCTGTGTCCACGTCTGGAGGAGGCAGACAAGCACGCCTGATAGGTGCTGTTATTGGCAG
B1               GTCTGTGACTACATCTGGAGGGGGGAGACAGGGGCGCCTTATAGGCGCCATTATTGGCGG
``` clone30:       SEQ ID NO:19;      Mukteswar:      SEQ ID NO:20;     B1:     SEQ ID NO:21
VG/GA:         SEQ ID NO:22'      KBNP-C4152

Figure 22

```
                  10        20        30        40        50        60        70
                  ....|....|....|....|....|....|....|....|....|....|....|....|....|....|
Clone30    MGSRPSTKNPAPMMLTIRVALVLSCICPANSIDGRPLAAAGIVVTGDKAVNIYTSSQTGSIIVKLLPNLP
Mukteswar  MGPRSSTKIPVPEMLTIRTTLALSMYRLTSSDGRPLAAAGIVVTGDKAVNIYTSSQTGSIIVKLLPNLP
Avinew     MGSRPSTKNPAPMMLTIRVALVLSCICPANSIDGRPLAAAGIVVTGDKAVNIYTSSQTGSIIVKLLPNLP
KBNP       MGSKISTKIPAPIMLTTRTTLSLSCIRPTSSDGRPLAAAGIVVTGDKAVNKYTSSQTGSIIVKLLPNSP
B1         MGSRPFTKNPAPMMLTIRVALVLSCICPANSIDGEAAAGIVVTGDKAVNIYTSSQTGSIIVKLLPNLP 80        90        100       110       120       130       140
                  ....|....|....|....|....|....|....|....|....|....|....|....|....|....|
Clone30    KDKEACAKAPLDAYNRTLTTLLTPLGDSIRRIQESVTTSGGGRQGRLIGAIIGGVALGVATAAQITAAAA
Mukteswar  KDKEACAKAPLEAYNRTLTTLLTPLGDSIRRIQESVTTSGGRRQRREIGAIIGSVALGVATAAQITAASA
Avinew     KDKEACAKAPLDAYNRTLTTLLTPLGDSIRRIQESITTSGGGRQGRLIGAIIGGVALGVATAAQMAAAAA
KBNP       RDKEACAKAPLEAYNRTLTTLLTPLGDSIREIQGSVSTSGGGRQARLIGAIIGSVALGVATAAQITAAAA
B1         KDKEACAKAPLDAYNRTLTTLLTPLGDSIRRIQESVTTSGGGRQGRLIGAIIGGVALGVATAAQITAAAA 150       160       170       180       190       200       210
                  ....|....|....|....|....|....|....|....|....|....|....|....|....|....|
Clone30    LIQAKQNAANILRLKESIAATNEAVHEVTDGLSQLAVAVGKMQQFVNDQFNKTAQELDCIKIAQQVGVEL
Mukteswar  LIQANQNAANILRLKESIAATNEAVHEVTEGLSQLAVAVGKMQQFVNDQFNNTAQELDCIKITQQVGVEL
Avinew     LIQAKQNAANILRLKESIAATNEAVHEVTDGLSQLAVAVGKMQQFVNDQFNKTAQELDCIKIAQQVGVEL
KBNP       LIQANQNAANILRLKESIAATNEAVHEVTDGLSQLSVAVGKMQQFVNDQFNNTAEELDCIKITQQVGVEL
B1         LIQAKQNAANILRLKESIAATNEAVHEVTDGLSQLAVAVGKMQQFVNDQFNKTAQELDCIKIAQQVGVEL 220       230       240       250       260       270       280
                  ....|....|....|....|....|....|....|....|....|....|....|....|....|....|
Clone30    NLYLTELTTVFGPQITSPALNKLTIQALYNLAGGNMDYLLTKLGIGNNQLSSLIGSGLITGNPILYDSQT
Mukteswar  NLYLTELTTVFGPQITSPALTQLTKQALYNLAGGNKDYLLTKLGIGNNQLSSLIGSGLITGNPIFYDSQT
Avinew     NLYLTELTTVFGPQITSPALNKLTIQALYNLAGGNMDYLLTKLGIGNNQLSSLIGSGLITGNPILYDSQT
KBNP       NLYLTELTTVFGPQITSPALTKLTIQALYNLAGGNKYLLTKLGIGNNQLSSLIGSGLITGEPILYDSQT
B1         NLYLTELTTVFGPQITSPALNKLTIQALYNLAGGNMDYLLTKLGIGNNQLSSLIGSGLITGNPILYDSQT 290       300       310       320       330       340       350
                  ....|....|....|....|....|....|....|....|....|....|....|....|....|....|
Clone30    QLLGIQVTLPSVGNLNNMRATYLETLSVSTTKGFASALVPKVVTQVGSVIEELDTSYCIETDLDLYCTRI
Mukteswar  QLLGIQVTLPSVGNLNNMRATYLETLSVSTTKGFASALVPKVATQVGSVIEELDTSYCIEADLDLYCTRI
Avinew     QLLGIQVTLPSVGNLNNMRATYLETLSVSTTKGFASALVPKVVTQVGSVIEELDTSYCIETDLDLYCTRI
KBNP       QLLGIQVNLPSVGNLNNMRATYLETLSVSTTKGNASALVPKVVTQVGSVIEELDTSYCIESDLDLYCTRI
B1         QLLGIQVTLPSVGNLNNMRATYLETLSVSTTRGFASALVPKVVTQVGSVIEELDTSYCIETDLDLYCTRI 360       370       380       390       400       410       420
                  ....|....|....|....|....|....|....|....|....|....|....|....|....|....|
Clone30    VTFPMSPGIYSCLSGNTSACMYSKTEGALTTPYMTIKGSVIANCKMTTCRCVNPPGIISQNYGEAVSLID
Mukteswar  VTFPMSPGIYSCLSGNTSACMYSKTEGALTTPYMTKKGSVKANCQMTTCRCABPPGIISQNYGEAVSLID
Avinew     VTFPMSPGIYSCLSGNTSACMYSKTEGALTTPYMTIKGSVIANCKMTTCRCVNPPGIISQNYGEAVSLID
KBNP       VTFPMSPGIYSCLSGNTSACMYSKTEGALTTPYMAKKGSVIANCKTTCRCTBPPGIISQNYGEAVSLID
B1         VTFPMSPGIYSCLSGNTSACMYSKTEGALTTPYMTIKGSVIANCKMTTCRCVNPPGIISQNYGEAVSLID 430       440       450       460       470       480       490
                  ....|....|....|....|....|....|....|....|....|....|....|....|....|....|
Clone30    KQSCNVLSLGGITLRLSGEFDVTYQKNISIQDSQVIITGNLDISTELGNVNNSISNALNKLEESNRKLDK
Mukteswar  KHSCNVESLDGITLRLSGEFDATYQKNISIEDSQVITGNLDISTELGNVNESISNALEKLEESNSKLDK
Avinew     KQSCNVLSLGGITLRLSGEFDVTYQKNISIQDSQVIITGNLDISTELGNVNNSISNALNKLEESNRKLDK
KBNP       RHSCNVLSLDGITLRLSGEFDATYQKNISIEDSQVITGNLDISTELGNVNNSISNALSSLAESNSKLEK
B1         KQSCNVLSLGGITLRLSGEFDVTYQKNISIQDSQVIITGNLDISTELGNVNNSISNALNKLEESNRKLDK 500       510       520       530       540       550
                  ....|....|....|....|....|....|....|....|....|....|....|....|....
Clone30    VNVKLTSTSALITYIVLTIISLVFGILSLILACYLMYKQKAQQKTLLWLGNNTLDQMRATTKM
Mukteswar  VNVELTSTSALITYIVLTEISLVLGESLSLELACYLMYKQKAQEKTLLWLGNNTLDQMRATTKM
Avinew     VNVKLTSTSALITYIVLTIISLVFGILSLILACYLMYKQKAQQKTLLWLGNNTLDQMRATTKM
KBNP       BNVELTSTSALITYIVLTEISLVFGAFSLGLACYLMYKQKAQQKTLLWLGNNTLDQMRATTEM
B1         VNVKLTSTSALITYIVLTIISLVFGILSLILACYLMYKQKAQQKTLLWLGNNTLDQMRATTKM
``` clone30: SEQ ID NO:24;   Mukteswar: SEQ ID NO:25;   B1: SEQ ID NO:26
VG/GA: SEQ ID NO:27'   KBNP-C4152R2L: SEQ ID NO:28;

Figure 23A Sequence identity matrix of the whole genome of the vaccine-type NDV

| Seq-> | clone30 | Mukteswar | Avinew | KBNP-C4152R2L | B1 |
|---|---|---|---|---|---|
| Clone30 |  | 87.6 | 99 | 95.5 | 98.9 |
| Mukteswar |  |  | 87.7 | 86.9 | 87.6 |
| Avinew |  |  |  | 94.9 | 99.5 |
| KBNP-C4152R2L |  |  |  |  | 94.8 |
| B1 |  |  |  |  |  |

Figure 23B Sequence identity matrix of the amino acid residues for the fusion protein gene of the vaccine-type NDV

| Seq-> | Clone 30 | Mukteswar | Avinew | KBNP-C4152R2L | B1 |
|---|---|---|---|---|---|
| Clone 30 |  | 89.80 | 99.00 | 89.10 | 99.20 |
| Mukteswar |  |  | 88.90 | 90.00 | 89.00 |
| Avinew |  |  |  | 88.60 | 99.00 |
| KBNP-C4152R2L |  |  |  |  | 88.70 |
| B1 |  |  |  |  |  |

Figure 24

Samples were compared with Merial Vaccine (Avinew/Lasota). The wild-type (▲) and vaccine type (◆) is distinguished by the distinct melting curves.

Figure 25

Samples were compared with known vvNDV (velogenic) obtained from PDC. The velogenic/mesogenic (●) and lentogenic (▲◆) is distinguished by the distinct melting curves.

SEQUENCE LISTING

<160> NUMBER OF SEQ ID NOS: 46

<210> SEQ ID NO 1
<211> LENGTH: 19
<212> TYPE: DNA
<213> ORGANISM: artificial sequence
<220> FEATURE:
<223> OTHER INFORMATION: XCE2-a primer

<400> SEQUENCE: 1
ctctataaac acccttaca                                        19

<210> SEQ ID NO 2
<211> LENGTH: 21
<212> TYPE: DNA
<213> ORGANISM: artificial sequence
<220> FEATURE:
<223> OTHER INFORMATION: XCE2-b primer

<400> SEQUENCE: 2
cactggtaat ttttcagatg g                                     21

<210> SEQ ID NO 3
<211> LENGTH: 19
<212> TYPE: DNA
<213> ORGANISM: artificial sequence
<220> FEATURE:
<223> OTHER INFORMATION: XCE3 primer

<400> SEQUENCE: 3
cagattgctt acaaccacc                                        19

<210> SEQ ID NO 4
<211> LENGTH: 21
<212> TYPE: DNA
<213> ORGANISM: artificial sequence
<220> FEATURE:
<223> OTHER INFORMATION: BCE1 primer

<400> SEQUENCE: 4
agtagttttg tgtataaacc a                                     21

<210> SEQ ID NO 5
<211> LENGTH: 21
<212> TYPE: DNA
<213> ORGANISM: artificial sequence
<220> FEATURE:
<223> OTHER INFORMATION: DCE1 primer

<400> SEQUENCE: 5
atacaattat atcaaaccag c                                     21

<210> SEQ ID NO 6
<211> LENGTH: 21
<212> TYPE: DNA
<213> ORGANISM: artificial sequence
<220> FEATURE:
<223> OTHER INFORMATION: MCE1 primer

<400> SEQUENCE: 6
aatactactt ttacgttaca c                                     21

<210> SEQ ID NO 7
<211> LENGTH: 180
<212> TYPE: DNA
<213> ORGANISM: artificial sequence
<220> FEATURE:
<223> OTHER INFORMATION: S1 DNA of IB-QX strain

<400> SEQUENCE: 7
gttctgcaca agggtgcact gttggtgtta ttaaggatgt ttataatcaa agtgtggctt        60
ccatagctat gacagcacct cttcagggta tggcttggtc taaggcacaa ttctgtagtg       120
cacactgtaa cttttctgaa attacagttt ttgtcacaca ttgttatagt agtggtagtg       180

<210> SEQ ID NO 8
<211> LENGTH: 22
<212> TYPE: DNA
<213> ORGANISM: artificial sequence
<220> FEATURE:
<223> OTHER INFORMATION: forward primer for CSFV
<220> FEATURE:
<221> NAME/KEY: misc_feature
<222> LOCATION: (14)..(14)
<223> OTHER INFORMATION: r is A or G
<220> FEATURE:
<221> NAME/KEY: misc_feature
<222> LOCATION: (17)..(17)
<223> OTHER INFORMATION: Y is C or T

<400> SEQUENCE: 8
gtagcaagac tggraayagg ta                                                22

<210> SEQ ID NO 9
<211> LENGTH: 22
<212> TYPE: DNA
<213> ORGANISM: artificial sequence
<220> FEATURE:
<223> OTHER INFORMATION: reverse primer for CSFV

<400> SEQUENCE: 9
aaagtgctgt taaaaatgag tg                                                22

<210> SEQ ID NO 10
<211> LENGTH: 367
<212> TYPE: DNA
<213> ORGANISM: artificial sequence
<220> FEATURE:
<223> OTHER INFORMATION: DNA of CSFV of LBK

<400> SEQUENCE: 10
tagcaagact gggaataggt acatacctgg agagggccac accctgcaag gaagacacta        60
tgaagaactg gtgctagcaa gaaagcaggt caacaacttt caagggacag acaggtataa       120
tctaggtcca atagtcaata tggtgctaag gaggctgaga gtcatgatga tgaccttgat       180
tgggagaggg gtatgagcgt ggttaacccg cgatctggac ccgctattag gactctattg       240 tagataaacac tatttatttt tatttattta gatattacta tttgtttatt tatttattta      300
ttgaatgagt aagaactggt acaaactacc tcgtgttacc acactacact catttttaac       360
agcactt                                                                 367

<210> SEQ ID NO 11
<211> LENGTH: 367
<212> TYPE: DNA
<213> ORGANISM: artificial sequence
<220> FEATURE:
<223> OTHER INFORMATION: PCR product of CSFV of VRI

<400> SEQUENCE: 11
tagcaagact gggaacaggt acaccccggg ggaaggccac accctgcaag gaagacacta        60

```
tgaagaactg gtgctagcaa gaaagcaggt caacaacttt caagggacag acaggtataa    120
tctaggtcca atagtcaata tggtgctaag gaggctgaga gtcatgatga tgaccttgat    180
tgggagaggg gtatgagcgt ggttaacccg cgatctggac ccgctattag gactctattg    240
tagataacac tatttatttt tatttattta gatattacta tttgtttatt tatttattta    300
ttgaatgagt aagaactggt acaaactacc tcgtgttacc acactacact cattttaac    360 agcactt                                                              367
```

<210> SEQ ID NO 12
<211> LENGTH: 379
<212> TYPE: DNA
<213> ORGANISM: artificial sequence
<220> FEATURE:
<223> OTHER INFORMATION: PCR product of CSFV of Pestiffa

<400> SEQUENCE: 12

```
gtagcagggg ggggaaggga gacatacccg ggggggaaa cagcttgcac ggaagacatt    60
atgaagaact ggtgttggca agaaaacaga tcaacaactt tcaagggaca gacaggtaca   120
acctaggccc aatagtcaac atggtgttaa ggaggctgag agtcatgatg atgacgctga   180
tagggagagg gcatgagcg cgggtaaccc gggatctgaa cccgccagta ggaccctatt    240
gtagataaca ctaatttttt tttttttttt ttttttttt ttagatatta ttatttattt    300
tttttttttt tttaaaaaa aaaaaaaatt tttttaaact acctcaagtt accacactac    360
actcattttt agggggggg                                                 379
```

<210> SEQ ID NO 13
<211> LENGTH: 379
<212> TYPE: DNA
<213> ORGANISM: artificial sequence
<220> FEATURE:
<223> OTHER INFORMATION: PCR product of CSFV of MVP

<400> SEQUENCE: 13

```
tagttagtag aaagacggga aaagggtaca ccccgggagg ggcccacccc ctgcagggga    60
gacattatga gaactggtg ttggcaagaa aacagatcaa aaactttcaa gggacagaca   120
ggtacaatct aggcccaata gtcaacatgg tgttaaggag gctgagagtc atattattgc    180
ccttattggg gaggggggta tgagcgcggg caacccggga tctggacccg ccagtaggac    240
cctattgtag ataacactaa ttttttattt atttagatat tattatttat ttatttattt    300
atttattgaa tgagtaagaa ctggcacaaa ctacctcaag ttaccacacc tccctccttt    360
tttacagccc ttttaatgg                                                 379
```

<210> SEQ ID NO 14
<211> LENGTH: 379
<212> TYPE: DNA
<213> ORGANISM: artificial sequence
<220> FEATURE:
<223> OTHER INFORMATION: PCR product of CSFV of QYHC

<400> SEQUENCE: 14

```
tgtagcaaga ctgggaatag gtacataccc ggagagggtc acaccctgca aggaagacat    60
tatgaagaac tggtgttggc aagaaaacag atcaacaact ttcaagggac agacaggtac   120
aacctaggcc caatagtcaa catggtgtta aggaggctga gagtcatgat gatgacgctg   180
atagggagag gggcatgagc gcgggtaacc cgggatctga acccgccagt aggaccctat    240
tgtagataac actaatttc ttttttcttt ttatttatt tagatattat tatttattta    300
```

```
tttatttatt tatgaatgag taagaactgg tataaacacc tcaagtcacc acactacact    360 cattttttaac agcacttta                                               379
```

<210> SEQ ID NO 15
<211> LENGTH: 379
<212> TYPE: DNA
<213> ORGANISM: artificial sequence
<220> FEATURE:
<223> OTHER INFORMATION: PCR product of CSFV of ZBC

<400> SEQUENCE: 15

```
tgtagcaaga ctgggaatag gtacatcccc ggggaaggtc acaacatgca aggaagacat     60
tatgaagaac tggtgttggc aagaaaacag atcaacaact ttcaagggac agacaggtac    120
aacctaggcc caatagtcaa catggtgtta aggaggctga gagtcatgat gatgacgctg    180 ataggggagag gggcatgagc gcgggtaacc cgggatctga acccgccagt aggaccctat   240
tgtagataac actaattttc ttttttcttt tttatttatt tagatattat tatttattta    300
tttatttatt tattgaatga gtaagaactg gtataaacac ctcaagacca cactacactc    360
atttttaaca gcactttaa                                                 379
```

<210> SEQ ID NO 16
<211> LENGTH: 379
<212> TYPE: DNA
<213> ORGANISM: artificial sequence
<220> FEATURE:
<223> OTHER INFORMATION: PCR product of CSFV of YSC

<400> SEQUENCE: 16

```
gggggccccc cggaaaagtt aaaccctgca cgagacattc aatgaagaac tggtgttggc     60
aagaaaacag atcaacaact ttcaagggac agacaggtac aacctaggcc caatagtcaa    120
catggtgtta aggaggctga gagtcatgat gatgacgctg ataggggagag gggcatgagc   180 gcgggtaacc cgggatctga acccgccagt aggaccctat tgtagacaac actaatcttt   240
tttttttttt tttttttttt tttttttttt tttttttaga tatttttttt tttttttttt    300
tttttttttt aaaaaagcaa aaactggtat aaaccccccc cccccccccc cccccttttt    360
tttttaaaaa aactttagc                                                 379
```

<210> SEQ ID NO 17
<211> LENGTH: 20
<212> TYPE: DNA
<213> ORGANISM: artificial sequence
<220> FEATURE:
<223> OTHER INFORMATION: forward primer 1 for NDV

<400> SEQUENCE: 17

```
atgggcycca gaycttctac                                                 20
```

<210> SEQ ID NO 18
<211> LENGTH: 25
<212> TYPE: DNA
<213> ORGANISM: artificial sequence
<220> FEATURE:
<223> OTHER INFORMATION: reverse primer 1 for NDV

<400> SEQUENCE: 18

```
ctgccactgc tagttgtgat aatcc                                           25
```

<210> SEQ ID NO 19

<211> LENGTH: 534
<212> TYPE: DNA
<213> ORGANISM: artificial sequence
<220> FEATURE:
<223> OTHER INFORMATION: DNA of NDV strain clone30

<400> SEQUENCE: 19

```
ataagctgcg tctctgagat tgcgctccgc ccactcaccc agatc

```
gactacatct ggagggggga gacaggggcg ccttataggc gccattattg cggg        534
```

<210> SEQ ID NO 22
<211> LENGTH: 534
<212> TYPE: DNA
<213> ORGANISM: artificial sequence
<220> FEATURE:
<223> OTHER INFORMATION: DNA of NDV strain VG/GA

<400> SEQUENCE: 22

```
ataagctgcg tctctgagat t

```
                50                  55                  60
Leu Leu Pro Asn Leu Pro Lys Asp Lys Glu Ala Cys Ala Lys Ala Pro
 65                  70                  75                  80

Leu Asp Ala Tyr Asn Arg Thr Leu Thr Thr Leu Leu Thr Pro Leu Gly
                     85                  90                  95

Asp Ser Ile Arg Arg Ile Gln Glu Ser Val Thr Thr Ser Gly Gly Gly
                    100                 105                 110

Arg Gln Gly Arg Leu Ile Gly Ala Ile Ile Gly Gly Val Ala Leu Gly
                115                 120                 125

Val Ala Thr Ala Ala Gln Ile Thr Ala Ala Ala Ala Leu Ile Gln Ala
                130                 135                 140

Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                    165                 170                 175

Val Ala Val Gly Lys Met Gln Gln Phe Val Asn Asp Gln Phe Asn Lys
                180                 185                 190

Thr Ala Gln Glu Leu Asp Cys Ile Lys Ile Ala Gln Gln Val Gly Val
                195                 200                 205

Glu Leu Asn Leu Tyr Leu Thr Glu Leu Thr Thr Val Phe Gly Pro Gln
210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
                260                 265                 270

Pro Ile Leu Tyr Asp Ser Gln Thr Gln Leu Leu Gly Ile Gln Val Thr
                275                 280                 285

Leu Pro Ser Val Gly Asn Leu Asn Asn Met Arg Ala Thr Tyr Leu Glu
                290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
                340                 345                 350

Phe Pro Met Ser Pro Gly Ile Tyr Ser Cys Leu Ser Gly Asn Thr Ser
                355                 360                 365

Ala Cys Met Tyr Ser Lys Thr Glu Gly Ala Leu Thr Thr Pro Tyr Met
                370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                    405                 410                 415

Ser Leu Ile Asp Lys Gln Ser Cys Asn Val Leu Ser Leu Gly Gly Ile
                420                 425                 430

Thr Leu Arg Leu Ser Gly Glu Phe Asp Val Thr Tyr Gln Lys Asn Ile
                435                 440                 445

Ser Ile Gln Asp Ser Gln Val Ile Ile Thr Gly Asn Leu Asp Ile Ser
                450                 455                 460

Thr Glu Leu Gly Asn Val Asn Asn Ser Ile Ser Asn Ala Leu Asn Lys
465                 470                 475                 480
```

```
Leu Glu Glu Ser Asn Arg Lys Leu Asp Lys Val Asn Val Lys Leu Thr
                485                 490                 495

Ser Thr Ser Ala Leu Ile Thr Tyr Ile Val Leu Thr Ile Ile Ser Leu
            500                 505                 510

Val Phe Gly Ile Leu Ser Leu Ile Leu Ala Cys Tyr Leu Met Tyr Lys
            515                 520                 525

Gln Lys Ala Gln Lys Thr Leu Leu Trp Leu Gly Asn Asn Thr Leu
        530                 535                 540

Asp Gln Met Arg Ala Thr Thr Lys Met
545                 550

<210> SEQ ID NO 25
<211> LENGTH: 553
<212> TYPE: PRT
<213> ORGANISM: artificial sequence
<220> FEATURE:
<223> OTHER INFORMATION: protein of NDV strain Mukteswar

<400> SEQUENCE: 25

Met Gly Pro Arg Ser Ser Thr Arg

Leu Pro Ser Val Gly Asn Leu Asn Asn Met Arg Ala Thr Tyr Leu Glu
290                 295                 300

Thr Leu Ser Val Ser Thr Lys Gly Phe Ala Ser Ala Leu Val Pro
305                 310                 315                 320

Lys Val Ala Thr Gln Val Gly Ser Val Ile Glu Glu Leu Asp Thr Ser
            325                 330                 335

Tyr Cys Ile Glu Ala Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
            355                 360                 365

Ala Cys Met Tyr Ser Lys Thr Glu Gly Ala Leu Thr Thr Pro Tyr Met
370                 375                 380

Thr Leu Lys Gly Ser Val Val Ala Asn Cys Gln Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Lys His Ser Cys Asn Val Val Ser Leu Asp Gly Ile
            420                 425                 430

Thr Leu Arg Leu Ser Gly Glu Phe Asp Ala Thr Tyr Gln Lys Asn Ile
            435                 440                 445

Ser Ile Leu Asp Ser Gln Val Leu Val Thr Gly Asn Leu Asp Ile Ser
450                 455                 460

Thr Glu Leu Gly Asn Val Asn Asn Ser Ile Ser Asn Ala Leu Asp Lys
465                 470                 475                 480

Leu Glu Glu Ser Asn Ser Lys Leu Asp Glu Val Asn Val Arg Leu Thr
                485                 490                 495

Ser Thr Ser Ala Leu Ile Thr Tyr Ile Val Leu Thr Val Ile Ser Leu
            500                 505                 510

Val Leu Gly Met Leu Ser Leu Val Leu Ala Cys Tyr Leu Met Tyr Lys
            515                 520                 525

Gln Lys Ala Gln Arg Lys Thr Leu Leu Trp Leu Gly Asn Asn Thr Leu
530                 535                 540

Asp Gln Met Arg Ala Thr Thr Lys Met
545                 550

<210> SEQ ID NO 26
<211> LENGTH: 553
<212> TYPE: PRT
<213> ORGANISM: artificial sequence
<220> FEATURE:
<223> OTHER INFORMATION: protein of NDV strain B1

<400> SEQUENCE: 26

Met Gly Ser Arg Pro Phe Thr Lys Asn Pro Ala Pro Met Met Leu Thr
1               5                   10                  15

Ile Arg Val Ala Leu Val Leu Ser Cys Ile Cys Pro Ala Asn Ser Ile
            20                  25                  30

Asp Gly Arg Pro Phe Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Leu Pro Lys Asp Lys Glu Ala Cys Ala Lys Ala Pro
65                  70                  75                  80

Leu Asp Ala Tyr Asn Arg Thr Leu Thr Thr Leu Leu Thr Pro Leu Gly
                85                  90                  95

-continued

```
Asp Ser Ile Arg Arg Ile Gln Glu Ser Val Thr Thr Ser Gly Gly Gly
            100                 105                 110
Arg Gln Gly Arg Leu Ile Gly Ala Ile Ile Gly Val Ala Leu Gly
        115                 120                 125
Val Ala Thr Ala Ala Gln Ile Thr Ala Ala Ala Leu Ile Gln Ala
    130                 135                 140
Lys Gln Asn Ala Ala Asn Ile Leu Arg Leu Lys Glu Ser Ile Ala Ala
145                 150                 155                 160
Thr Asn Glu Ala Val His Glu Val Thr Asp Gly Leu Ser Gln Leu Ala
                165                 170                 175
Val Ala Val Gly Lys Met Gln Gln Phe Val Asn Asp Gln Phe Asn Lys
            180                 185                 190
Thr Ala Gln Glu Leu Asp Cys Ile Lys Ile Ala Gln Gln Val Gly Val
        195                 200                 205
Glu Leu Asn Leu Tyr Leu Thr Glu Leu Thr Thr Val Phe Gly Pro Gln
    210                 215                 220
Ile Thr Ser Pro Ala Leu Asn Lys Leu Thr Ile Gln Ala Leu Tyr Asn
225                 230                 235                 240
Leu Ala Gly Gly Asn Met Asp Tyr Leu Leu Thr Lys Leu Gly Ile Gly
                245                 250                 255
Asn Asn Gln Leu Ser Ser Leu Ile Gly Ser Gly Leu Ile Thr Gly Asn
            260                 265                 270
Pro Ile Leu Tyr Asp Ser Gln Thr Gln Leu Leu Gly Ile Gln Val Thr
        275                 280                 285
Leu Pro Ser Val Gly Asn Leu Asn Asn Met Arg Ala Thr Tyr Leu Glu
    290                 295                 300
Thr Leu Ser Val Ser Thr Thr Arg Gly Phe Ala Ser Ala Leu Val Pro
305                 310                 315                 320
Lys Val Val Thr Gln Val Gly Ser Val Ile Glu Glu Leu Asp Thr Ser
                325                 330                 335
Tyr Cys Ile Glu Thr Asp Leu Asp Leu Tyr Cys Thr Arg Ile Val Thr
            340                 345                 350
Phe Pro Met Ser Pro Gly Ile Tyr Ser Cys Leu Ser Gly Asn Thr Ser
        355                 360                 365
Ala Cys Met Tyr Ser Lys Thr Glu Gly Ala Leu Thr Thr Pro Tyr Met
    370                 375                 380
Thr Ile Lys Gly Ser Val Ile Ala Asn Cys Lys Met Thr Thr Cys Arg
385                 390                 395                 400
Cys Val Asn Pro Pro Gly Ile Ile Ser Gln Asn Tyr Gly Glu Ala Val
                405                 410                 415
Ser Leu Ile Asp Lys Gln Ser Cys Asn Val Leu Ser Leu Gly Gly Ile
            420                 425                 430
Thr Leu Arg Leu Ser Gly Glu Phe Asp Val Thr Tyr Gln Lys Asn Ile
        435                 440                 445
Ser Ile Gln Asp Ser Gln Val Ile Ile Thr Gly Asn Leu Asp Ile Ser
    450                 455                 460
Thr Glu Leu Gly Asn Val Asn Asn Ser Ile Ser Asn Ala Leu Asn Lys
465                 470                 475                 480
Leu Glu Glu Ser Asn Arg Lys Leu Asp Lys Val Asn Val Lys Leu Thr
                485                 490                 495
Ser Thr Ser Ala Leu Ile Thr Tyr Ile Val Leu Thr Ile Ile Ser Leu
            500                 505                 510
```

```
Val Phe Gly Ile Leu Ser Leu Ile Leu Ala Cys Tyr Leu Met Tyr Lys
            515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550

<210> SEQ ID NO 27
<211> LENGTH: 553
<212> TYPE: PRT
<213> ORGANISM: artificial sequence
<220> FEATURE:
<223> OTHER INFORMATION: protein of NDV strain VG/GA

<400> SEQUENCE: 27

Met Gly Ser Arg Pro Ser Thr Lys Asn Pro Ala Pro Met Met Leu Thr
1               5                   10                  15

Ile Arg Val Ala Leu Val Leu Ser Cys Ile Cys Pro Ala Asn Ser Ile
            20                  25                  30

Asp Gly Arg Pro Leu Ala Ala Ala Gly Ile Val Val Thr Gly Asp L

Lys Val Val Thr Gln Val Gly Ser Val Ile Glu Glu Leu Asp Thr Ser
               325                 330                 335

Tyr Cys Ile Glu Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
            420                 425                 430

Thr Leu Arg Leu Ser Gly Glu Phe Asp Val Thr Tyr Gln Lys Asn Ile
        435                 440                 445

Ser Ile Gln Asp Ser Gln Val Ile Ile Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
                485                 490                 495

Ser Thr Ser Ala Leu Ile Thr Tyr Ile Val Leu Thr Ile Ile Ser Leu
            500                 505                 510

Val Phe Gly Ile Leu Ser Leu Ile Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550

<210> SEQ ID NO 28
<211> LENGTH: 553
<212> TYPE: PRT
<213> ORGANISM: artificial sequence
<220> FEATURE:
<223> OTHER INFORMATION: protein of NDV strain KBNP

<400> SEQUENCE: 28

Met Gly Ser Lys Leu Ser Thr Arg Ile Pro Ala Pro Leu Met Leu Thr
1               5                   10                  15

Thr Arg Ile Thr Leu Ile Leu Ser Cys Ile Arg Pro Thr Ser Ser Leu
            20                  25                  30

Asp Gly Arg Pro Leu Ala Ala Ala Gly Ile Val Val Thr Gly Asp Lys
35 40 45

Ala Val Asn Val Tyr Thr Ser Ser Gln Thr Gly Ser Ile Ile Val Lys
50 55 60

Leu Leu Pro Asn Met Pro Arg Asp Lys Glu Ala Cys Ala Lys Ala Pro
65 70 75 80

Leu Glu Ala Tyr Asn Arg Thr Leu Thr Thr Leu Leu Thr Pro Leu Gly
85 90 95

Asp Ser Ile Arg Lys Ile Gln Gly Ser Val Ser Thr Ser Gly Gly Gly
100 105 110

Arg Gln Ala Arg Leu Ile Gly Ala Val Ile Gly Ser Val Ala Leu Gly
115 120 125

```
Val Ala Thr Ala Ala Gln Ile Thr Ala Ala Ala Leu Ile Gln Ala
    130                 135                 140
Asn Gln Asn Ala Ala Asn Ile Leu Arg Leu Lys Glu Ser Ile Ala Ala
145                 150                 155                 160
Thr Asn Glu Ala Val His Glu Val Thr Asp Gly Leu Ser Gln Leu Ser
                165                 170                 175
Val Ala Val Gly Lys Met Gln Gln Phe Val Asn Asp Gln Phe Asn Asn
                180                 185                 190
Thr Ala Arg Glu Leu Asp Cys Ile Lys Ile Thr Gln Gln Val Gly Val
            195                 200                 205
Glu Leu Asn Leu Tyr Leu Thr Glu Leu Thr Thr Val Phe Gly Pro Gln
210                 215                 220
Ile Thr Ser Pro Ala Leu Thr Gln Leu Thr Ile Gln Ala Leu Tyr Asn
225                 230                 235                 240
Leu Ala Gly Gly Asn Met Asn Tyr Leu Leu Thr Lys Leu Gly Ile Gly
                245                 250                 255
Asn Asn Gln Leu Ser Ser Leu Ile Gly Ser Gly Leu Ile Thr Gly Tyr
            260                 265                 270
Pro Ile Leu Tyr Asp Ser Gln Thr Gln Leu Leu Gly Ile Gln Val Asn
        275                 280                 285
Leu Pro Ser Val Gly Asn Leu Asn Asn Met Arg Ala Thr Tyr Leu Glu
    290                 295                 300
Thr Leu Ser Val Ser Thr Thr Lys Gly Tyr Ala Ser Ala Leu Val Pro
305                 310                 315                 320
Lys Val Val Thr Gln Val Gly Ser Val Ile Glu Glu Leu Asp Thr Ser
                325                 330                 335
Tyr Cys Ile Glu Ser Asp Leu Asp Leu Tyr Cys Thr Arg Ile Val Thr
                340                 345                 350
Phe Pro Met Ser Pro Gly Ile Tyr Ser Cys Leu Ser Gly Asn Thr Ser
            355                 360                 365
Ala Cys Met Tyr Ser Lys Thr Glu Gly Ala Leu Thr Thr Pro Tyr Met
370                 375                 380
Ala Leu Lys Gly Ser Val Ile Ala Asn Cys Lys Ile Thr Thr Cys Arg
385                 390                 395                 400
Cys Thr Asp Pro Pro Gly Ile Ile Ser Gln Asn Tyr Gly Glu Ala Val
                405                 410                 415
Ser Leu Ile Asp Arg His Ser Cys Asn Val Leu Ser Leu Asp Gly Ile
                420                 425                 430
Thr Leu Arg Leu Ser Gly Glu Phe Asp Ala Thr Tyr Gln Lys Asn Ile
            435                 440                 445
Ser Ile Leu Asp Ser Gln Val Ile Val Thr Gly Asn Leu Asp Ile Ser
        450                 455                 460
Thr Glu Leu Gly Asn Val Asn Asn Ser Ile Ser Asn Ala Leu Asp Ser
465                 470                 475                 480
Leu Ala Glu Ser Asn Ser Lys Leu Glu Lys Ile Asn Val Arg Leu Thr
                485                 490                 495
Ser Thr Ser Ala Leu Ile Thr Tyr Ile Val Leu Thr Val Ile Ser Leu
            500                 505                 510
Val Phe Gly Ala Phe Ser Leu Gly Leu Ala Cys Tyr Leu Met Tyr Lys
        515                 520                 525
Gln Lys Ala Gln Gln Lys Thr Leu Leu Trp Leu Gly Asn Asn Thr Leu
    530                 535                 540
Asp Gln Met Arg Ala Thr Thr Arg Ala
```

<210> SEQ ID NO 29
<211> LENGTH: 16
<212> TYPE: DNA
<213> ORGANISM: artificial sequence
<220> FEATURE:
<223> OTHER INFORMATION: forward primer for IB-QX for IBV

<400> SEQUENCE: 29
cttatgcagt agtcaa                                                    16

<210> SEQ ID NO 30
<211> LENGTH: 22
<212> TYPE: DNA
<213> ORGANISM: artificial sequence
<220> FEATURE:
<223> OTHER INFORMATION: reverse primer for IB-QX for IBV

<400> SEQUENCE: 30
cacgtggaat catgcctgtt at                                             22

<210> SEQ ID NO 31
<211> LENGTH: 25
<212> TYPE: DNA
<213> ORGANISM: artificial sequence
<220> FEATURE:
<223> OTHER INFORMATION: forward primer 2 for NDV
<220> FEATURE:
<221> NAME/KEY: misc_feature
<222> LOCATION: (17)..(17)
<223> OTHER INFORMATION: N is inosine

<400> SEQUENCE: 31
ctgccactgc tagttgngat aatcc                                          25

<210> SEQ ID NO 32
<211> LENGTH: 22
<212> TYPE: DNA
<213> ORGANISM: artificial sequence
<220> FEATURE:
<223> OTHER INFORMATION: reverse primer 2 for NDV
<220> FEATURE:
<221> NAME/KEY: misc_feature
<222> LOCATION: (10)..(10)
<223> OTHER INFORMATION: N is inosine
<220> FEATURE:
<221> NAME/KEY: misc_feature
<222> LOCATION: (19)..(19)
<223> OTHER INFORMATION: N is inosine

<400> SEQUENCE: 32
ccttggtgan tctatccgna gg                                             22

<210> SEQ ID NO 33
<211> LENGTH: 6
<212> TYPE: PRT
<213> ORGANISM: artificial sequence
<220> FEATURE:
<223> OTHER INFORMATION: F fusion of NDV clearage site motif 1

<400> SEQUENCE: 33

Arg Arg Arg Lys Arg Phe
1               5

<210> SEQ ID NO 34
<211> LENGTH: 6
<212> TYPE: PRT

<213> ORGANISM: artificial sequence
<220> FEATURE:
<223> OTHER INFORMATION: F fusion of NDV cleavage site motif 2

<400> SEQUENCE: 34

Gly Arg Gln Gly Arg Leu
1               5

<210> SEQ ID NO 35
<211> LENGTH: 6
<212> TYPE: PRT
<213> ORGANISM: artificial sequence
<220> FEATURE:
<223> OTHER INFORMATION: F fusion of NDV clearage site motif 3

<400> SEQUENCE: 35

Gly Lys Gln Gly Arg Leu
1               5

<210> SEQ ID NO 36
<211> LENGTH: 1611
<212> TYPE: DNA
<213> ORGANISM: artificial sequence
<220> FEATURE:
<223> OTHER INFORMATION: DNA of M5365

<400> SEQUENCE: 36
atgttggtga agtcactgtt cttagtgact ctttcgtttg cactatgtag tgctaatttg 60
tataataatg atagttatgt ttactactac cagagtgcat ttagaccccc taatggttgg 120
catttacaag gaggtgctta tgcaatagtt aacagttctt catattataa taacgcaggt 180
ggttcctctg aatgcactgc tggtattatt aaggatgttt ataatcttag cgcagcttct 240
atatctatga cagcaccacc tacgggtatg tcatggtctg tttcacaatt ttgtacagca 300
cactgtaact tctctgactt tacagtgttt gtcacacatt gttttaaaag tggtcgcgga 360
cagtgtcctt taacaggcct aataccacag aattacattc gcatctctgc tatgagaaat 420
ggttctctct tttataattt aacagttagt gcgtctaaat accctaattt taaatctttt 480
caatgtgtta ataatgccac atctgtgtat ttaaatggtg accttgtttt ctcttctaac 540
atgactactg atgttacagc agcgggtgtg tattttaaag caggtggacc tgttacttac 600
agtgttatga agcagtttca ggtcttagct tattttgtta atggcactgt acaagaagtt 660
attttgtgcg atgacacacc tagaggtttg ctagcatgtc aatataatac tggcaatttt 720
tcagaaggct tctacctttt tactaattat agtttagtta aggaaaagtt attgtttatc 780
cgaaggagtg taaatcactc gggcgttaac caattcactt ttactaatgt aagtaaagcc 840
cagcctaata ggggggggtgt tcaacttttc catttatatc aaacgcaacc agctcagagg 900
ggtaatataa ttttaattgg ccatttctca gtcagtctgt gtataaagca agtgatttta 960
tgtatgggtc ttatcccccc tagttgttct tttagaccag aaaccattac cagtggtttg 1020
tggtttaatt ccttgtcagt ttctcttact tatggacccc tacagggagg gtgcaagcaa 1080
tctgtcttca gtagtaaggc aacgtgttgt tatgcctact cttataatgg cccaagggca 1140
tgtaaaggtg tttattcagg tgaattaagt acgagttttg aatgtggatt gctggtttat 1200
gttactaaga gtgatggctc tcgtatacag actagaacgg agcccttagt attaacgcaa 1260
ctcaattata ataatattac tttagataag tgtgttgcct ataatatata tggcagagta 1320
ggccaaggtt ttattactaa tgtgactgat tctgctgcta attttagtta tttagcagat 1380
ggtgggttag ctattttaga tacttcgggc gccatagatg tttttgttgt acagggcagc 1440

```
tatggtctta attattacaa ggttaatcct tgtgaagatg ttaaccaaca gtttgtagtg    1500
tctggtggca atatagttgg tattcttact tctagaaata aaacaggttc tgaacaggtt    1560
gagaaccagt tttatgttaa gttaaccaat agctcacatc gtcgcaggcg t             1611

<210> SEQ ID NO 37
<211> LENGTH: 1593
<212> TYPE: DNA
<213> ORGANISM: artificial sequence
<220> FEATURE:
<223> OTHER INFORMATION: DNA of V9/04

<400> SEQUENCE: 37
atgttggtga agtcactgtt cttagtgact cttttgtttg cactatgtag tgctaatttg      60
tataataatg atagttatgt ttactactac cagagtgcat tgagaccccc taatggctgg     120
cacttacaag gaggcgctta tgcagtagtt aacagttctg tacgttataa taatgcaggt     180
tcattatcag catgcactgt tggtattatt aaggatgtgt ttaattctac agcggcttct     240
atttctatga tagcaccgca attaggtatg tcgtggtcca aggcacaaat tgtacggca      300 cactgtaatt tctcggatgt tacagttttt gtcacacatt gttatagtag tggtagtggg     360
tcttgtccta taacaggcat gattccacag aatcatattc gtatttctgc catgaaaaat     420
ggttatttat tttataattt aacagttagt gtatctaagt accctacttt taaatccttt     480
caatgtgtta ataatcaaac atccgtctac cttaatggag accttgttta cacttctaac     540
acgaccactg ctgttacatc aacgggtggg gatttttaaag caagtggacc tggtacttac     600
agtggtatga agcagtttca ggccttaact tatttgttaa tggcactgta ccagaggtat     660
tttggcgatg accccctaga ggttgctagc atgtcatata atactggcaa ttttcagaag     720
gctttacctt ttactaataa aagttatttta ggaaagttat gttttctgag agagggtaaa     780
tcactttggt ttaacaaatt tccccgtttta aaggaaataa tgccccacct atacggggagg   840 tgtggtagtt ttatttgttc caaactcaaa ctgcgaaatg ggttattaca ctttaaattt    900
ctcgtttctc agcgggtttc ggtatgtggc aagggttta atgtatgggt cttaccgccc    960
caaagtgtat ttttagtcca gaaaccatta ataatgggtt tatggtttaa ttcactttct  1020
atttcatttg cttatggtcc tcttcagggt ggatgcaagc aatctgtttt tcaaggtaga  1080
gcaacgtgtt gttttgctta ttcatataat ggccctcacg catgtaaagg tgtttacagt  1140
ggtgagttat ctaagttttt tgaatgtgga ttgttggttt atgttactaa gagtgatggc  1200
tcgcgtatac aaacagccac tgaaccacca gtcataactc aacacaacta taataatatt  1260
acattggata gtgtgttga gtataacata tatggcaaaa caggccaagg ttttattact  1320
aatgtaacta actctgctgc tagttataat tatttagcag attcaggatt ggctatctta  1380
gatacatctg gtgccataga catctttgtt gtacaaggtg ctcatggtct taattattat  1440
aaagttaacc cctgtgaaga tgttaaccaa caatttgtag tgtctggtgg tagtatagtt  1500
ggtattctca cctcacgtaa tgaaagtggc tctcagtcta ttgaggatca attttatatc  1560
aaacttgtta atggaacacg gcgtgttaga cgt                                1593

<210> SEQ ID NO 38
<211> LENGTH: 1710
<212> TYPE: DNA
<213> ORGANISM: artificial sequence
<220> FEATURE:
<223> OTHER INFORMATION: DNA of THA50151
```

<400> SEQUENCE: 38

```
atgttggtga attcactgtt cctagtgacg tttttgtttg cactatgtag tgctaatttg      60
tatattaata atagttatgt ttactactac cagagtgcat ttagacccec tactggttgg    120
catttacaag gaggtgctta tgcagtagtt aatagttctg tatattataa aacgcaggt     180
ggttcctctg aatgcactgc tggtattatt aaggatgttt ataatcttag cgcagctgct    240
atatctatga cagcaccacc tacaggtatg tcatggtctg cttcacaatt ttgtacagca    300
cactgtaact tttctgattt tacagtgttt gttacacatt gttttaaaag tggtcatgga    360
cattgtcctt taacaggtct aataccaagg aattacattc gcatctctgc tatgagaaat    420
ggtcttcttt tttataattt aacagttagt gtatctaaat accctaattt taaatctctt    480
caatgtgtta ataatgccac atctgtgtat ttaaatggtg accttgtttt ctcttctaac    540
atgactactg atgttacatc agcgggtgtg tattttaaag caggtggacc tgttatttat    600
agtgttatga acagtttaa ggttctggct tactttgtta atggtactgt gcaagatgta     660
atcctgtgcg atgacacacc tagaggtttg ctagcctgtc aatataacac tggcaatttt    720
tcagatggct tttatccttt tactaatagt actttagtta gggaaaagtt cattgtctat    780
cgcgaaagta gtgttaatac tactctggcg ttaactaatt tcacttttac taatgtaagt    840
aatgcacagc ctaatagtgg tggtgttcat acttttcatt tatatcaaac gcaaacagct    900
cagagtggtt attataattt taatttgtca tttctgagtc agtttgtgta taagcaagt     960
gattttatgt atgggtctta tcaccctagt tgttcttta gaccggaaac cattaacagt     1020
ggtttgtggt taattccttt gtcagtttct cttacttatg accctaca gggaggtgt      1080
aagcaatctg tctttagtgg tagggcaacg tgttgttatg cctactctta taatggccca    1140
agggcatgta aggtgtttta ttcaggtgaa ttaagcacga gttttgaatg tggattgctg    1200
gtttatgtta ctatgagtgc tggctctcgt atacagacta gaacggagcc cttagtatta    1260
acgcaacaca attataataa tattactttta gataagtgtg ttgactataa tatatatggc    1320
agagtaggcc aaggttttat tactaatgtg actgattctg ctgctaattt tagttattta    1380
gcagatggtg ggttagctat tttagatact tcgggtgcca tagatgtttt tgttgtacag    1440
ggcatctatg gtcttaatta ttacaaggtt aatccttgtg aagatgttaa ccaacagttt    1500
gtagtgtctg gtggtaatat agttggcttt ctcacttctc gtaatgaaac tggttctcag    1560
cctattgaga accaattta tgttaaactc actaatgtaa gtcgtcgtca cagacgttcc     1620
attagtgaaa atgttacaag ctgtccatac gtaagttatg gcaggttttg tatacaacct    1680
gatggtctta ttaagcaaat agtaccgcaa                                    1710
```

<210> SEQ ID NO 39
<211> LENGTH: 1710
<212> TYPE: DNA
<213> ORGANISM: artificial sequence
<220> FEATURE:
<223> OTHER INFORMATION: DNA of THA40151

<400> SEQUENCE: 39

```
atgttggtga attcactgtt cctagtgacg tttttgtttg cactatgtag tgctaatttg     60
tatattaata atagttatgt ttactactac cagagtgcat ttagacccec tactggttgg   120
catttacaag gaggtgctta tgcagtagtt aatagttctg tatattataa aacgcaggt    180
ggttcctctg aatgcactgc tggtattatt aaggatgttt ataatcttag cgcagctgct   240
atatctatga cagcaccacc tacaggtatg tcatggtctg tttcacaatt ttgtacagca   300
```

```
cactgtaact tttctgattt tacagtgttt gttacacatt gttttaaaag tggtcatgga    360
cattgtcctt taacaggtct aataccaaag aattacattc gcatctctgc tatgagaaat    420
ggtcttcttt tttataattt aacagttagt gtatctaaat accctaattt taaatctctt    480
caatgtgtta ataatgccac atctgtgtat ttaaatggtg accttgtttt ctcttctaac    540
atgactactg atgttacatc agcgggtgtg tattttaaag caggtggacc tgttatttat    600
agtgttatga aacagtttaa ggttctggct tactttgtta atggtactgt gcaagatgta    660
atcctgtgtg atgacacacc tagaggtttg ctagcctgtc aatataacac tggcagtttt    720
tcagatggct tttatccttt tactaatagt actttagtta gggaaaagtt cattgtctat    780
cgcgaaagta gtgttaatac tactctggcg ttaactaatt tcacttttac taatgtaagt    840
aatgcacagc taatagtgg tggtgttcat acttttcatt tatatcaaac gcaaacagct    900
cagagtggtt attataattt taatttgtca tttctgagtc agtttgtgta taaagcaagt    960
gattttatgt atgggtctta tcaccctagt tgttcttta gaccggaaac cattaacagt    1020
ggtttgtggt ttaattcctt gtcagtttct cttacttatg gacccctaca gggagggtgt    1080
aagcaatctg tctttagtgg tagggcaacg tgttgttatg cctactctta taatggccca    1140
agggcatgta aggtgttta ttcaggtgaa ttaagcacga gttttgaatg tggattgctg    1200
gtttatgtta ctatgagtgc tggctctcgt atacagacta gaacggagcc cttagtatta    1260
acgcaacaca attataataa tattactta gataagtgtg ttgactataa tatatatggc    1320
agagtaggcc aaggttttat tactaatgtg actgattctg ctgctaattt tagttattta    1380
gcagatggtg ggttagctat tttagatact tcgggtgcca tagatgtttt tgttgtacag    1440
ggcatctatg gtcttaatta ttacaaggtt aatccttgtg aagatgttaa ccaacagttt    1500
gtagtgtctg gtggtaatat agttggcttt ctcacttctc gtaatgaaac tggttctcag    1560
cctattgaga accaatttta tgttaaactc actaatgtaa gtcgtcgtca cagacgttcc    1620
attagtgaaa atgttacaag ctgtccatac gtaagttatg gcaggttttg tatacaacct    1680
gatggtctta ttaagcaaat agtaccgcaa                                      1710
```

<210> SEQ ID NO 40
<211> LENGTH: 1710
<212> TYPE: DNA
<213> ORGANISM: artificial sequence
<220> FEATURE:
<223> OTHER INFORMATION: DNA of THA20151

<400> SEQUENCE: 40

```
atgttggtga attcactgtt cctagtgacg ttttgtttg cactatgtag tgctaatttg    60
tatattaata atagttatgt ttactactac cagagtgcat ttagaccccc tactggttgg    120
catttacaag gaggtgctta tgcagtagtt aatagttctg tatattataa taacgcaggt    180
ggttcctctg aatgcactgc tggtattatt aaggatgttt ataatcttag cgcagctgct    240
atatctatga cagcaccacc tacaggtatg tcatggtctg cttcacaatt ttgtacagca    300
cactgtaact tttctgattt tacagtgttt gttacacatt gttttaaaag tggtcatgga    360
cattgtcctt taacaggtct aataccaaag aattacattc gcatctctgc tatgagaaat    420
ggtcttcttt tttataattt aacagttagt gtatctaaat accctaattt taaatctctt    480
caatgtgtta ataatgccac atctgtgtat ttaaatggtg accttgtttt ctcttctaac    540
atgactactg atgttacatc agcgggtgtg tattttaaag caggtggacc tgttatttat    600
```

```
agtgttatga aacagtttaa ggttctggct tactttgtta atggtactgt gcaagatgta    660
atcctgtgtg atgacacacc tagaggtttg ctagcctgtc aatataacac tggcaatttt    720
tcagatggct tttatccttt tactaatagt actttagtta gggaaaagtt cattgtctat    780
cgcgaaagta gtgttaatac tactctggcg ttaactaatt tcacttttac taatgtaagt    840
aatgcacagc ctaatagtgg tggtgttcat acttttcatt tatatcaaac gcaaacagct    900
cagagtggtt attataattt taatttgtca tttctgagtc agtttgtgta taaagcaagt    960
gattttatgt atgggtctta tcaccctagt tgttctttta gaccggaaac cattaacagt   1020
ggtttgtggt taattccctt gtcagtttct cttacttatg gaccctaca gggagggtgt   1080 aagcaatctg tctttagtgg tagggcaacg tgttgttatg cctactctta atgggccca   1140 agggcatgta aagtgttta ttcaggtgaa ttaagcacga ttttgaatg tggattgctg   1200 gtttatgtta ctatgagtgc tggctctcgt atacagacta gaacggagcc cttagtatta   1260
acgcaacaca attataataa tattacttta gataagtgtg ttgactataa tatatatggc   1320
agagtaggcc aaggttttat tactaatgtg actgattctg ctgctaattt tagttattta   1380
gcagatggtg ggttagctat tttagatact tcgggtgcca tagatgtttt tgttgtacag   1440
ggcatctatg gtcttaatta ttacaaggtt aatccttgtg aagatgttaa ccaacagttt   1500
gtagtgtctg gtggtaatat agttggcttt ctcacttctc gtaatgaaac tggttctcag   1560
cctattgaga accaattta tgttaaactc actaatgtaa gtcgtcgtca cagacgttcc   1620
attagtgaaa atgttacaag ctgtccatac gtaagttatg gcaggttttg tatacaacct   1680
gatggtctta ttaagcaaat agtaccgcaa                                    1710

<210> SEQ ID NO 41
<211> LENGTH: 1710
<212> TYPE: DNA
<213> ORGANISM: artificial sequence
<220> FEATURE:
<223> OTHER INFORMATION: DNA of THA90151

<400> SEQUENCE: 41
atgttggtga attcactgtt cctagtgacg ttttgtttg cactatgtag tgctaatttg     60
tatattaata atagttatgt ttactactac cagagtgcat ttagaccccc tactggttgg    120
catttacaag gaggtgctta tgcagtagtt aatagttctg tatattataa taacgcaggt    180
ggttcctctg aatgcactgc tggtattatt aaggatgttt ataatcttag cgcagctgct    240
atatctatga cagcaccacc tataggtatg tcatggtctg cttcacaatt ttgtacagca    300
cactgtaact tttctgattt tacagtgttt gttacacatt gttttaaaag tggtcatgga    360
cattgtcctt taacaggtct aataccaaag aattacattc gcatctctgc tatgagaaat    420
ggtcttcttt tttataattt aacagttagt gtatctaaat accctaattt taaatctctt    480
caatgtgtta ataatgccac atctgtgtat ttaaatggtg accttgtttt ctcttctaac    540
atgactactg atgttacatc agcgggtgtg tattttaaag caggtggacc tgttatttat    600
agtgttatga acagtttaa ggttctggct tactttgtta atggtactgt gcaagatgta    660
atcctgtgtg atgacacacc tagaggtttg ctagcctgtc aatataacac tggcaatttt    720
tcagatggct tttatccttt tactaatagt actttagtta gggaaaagtt cattgtctat    780
cgcgaaagta gtgttaatac tactctggcg ttaactaatt tcacttttac taatgtaagt    840
aatgcacagc ctaatagtgg tggtgttcat acttttcatt tatatcaaac gcaaacagct    900
cagagtggtt attataattt taatttgtca tttctgagtc agtttgtgta taaagcaagt    960
```

```
gattttatgt atgggtctta tcaccctagt tgttctttta gaccggaaac cattaacagt       1020
ggtttgtggt ttaattcctt gtcagtttct cttacttatg gaccctaca gggagggtgt        1080 aagcaatctg tctttagtgg tagggcaacg tgttgttatg cctactctta taatggccca       1140
agggcatgta aaggtgttta ttcaggtgaa ttaagcacga gttttgaatg tggattgctg       1200
gtttatgtta ctatgagtgc tggctctcgt atacagacta gaacggagcc cttagtatta      1260
acgcaacaca attataataa tattacttta gataagtgtg ttgactataa tatatatggc      1320
agagtaggcc aaggttttat tactaatgtg actgattctg ctgctaattt tagttattta      1380
gcagatggtg ggttagctat tttagatact tcgggtgcca tagatgtttt tgttgtacag      1440
ggcatctatg gtcttaatta ttacaaggtt aatccttgtg aagatgttaa ccaacagttt      1500
gtagtgtctg gtggtaatat agttggcttt ctcacttctc gtaatgaaac tggttctcag     1560
cctattgaga accaatttta tgttaaactc actaatgtaa gtcgtcgtca cagacgttcc     1620
attagtgaaa atgttacaag ctgtccatac gtaagttatg gcaggttttg tatacaacct    1680
gatggtctta ttaagcaaat agtaccgcaa                                       1710
```

<210> SEQ ID NO 42
<211> LENGTH: 1710
<212> TYPE: DNA
<213> ORGANISM: artificial sequence
<220> FEATURE:
<223> OTHER INFORMATION: DNA of THA60151

<400> SEQUENCE: 42

```
atgttggtga attcactgtt cctagtgacg ttttttgtttg cactatgtag tgctaatttg       60
tatattaata atagttatgt ttactactac cagagtgcat ttagaccccc tactggttgg       120
catttacaag gaggtgctta tgcagtagtt aatagttctg tatattataa taacgcaggt       180
ggttcctctg aatgcactgc tggtattatt aaggatgttt ataatcttag cgcagctgct       240
atatctatga cagcaccacc tataggtatg tcatggtctg cttcacaatt ttgtacagca      300
cactgtaact tttctgattt tacagtgttt gttacacatt gttttaaaag tggtcatgga      360
cattgtcctt taacaggtct aataccaaag aattacattc gcatctctgc tatgagaaat       420 ggtcttctttt tttataattt aacagttagt gtatctaaat accctaattt taatctctt       480 caatgtgtta ataatgccac atctgtgtat ttaaatggtg accttgtttt ctcttctaac      540
atgactactg atgttacatc agcgggtgtg tattttaaag caggtggacc tgttatttat      600
agtgttatga acagtttaa ggttctggct tactttgtta atggtactgt gcaagatgta     660
atcctgtgtg atgacacacc tagaggtttg ctagcctgtc aatataacac tggcaatttt      720
tcagatggct tttatccttt tactaatagt actttagttta gggaaaagtt cattgtctat      780
cgcgaaagta gtgttaatac tactctggcg ttaactaatt tcactttac taatgtaagt      840 aatgcacagc taatagtggt tggtgttcat acttttcatt tatatcaaac gcaaacagct      900
cagagtggtt attataattt taatttgtca tttctgagtc agtttgtgta taaagcaagt      960
gattttatgt atgggtctta tcaccctagt tgttctttta gaccggaaac cattaacagt      1020
ggtttgtggt ttaattcctt gtcagtttct cttacttatg gaccctaca gggagggtgt     1080 aagcaatctg tctttagtgg tagggcaacg tgttgttatg cctactctta taatggccca     1140
agggcatgta aaggtgttta ttcaggtgaa ttaagcacga gttttgaatg tggattgctg     1200
gtttatgtta ctatgagtgc tggctctcgt atacagacta gaacggagcc cttagtatta    1260
```

| | |
|---|---|
| acgcaacaca attataataa tattacttta gataagtgtg ttgactataa tatatatggc | 1320 |
| agagtaggcc aaggttttat tactaatgtg actgattctg ctgctaattt tagttattta | 1380 |
| gcagatggtg ggttagctat tttagatact tcgggtgcca tagatgtttt tgttgtacag | 1440 |
| ggcatctatg gtcttaatta ttacaaggtt aatccttgtg aagatgttaa ccaacagttt | 1500 |
| gtagtgtctg gtggtaatat agttggcttt ctcacttctc gtaatgaaac tggttctcag | 1560 |
| cctattgaga accaatttta tgttaaactc actaatgtaa gtcgtcgtca cagacgttcc | 1620 |
| attagtgaaa atgttacaag ctgtccatac gtaagttatg gcaggttttg tatacaacct | 1680 |
| gatggtctta ttaagcaaat agtaccgcaa | 1710 |

<210> SEQ ID NO 43
<211> LENGTH: 1657
<212> TYPE: DNA
<213> ORGANISM: artificial sequence
<220> FEATURE:
<223> OTHER INFORMATION: DNA of AF193423

<400> SEQUENCE: 43

| | |
|---|---|
| atgttgggga agtcactgtt tttagtgacc attttgtgtg cactatgtag tgcaaatttg | 60 |
| ttcgattctg ctaataatta tgtgtactac taccaaagtg cctttaggcc tccaaatgga | 120 |
| tggcatttgc aaggggtgc ttatgcagta gtgaattcca ctaattatag taataatgca | 180 |
| ggttctgcac ctcagtgcac tgttggtgtt attaaggacg tctataatca aagtgcggct | 240 |
| tctatagcta tgacagcacc tcttcagggt atggcttggt ctaagtcaca attttgtagt | 300 |
| gcacactgta acttttctga aattacagtt tttgtcacac attgttatag tagtggtagc | 360 |
| gggtcttgtc ctataacagg catgattcca cgtgatcata ttcgtatttc tgcaatgaaa | 420 |
| aatggttctt ttattttataa tttaacagtt agcgtatcta atacccctaa ttttaaatct | 480 |
| tttcaatgtg ttaacaactt cacatctgtt tatttaaatg gtgatcttgt ttttacttcc | 540 |
| aacaaaacta ctgatgttac gtcagcaggt gtgtatttta aagcaggtgg acctgtaaat | 600 |
| tataatatta tgaaagaatt taaggttctt gcttactttg ttaatggtac agcacaagat | 660 |
| gtaattttgt gcgataattc ccccaagggt ttgctagcct gtcaatataa cactggcaat | 720 |
| ttttcagatg gcttttatcc ttttactaat agtactttag ttagggaaaa gttcattgtc | 780 |
| tatcgcgaaa gtagtgttaa tactactctg gcgttaacta atttcacttt tactaatgta | 840 |
| agtaatgcac agcctaatag tggtggtgtt aatactttc atttatatca aacacaaaca | 900 |
| gctcagagtg gttattataa ttttaatttg tcatttctga gtcagtttgt gtataaggca | 960 |
| agtgatttta tgtatgggtc ttaccaccct agttgttctt ttagaccaga aaccattaat | 1020 |
| agtggtttgt ggtttaattc cttgtcagtt tctcttactt atggacccct acagggaggg | 1080 |
| tgtaagcaat ctgtttttag tggtaaggca acgtgttgtt atgcctactc ttataatggc | 1140 |
| ccaagggcat gtaaaggtgt ttattcaggt gaattaagca tgaattttga atgtggattg | 1200 |
| ctggtttatg ttactaagag tcatggctct cgtatacaga ctagaacgga gcccttagta | 1260 |
| ttaacgcaac acaattataa taatattact ttagataagt gtgttgctta atatatat | 1320 |
| ggcagagtag gccaaggttt tattactaat gtgactgatt ctgctgctaa ttttagttat | 1380 |
| ttagcagatg gtgggttagc tatttagat acgtcgggtg ccatagatgt ttttgttgta | 1440 |
| aagggcagct atggtcttaa ttattacaag gttaatcctt gtgaagatgt taaccaacag | 1500 |
| tttgtagtgt ctggtggcaa tatagttggc attcttactt ctagaaatga acaggttct | 1560 |
| gaacaggttg agaaccagtt ttatgttaag ttaaccaata gctcacatcg tcgcaggcgt | 1620 | tctattggcc aaaacgtaac aacttgccct tatgtta                                    1657

<210> SEQ ID NO 44
<211> LENGTH: 1643
<212> TYPE: DNA
<213> ORGANISM: artificial sequence
<220> FEATURE:
<223> OTHER INFORMATION: DNA of AY043312

<400> SEQUENCE: 44

```
atgttgggga agtcactgtt tttagtgacc attttgtgtg cactatgtag tgcaaatttg    60
tttgattctg ccaataatta tgtgtactac taccaaagtg cctttaggcc tccaaatgga   120
tggcatctgc aagggggtgc ttatgcagta gtgaattcta ctaatcatac taataatgcc   180
ggttctgcaa gtgggtgcac tgttggtgtt attaaggacg tctataatca agtgcggct    240
tccatagcta tgacagcacc tcttcagggt atggcttggt ctaagtcaca attttgtagt   300
gcacactgta acttttctga aattacagtt tttgtcacac attgttatag tagtggtaca   360
gggtcttgtc ctataacagg catgattgca cgtgatcata ttcgtatttc tgcaatgaaa   420
aatggttctt tattttataa tttaacagtt agcgtatcta ataccctaa ttttaagtct   480
tttcaatgtg ttaacaactt cacatctgtt tatttaaatg gtgatcttgt ttttacttcc   540
aacaaaacta ctgatgttac gtcagcaggt gtgtatttta aagcaggtgg acctgtaaat   600
tatagtatta tgaaagaatt taaggttctt gcttactttg ttaatggtac agcacaagat   660
gtaattttgt gtgacaattc ccccaagggt tgctagcct gtcaatataa cactggcaat   720
tttcggatg gcttttatcc ttttactaat agtactttag ttagggaaaa gttcattgtc   780
tatcgcgaaa gtagtgttaa tactactctg gcgttaacta atttcacttt tactaatgta   840
agtaatgcac agcctaatag tggtggtgtt catactttc atttatatca aacacaaaca   900
gctcagagtg ttattataa tttttaattg tcatttctga gtcagtttgt gtataaggca   960
agtgattta tgtatgggtc ttaccaccct agttgttctt ttagaccaga aaccattaat  1020
agtggttgt ggtttaattc cttgtcagtt tctcttactt acggaccct acagggaggg  1080
tgtaagcaat ctgtctttag tggtaaggca acgtgttgtt atgcctactc ttataatggc  1140
ccaagggcat gtaaaggtgt ttatttaggt gaattaagca cgagtttga atgtggattg  1200
ctggtttatg ttactaagag tgatggctct cgtatacaga ctagaacgga gcccttagta  1260
ttaacgcaac acaattataa taatattact ttagataagt gtgttgccta atatatat  1320
ggcagagtag gccaaggttt tattactaat gtgactgatt ctgctgctaa ttttagttat  1380
ttagcagatg gtgggttagc tattttagat acttcgggtg ccatagatgt ttttgttgta  1440
cagggcagct atggtcttaa ttattacaag gttaatcctt gtgaagatgt taaccaacag  1500
tttgtagtgt ctggtggcaa tatagttggc attcttactt ctagaaatga aacaggttct  1560
gaacaggttg agaaccagtt ttatgttaag ttagccaata gctcacatcg tcgcaggcgt  1620
tctattggcc aaaatgtaac aag                                         1643
```

<210> SEQ ID NO 45
<211> LENGTH: 5
<212> TYPE: PRT
<213> ORGANISM: artificial sequence
<220> FEATURE:
<223> OTHER INFORMATION: F fusion cleavage motif 4

<400> SEQUENCE: 45

-continued

```
Arg Arg Gln Lys Arg
1               5

<210> SEQ ID NO 46
<211> LENGTH: 5
<212> TYPE: PRT
<213> ORGANISM: artificial sequence
<220> FEATURE:
<223> OTHER INFORMATION: F fusion cleavage motif 5

<400> SEQUENCE: 46

Gly Arg Gln Ala Arg
1               5
```

HIGH RESOLUTION MELT GENOTYPING OF IBV, CSFV AND NDV

CROSS-REFERENCE TO RELATED APPLICATIONS

This application claims priority to U.S. provisional application 61/738,688 filed on Dec. 18, 2012.

FIELD OF THE INVENTION

The present invention relates to methods of differentiating and characterizing IBV, CSFV and NDV strains, and identifying new strains using high resolution melt technology. The present invention also provides primers and kits for use with such methods.

BACKGROUND OF THE INVENTION

The polymerase chain reaction (PCR) is a primer extension reaction that provides a method to amplify a specific DNA or polynucleotide in vitro, generating thousands to millions of copies of a particular DNA sequence. PCR is now a common and often indispensable technique used in medical and biological research labs for a variety of applications. These include DNA cloning for sequencing, DNA-based phylogeny, or functional analysis of genes; the diagnosis of hereditary diseases; the identification of genetic fingerprints; and the detection and diagnosis of infectious diseases. Some of the variations of the basic PCR include quantitative real-time PCR (qPCR or RT-PCR), allele-specific PCR, asymmetric PCR, hot start PCR, reverse transcription PCR, multiplex-PCR, nested-PCR, ligation-mediated PCR, Intersequence-specific PCR, Thermal asymmetric interlaced PCR and touchdown-PCR. These PCR variations provide wide variety of uses for different purposes. For example, single-nucleotide polymorphisms (SNPs) (single-base differences in DNA) can be identified by allele-specific PCR, qPCR can provide a very high degree of precision in determining the number of copies amplified in the PCR reactions (Bartlett et al., "A Short History of the Polymerase Chain Reaction", PCR Protocols, 2003).

Recently, High Resolution Melt (HRM) was added as a new molecular technique for high throughput mutation scanning (Zhou, L., et al., Clin. Chem. 51, 1770-1777, 2005). Mutation determination using FIRM is based on the dissociation of DNA, when exposed to an increasing temperature in the presence of fluorescent dyes interacting with double-stranded. DNA (see, for example U.S. Pat. No. 7,387,887; U.S. Pat. No. 7,582,429). There are numerous appropriate dyes disclosed in the art. The presence of a mutation leads to the formation of DNA heteroduplexes followed by a change in melting behavior. Thus, this "mutation scanning" technique detects the presence of sequence variations in target-gene derived PCR amplicons. In an HRM experiment, sample DNA is first amplified via real-time PCR in the presence of a High Resolution Melting Dye. Prominent examples of such dyes are disclosed in WO 2008/052742. After PCR, the successive melting experiment can be performed on the same Real Time Instrument, and analyzed with a respective Gene Scanning Software to identify sequence variants.

Classical swine fever (CSF), previously known as hog cholera is a highly contagious and multisystemic hemorrhagic disease affecting domestic and wild pigs that results in economic losses in the swine industry worldwide and is a notifiable disease to the Office International des Epizooties, according to the Terrestrial Animal Health Code (OIE, 2007). The causative agent is classical swine fever virus (CSFV) which is an enveloped, positive-sense, single stranded RNA virus, classified in the genus Pestivirus within the family Flaviviridae. At the genetic level, CSFV's can be divided into genotypes 1, 2 and 3, based on the partial sequences of the E2 and NS5B genes. Each genotype can be classified further into several sub-genotypes, referred to as 1.1, 1.2, and 1.3; 2.1, 2.2 and 2.3; and 3.1, 3.2, 3.3, and 3.4, respectively (Paton et al., Vet Microbiol. 73:137-157, 2000). In Asia, CSF epidemics are ubiquitous and genotypes 1, 2 and 3 have been isolated in several Asian countries.

CSFV can cause acute, sub-acute and chronic swine disease and poses a considerable threat to the swine industry worldwide causing severe economic losses. Control of CSF involves either eradication or vaccination, in which eradication is the preferred method of control in developed countries such as the Europian Union (EU) contributing to a significant amount of losses attributable to the slaughter of infected pigs. Vaccination on the other hand is the major control strategy in developing countries like China. The Hog Cholera Lapinized Virus (HCLV) (also known as the C strain) was developed in the mid-1950s and is widely used in China and many countries (Moorman et al., J Virol. 70:763-770, 1996). Massive vaccination with the HCLV vaccine makes it difficult to distinguish between wild-type and the HCLV-strain of CSFV in vaccinated swine herds (Van Oirshot, Vet Microbiol 96:367-384, 2003). Sub-clinical and asymptomatic infection with CSFV is universal (Moennig et al., Vet. J. 165, 11-20, 2003; Tu, Virus Res. 81, 29-37, 2001) making infections with wild-type CSFV not easily recognizable by farmers and veterinarians, and not detectable by general detection assays, such as virus isolation, antigen-capture ELISA, and fluorescent antibody tests.

Various diagnostic assays have been developed. However, they all have limitations. Virus isolation requires 6-12 days for confirmation of results; ELISA isn't very sensitive and often produces false negative results; real time PCR assays are faster and more sensitive but are limited by a high-risk of cross contamination and most importantly. None of these assays are able to distinguish between wild-type and the vaccines strains of CSFV. Previously, real-time RT-PCR assays for discriminating wild-type CSFV from the "Riems" vaccine-strain have been established in the EU (Leifer et al., J. Virol. Methods 158, 114-122, 2009; Leifer et al., J. Virol. Methods 166, 98-100, 2010; Leifer et al., J. Gen. Virol. 91, 2687-2697, 2010) and an assay for differentiating between wild-type and the "K-LOM' vaccine-strain CSFV in Korea was developed (Cho et al., Can J Vet Res 70:226-229, 2006). In China, a two-step real time RT-PCR assay to distinguish wild-type CSFV from the HCLV-strain vaccine based on nucleotide differences at the probe binding site and a one-step real time RT-PCR assay (wt-rRT-PCR) using a minor groove binding (MGB) probe for detection of mutations in wild-types have been described.

It is unlikely that a universal detection assay could be used in all countries because different CSFV vaccine strains have been administered in different countries, e.g., "Riems" in the EU, "K-LOM in Korea and "HCLV" in China. Therefore, there is a need to develop an assay that is affordable, easy to execute and easy to interpret results to distinguish between wild-type and vaccine-type for Classical Swine Fever.

Infectious Bronchitis (IB) is a disease prevalent in all countries within poultry industry, with the incidence approaching 100% in most locations. It is the most economically important disease. In young chicks, respiratory disease or nephritis lead to mortalities, reduced weight gain and condemnation at processing, whereas in chickens of laying age, the disease is subclinical and results in reduced egg production and aberrant eggs (Ignjatovic et al., Archives of Virology, 2006). IB outbreaks continue to occur in vaccinated flocks mainly because it is thought to be caused by different serotypes, subtypes or variant of IBV, that are generated by nucleotide point mutations, insertions, deletions, or recombination of S1 genes.

The causative agent, Infectious Bronchitis Virus (IBV) belongs to the Coronaviridae family. It is an enveloped positive-sense, single stranded RNA virus, with a genome size of 27.6 kb in length. The first 20 kb encode the viral RNA-dependent RNA polymerase and proteases. The whole genome has at least ten open reading frames (ORF) from 5' to 3' and are as follows: 5'-1a-1b-S(S1, S2)-3a,b,c(E)-M-5a, b-N-Poly(A)-3' encoding four structural proteins, including the spike glycoprotein (S), the membrane glycoprotein (M), the phosphorylated nucleocapsid protein (N) and the small membrane protein (E) (Mardani et al., Arch Virol. 155(10): 1581-6, 2010).

IBV was first reported in the USA in 1930 and has since been reported in most countries throughout the four continents of America (Johnson and Marquardt, Avian Dis. 19:82-90, 1975), Europe (Capua et al., Zentralbl Veterinarmed B. 41:83-89, 1994; Cavanagh and Davis, Arch Virol 130:471-476, 1993; Gough et al., Vet Rec. 130:493-494, 1992), Asia (Wang et al., Avian Dis 41:279-282, 1997) and Australia (Ignjatovic and McWaters, J Gen Virol. 72:2915-2922, 1991; Lohr, Avian Dis. 20:478-482, 1976). In Malaysia, little is known about the prevalence of the disease. The first report of IB disease was as early as 1967 where the disease was mild and vaccination unwarranted (Chong et al., Second symposium on Scientific and Technological Research in Malaysia and Singapore, pp 73-83, 1967; Aziz et al., The 8$^{th}$ Veterinary Association Malaysia Scientific Congress, 23-25 Aug. 1996, Ipoh, pp 76-78). Variants have been present since at least 1979 (Lohr, Proceedings of the 1$^{st}$ International Symposium on Infectious Bronchitis, E F Kaleta & U. Heffels—Redmann (Eds), pp 70-75, 1988; de Wit et al. Avian Pathology. 40(3):223-235, 2011) with reports of a more virulent strain causing nephrosis-nephritis syndrome that lead to high mortality was first reported in 1980 (Heng et al., Kajian Veterinar. 12:1-8, 1980; Aziz 1996). Recent publications related to IBD in Malaysia dates back to year 2000, 2004 and 2009 with clinical reports of variant nepropathogenic IBV strains since 1995 (Maizan, Proceeding 12$^{th}$ FAVA and 14$^{th}$ VAM congress, 28-28 Aug. 2002, pp 116; Yap M. L et al. Proceeding VAM Congress 1-4 Sep. 2000; Arshad et al. J. Vet. Malaysia. 14 (1&2): 322002; Balkis et al. Proceedings VAM Congress 2004, Zulperi et al. Virus Genes. 38:383-391, 2009).

Worldwide, several different serotypes and genotypes of IBVs have been identified and new variants are still emerging. One of these new variant is QX-like IB. IB-QX has been circulating and reported in China since 2004 (Liu & Kong, Avian pathology, 33:321-327, 2004). The virus which is identified as QX has been predominantly associated with various forms of renal pathology. Other researchers have also reported similar strains in China (Liu et al., J of Gen Virol, 86:719-725, 2005). In 2007, Cuiping et al. (Vet. Microbio., 122:71, 2007) confirmed the data presented by Liu et al. (2005) reporting the isolation of nephropathogenic strains from vaccinated and unvaccinated chicken flocks between 2003 and 2005. Similar findings have also been reported in Russia and other parts of Europe (Bochkov et al., Avian Pathology, 35:379-393, 2006; Landman et al., Proceedings of the 14$^{th}$ World Veterinary Poultry Congress, 22-26 Aug. 2005, Istanbul, Turkey, pp 369).

It is unlikely that a universal detection assay could be used in all countries because different IBV vaccine strains have been administered in different countries. Therefore, there is a need to develop an assay that is affordable, easy to execute and easy to interpret results to distinguish between wild-type and vaccine-type for Infectious Bronchitis (IB).

Despite intensive vaccination programs, Newcastle disease virus (NDV) remains a constant threat to commercial poultry farms worldwide. NDV is a member of the order Mononegavirales, family Paramyxoviridae and genus Avulavirus. It is an enveloped virus which has a negative-sense, nonsegmented single-stranded RNA genome consisting of 15, 586 nucleotides. Its genome comprises of six genes: nucleoprotein (NP), phosphoprotein (P), matrix protein (M), fusion glycoprotein (F), hemagglutinin-neuraminidase (FIN), glycoprotein and large polymerase protein (L). Of the six genes found in NDV, its two membrane proteins, the F protein and the HN protein are most important in determination of its virulence.

The establishment of real-time PCR methods in recent years has brought significant development to molecular diagnostics of various infectious agents and has rapidly cut-down the turn-around-time for disease diagnostics for quick and accurate results for veterinary practitioners in the field and farmers. Many PCR assays have been described for the Real Time PCR assay for NDV detection and genotype differentiation using several different TaqMan probes or SYBR green (Wise et al., J. Clin Microbiol, 42:329-338, 2004). Tan et al. (J. Virol Method, 160:149-156, 2009) described a SYBR Green 1 real-time PCR for the detection and differentiation of NDV genotypes, however this assay required different primer pairs for detecting the different NDV genotypes and relied heavily on the analysis of the melting peaks to differentiate the three genotypes of NDV. Although SYBR Green 1 assay is the most cost effective and easiest form of real-time PCR to establish compared to other real-time detection formats, however, the major disadvantage is that the dye molecules binds with any double-stranded DNA that is present in the reaction mixture including non-specific PCR products or primer-dimers. Therefore, there is room for improvement in the current molecular diagnostic methods for rapid and conclusive results of NDV testing.

SUMMARY OF THE INVENTION

The present invention relates to a method or process of characterizing a strain of IBV, CSFV or NDV comprising the steps of: a) generating a cDNA from the virus strain; b) exposing the cDNA to a primer pair comprising a forward primer and a reverse primer in a real-time polymerase chain reaction (PCR) to yield an amplicon, wherein the primer pair is specific to a gene or region of the viral genome; c) performing high resolution melt (HRM) curve analysis on a double-stranded product comprising the amplicon immediately after the real-time PCR; and d) analyzing and comparing the HRM curve thereby characterizing the virus strain. The gene for IBV may be the S1 gene. The gene for NDV may be the F, NP, P, M, FIN or L gene. The region for CSFV may be the four structural (C, Erns, E1 and E2) or eight non-structural protein (Npro, P7, NS2, NS3, NS4A, NS4B, NS5A and NS5B) region.

The present invention also provides primers and kits for use with such methods.

BRIEF DESCRIPTION OF THE DRAWINGS

The following detailed description, given by way of example, but not intended to limit the invention solely to the specific embodiments described, may be best understood in conjunction with the accompanying drawings, in which:

FIGS. 1A and 1B show a table identifying the SEQ ID NO assigned to each DNA and protein sequence.

FIG. 5 depicts the S1 sequence of IB-QX and blast results.

FIG. 6 shows the sequence comparison results.

FIG. 7 shows the sequence identity percentage of IBV strains.

FIG. 10 illustrates the sequence of LBK strain (CSFV) and the blast results.

FIG. 11 illustrates the sequence of VRI strain (CSFV) and the blast results.

FIG. 12 illustrates the sequence of Pestiffa strain (CSFV) and the blast results.

FIG. 13 illustrates the sequence of MVP strain (CSFV) and the blast results.

FIG. 14 illustrates the sequence of QYHC strain (CSFV) and the blast results.

FIG. 15 illustrates the sequence of ZBC strain (CSFV) and the blast results.

FIG. 16 illustrates the sequence of YSC strain (CSFV) and the blast results.

FIG. 17 depicts the HRM analysis of wild-type and vaccine-type of CSFV.

FIG. 18 depicts the HRM analysis of different vaccine-type CSFV strains.

FIG. 19 shows the nucleotide sequence alignment of wild-type CSFV and vaccine-type CSFV.

FIG. 20 shows the HRM analysis of NDV vaccine strains.

FIGS. 21A and 21B depict the nucleotide sequence alignment of NDV strains.

FIG. 22 illustrates the amino acid sequence alignment of NDV strains.

FIGS. 23A-23B show the sequence identity between NDV strains at nucleotide and amino acids levels.

FIG. 24 depicts the HRM analysis of NDV vaccine strains and wild type strains.

FIG. 25 depicts the HRM analysis of NDV strains to distinguish velogenic/mesogenic strains and lentogenic strains.

DETAILED DESCRIPTION

Figure 2:
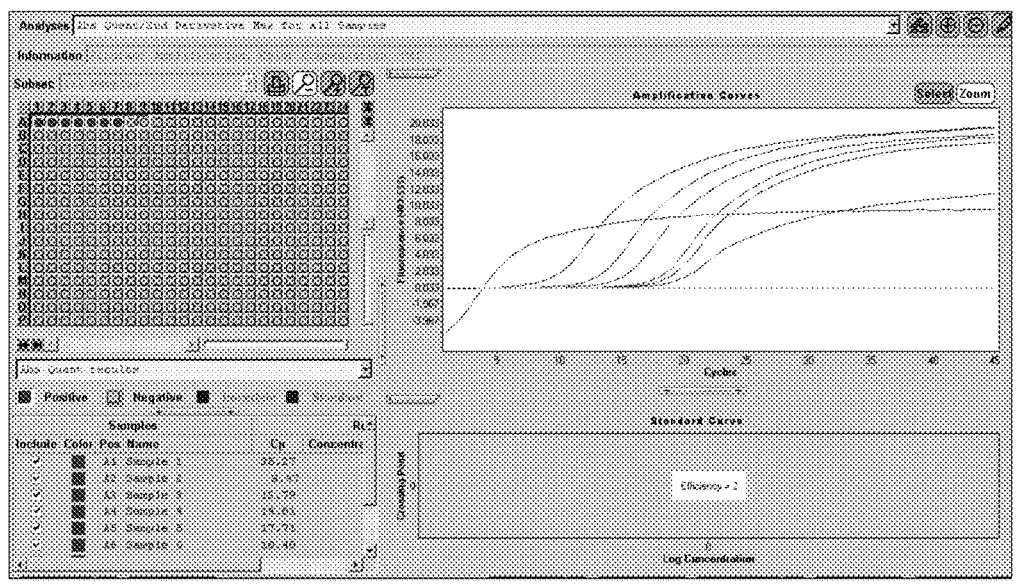
FIG. 2 depicts the sensitivity assay of real-time PCR for IBV.

It is noted that in this disclosure and particularly in the claims, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

For the purpose of interpreting the specification, the following definitions will apply and wherever appropriate, terms used in the singular will also include the plural and vice versa. The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), swine (e.g., pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

The terms "polypeptide" and "protein" are used interchangeably herein to refer to a polymer of consecutive amino acid residues.

The terms "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA", or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA). The term "genomic RA (nucleic acid)" as used herein includes RNA, mRNA, cRNA, DNA and cDNA.

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.; Pandher K et al.; Chung J Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term "heterologous DNA" as used herein refers to the DNA derived from a different organism, such as a different cell type or a different species from the recipient. The term also refers a DNA or fragment thereof on the same genome of the host DNA wherein the heterologous DNA is inserted into a region of the genome which is different from its original location.

The abbreviations for the various nucleic acid bases include guanine (G), thymine (T), adenine (A) and cytosine (C).

The term "PCR" refers to Polymerase Chain Reaction, a method for amplifying a single or a few copies of DNA exponentially by means of conventional a thermocycler. PCR could also refer to a conventional method for amplifying DNA copies that requires a gel electrophoresis step to view the amplified DNA.

"Real-time PCR" refers to an advanced PCR method that enables quantification of the DNA copies and monitoring of the amplification of DNA in real time by detecting the levels of fluorescence. The method does not require gel electrophoresis, utilizes less time and provides a more accurate result.

The term "amplicon" refers to a portion of polynucleotide that is to be amplified or multiplied using the polymerase chain reaction (PCR) methodology.

The term "High Resolution Melt (HRM)" refers to the technology for the detection of mutations, polymorphisms and genetic differences in double-stranded DNA samples. It is a relatively new method for DNA analysis that was introduced in 2002 as a result of a collaboration between academic (University of Utah, US) and the industry (Idaho Technology, US) (Reed et al. 2007). High Resolution Melting is used to characterize DNA samples according to their dissociation behavior as they transition from double stranded DNA (dsDNA) to single stranded DNA (ssDNA) with increasing temperature. The technique, subjects DNA samples to increasing temperatures and records the details of their dissociation from double-stranded (dsDNA) to single stranded form (ssDNA). The Instrument collects fluorescent signals with much greater optimal and thermal precision than previous methods to create new application possibilities.

HRM analysis is performed on double stranded DNA samples. Typically the polymerase chain reaction (PCR) is performed prior to HRM analysis to amplify the DNA region in which their mutation of interest lies. This region that is amplified is known as the amplicon. After the PCR, the HRM analysis begins. The process is a warming of the amplicon DNA from around 50° C. up to around 95° C. At some point during this process, the melting temperature of the amplicon is reached and the two strands of DNA separate or "melt" apart. The essence of HRM is to monitor this process in real-time. This is achieved by using a fluorescent dye which binds specifically to double-stranded DNA and when it is bound it fluoresces brightly. In the absence of double stranded DNA the dye has nothing to bind to and it only fluoresces at a low level. At the beginning of the HRM analysis there is a high level of fluorescence in the sample because of the billions of copies of the amplicon. But as the sample is heated up and the two strands of the DNA melt apart, presence of double stranded DNA decreases and thus fluorescence is reduced. The HRM machine records the process and plots the data as a graph known as a melt curve, showing the level of fluorescence vs. the temperature. The HRM machine has the ability to monitor this process in "high resolution" making it possible to accurately document difference in melting curves and therefore identify if a mutation is present or not.

The term "primer" as used herein refers to an oligonucleotide or short single-stranded nucleic acid which, upon hybridization with a complementary portion of another single-stranded molecule, acts as a starting point for initiation of polymerization mediated by an enzyme with DNA polymerase activity, such as in PCR.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The numbers of possible viral variants for a genome with N nucleotides in length are $4^N$ possible variants, because there are 4 different nucleotides. For example, there are $10^{180}$ different variants for a genome that is only 300 nucleotides in length. (Martin A. Nowak and Robert McCredie May *Virus Dynamics*, Oxford University Press). The genome sequence of an RNA virus population clusters around a consensus or average sequence, but each genome is different. A rare genome with a particular mutation may survive a selection event, and the mutation will then be found in all progeny genomes. The quasispecies theory predicts that viruses are not just a collection of random mutants, but an interactive group of variants. (Vincent Racaniello 2009).

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

The term "identity" with respect to sequences can refer to, for example, the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman). The sequence identity or sequence similarity of two amino acid sequences, or the sequence identity between two nucleotide sequences can be determined using Vector NTI software package (Invitrogen, 1600 Faraday Ave., Carlsbad, Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

IBV

One embodiment of the invention provides a process or method of characterizing a strain of IBV comprising the steps of: a) generating an IBV cDNA from the IBV strain isolated from an animal; b) exposing the cDNA to a primer pair comprising a forward primer and a reverse primer in a real-time polymerase chain reaction (PCR) to yield an amplicon, wherein the primer pair is specific to the S1 gene of IBV genome; c) performing high resolution melt (HRM) curve analysis on a double-stranded product comprising the amplicon immediately after the real-time PCR; and d) analyzing and comparing the HRM curve thereby characterizing the IBV strain.

The forward and reverse primers may be selected by aligning the polynucleotide sequences of the S1 gene of known IBV strains and comparing the conversed regions of the S1 gene. In one aspect of the embodiment, the forward primer has a polynucleotide sequence as set forth in SEQ ID NO:29 and the reverse primer has a polynucleotide sequence as set forth in SEQ ID NO:30.

S1 gene is known as the spiked (S) glycoprotein. The S1 subunit carries serotype-specific sequences and antigenic epitopes inducing virus neutralizing antibody. The different serotypes, subtypes or variant of IBV, were thought to be generated by nucleotide point mutations, insertions, deletions, or recombination of S1 genes, which were responsible for the outbreaks of IB in vaccinated chicken flocks (Zhou et al. J. Vet Med. B51, 147-152, 2004). Nucleotide sequencing of the S1 glycoprotein is commonly used to determine serotype differences among IBV strains (Kwon et al. Avian Dis. 1993).

The HRM curve analysis may be performed according to manufacturer's instructions. For example, several manufacturers provide instruments for the use of high-resolution DNA melt analysis such as Applied Biosystems (ABI), Bio-Rad, Cepheid, Corbett, Eppendorf, Idaho Technology, Roche and Stratagene. In addition, there are also several saturating dyes available in the market for carrying out the assay such as LCGreen® (Idaho Technology Inc.), Syto9® (Invitrogen, Carlsbad, Calif.), EvaGreen® (Bioturn) and LightCycler® 480 ResoLight Dye (Roche, Indianapolis, Ind.) (Vossen RHAM et al. Human Mutation 30 (6), 2009).

The real-time PCR may be carried out using the following parameters: a) initial denaturation at 95° C. for 3 seconds, b) denaturation at 95° C. for 1 minute, c) annealing at 55° C.

for 1 minute, d) extension at 72° C. for 1 minute, and e) repeating steps b)-d) for 45 times, followed by melting curve analysis (95° C. for 1 second, 65° C. for 15 seconds and 95° C. continuously) and cooling at 45° C. for 30 seconds.

The method of the present invention may be used to characterize and distinguish known IBV strains. The known IBV strains include, but are not limited to, 793/B strain, Massachusetts strain, QX-like strain, IBNC90 strain, D274 strain, Iowa strain, Arkansas strain, Holland 52 strain, Connecticut 46 strain, Beaudette US strain, California strain, Jilin strain, Holte strain, HK strain, D41 strain, DE072 strain, Spain/92/35 strain, Egypt/F/03 strain and other strains that are found worldwide.

The invention also provides for the identification of a novel strain of IBV wherein the IBV sequence does not align to any of the one or more IBV sequences with close homology. The method comprises the steps of: a) generating an IBV cDNA from the IBV strain isolated from an animal; b) exposing the cDNA to a primer pair comprising a forward primer and a reverse primer in a real-time polymerase chain reaction (PCR) to yield an amplicon, wherein the primer pair is specific to the S1 gene of IBV genome; c) performing high resolution melt (HRM) curve analysis on a double-stranded product comprising the amplicon immediately after the real-time PCR; d) analyzing and comparing the HRM curve; and e) identifying the novel IBV strain. The novel IBV strain thus identified by HRM curve analysis may be further characterized by sequencing the amplicon and aligning the IBV amplicon sequence with known IBV sequences. The novel IBV strain may have about 50%, about 60%, about 70%, about 75%, about 80%, about 85%, about 90%, about 91%, about 92%, about 93%, about 94%, about 95%, about 96%, about 97%, about 98%, or about 99% sequence identity with any known IBV sequence. The sequence may be nucleotide sequence or amino acid sequence (translation of the amplicon sequence).

Another aspect of the method embodiment provides a means for differentiation between infected and vaccinated (DIVA) animals. The method comprises the steps of: a) generating an IBV cDNA from the IBV strain isolated from an animal; b) exposing the cDNA to a primer pair comprising a forward primer and a reverse primer in a real-time polymerase chain reaction (PCR) to yield an amplicon, wherein the primer pair is specific to the S1 gene of IBV genome; c) performing high resolution melt (HRM) curve analysis on a double-stranded product comprising the amplicon immediately after the real-time PCR; and d) analyzing and comparing the HRM curve thereby determining whether the cDNA is derived from a vaccine-type strain or a strain that infected the animal.

One embodiment of the present invention provides an isolated polynucleotide or primer having the sequence as set forth in SEQ ID NO:29 or SEQ ID NO:30.

Another embodiment of the present invention provides a kit for detecting an IBV strain comprising: a) a primer pair comprising a forward primer having the sequence as set forth in SEQ ID NO: 29 and a reverse primer having the sequence as set forth in SEQ ID NO:30; and b) an instruction describing the parameters and conditions to perform real-time PCR.

CSFV

One embodiment of the invention provides a process or method of characterizing a strain of CSFV comprising the steps of: a) generating a CSFV cDNA from the CSFV strain isolated from an animal; b) exposing the cDNA to a primer pair comprising a forward primer and a reverse primer in a real-time polymerase chain reaction (PCR) to yield an amplicon, wherein the primer pair is specific to the NS5B or 3'NTR region of CSFV genome; c) performing high resolution melt (HRM) curve analysis on a double-stranded product comprising the amplicon immediately after the real-time PCR; and d) analyzing and comparing the HRM curve thereby characterizing the CSFV strain.

The forward and reverse primers may be selected by aligning the polynucleotide sequences of the NS5B or 3'NTR region of known CSFV strains and comparing the conversed regions of the NS5B or 3'NTR region. In one aspect of the embodiment, the forward primer has a polynucleotide sequence as set forth in SEQ ID NO:8 and the reverse primer has a polynucleotide sequence as set forth in SEQ ID NO:9.

NS5B is the RNA-dependent RNA polymerase gene. 3'NTR region is the 3' nontranslated region of the viral genome. Previous studies have shown (Pan et al., J Vet Diag Inv, 2008) notable T-rich insertions sites in the 3' NTR of the vaccine-type of CSFV which are absent in the wild-type of CSFV making both genes a suitable genetic marker for differentiation between wild-type and vaccine strains.

The HRM curve analysis may be performed according to manufacturer's instruction.

The real-time PCR may be carried out using the following parameters: a) initial denaturation at 95° C. for 3 seconds, b) denaturation at 95° C. for 1 minute, c) annealing at 55° C. for 1 minute, d) extension at 72° C. for 1 minute, and e) repeating steps b)-d) for 45 times, followed by melting curve analysis (95° C. for 1 second, 65° C. for 15 seconds and 95° C. continuously) and cooling at 45° C. for 30 seconds.

The method of the present invention may be used to characterize and distinguish known CSFV strains. The known CSFV strains include, but are not limited to, ALD strain, Chinese strain (C strain), GPE strain (Japanese strain), C/HVRI strain (from China, genotype 1.1), Riems strain (from China), Alfort 187 strain, Ames strain, Margarita strain, Baker strain, New York strain, Purdue 115 strain, Paderborn strain, Spreda strain, Oregon strain, Singer strain, Osloss strain, Moredun strai, Frijters strain and other strains that can be found in the literature.

The invention also provides for the identification of a novel strain of CSFV wherein the CSFV sequence does not align to any of the one or more CSFV sequences with close homology. The method comprises the steps of: a) generating a CSFV cDNA from the CSFV strain isolated from an animal; b) exposing the cDNA to a primer pair comprising a forward primer and a reverse primer in a real-time polymerase chain reaction (PCR) to yield an amplicon, wherein the primer pair is specific to the NS5B or 3'NTR region of CSFV genome; c) performing high resolution melt (HRM) curve analysis on a double-stranded product comprising the amplicon immediately after the real-time PCR; d) analyzing and comparing the HRM curve; and e) identifying a novel CSFV strain. The novel CSFV strain thus identified by HRM curve analysis may be further characterized by sequencing the amplicon and aligning the CSFV amplicon sequence with known CSFV sequences. The novel CSFV strain may have about 50%, about 60%, about 70%, about 75%, about 80%, about 85%, about 90%, about 91%, about 92%, about 93%, about 94%, about 95%, about 96%, about 97%, about 98%, or about 99% sequence identity with any known CSFV sequence. The sequence may be nucleotide sequence or amino acid sequence (translation of the amplicon sequence).

Another aspect of the method embodiment provides a means for differentiation between infected and vaccinated (DIVA) animals. The method comprises the steps of: a) generating a CSFV cDNA from the CSFV strain isolated from an animal; b) exposing the cDNA to a primer pair comprising a forward primer and a reverse primer in a real-time polymerase chain reaction (PCR) to yield an amplicon, wherein the primer pair is specific to the NS5B or 3'NTR region of CSFV genome; c) performing high resolution melt (HRM) curve analysis on a double-stranded product comprising the amplicon immediately after the real-time PCR; and c) analyzing and comparing the HRM curve thereby determining whether the cDNA is derived from a vaccine strain or a strain that infected the animal.

One embodiment of the present invention provides an isolated polynucleotide having the sequence as set forth in SEQ ID NO:8 or SEQ ID NO:9.

Another embodiment of the present invention provides a kit for detecting a CSFV strain comprising: a) a primer pair comprising a forward primer having the sequence as set forth in SEQ ID NO:8 and a reverse primer having the sequence as set forth in SEQ ID NO:9; and b) an instruction describing the parameters and conditions to perform real-time PCR.

NDV

One embodiment of the invention provides a process or method of characterizing a strain of NDV comprising the steps of: a) generating an NDV cDNA from the NDV strain isolated from an animal; b) exposing the cDNA to a primer pair comprising a forward primer and a reverse primer in a real-time polymerase chain reaction (PCR) to yield an amplicon, wherein the primer pair is specific to the F, NP, P, M, FIN or L gene of NDV genome; c) performing high resolution melt (HRM) curve analysis on a double-stranded product comprising the amplicon immediately after the real-time PCR; and d) analyzing and comparing the HRM curve thereby characterizing the NDV strain.

The forward and reverse primers may be selected by aligning the polynucleotide sequences of the F gene, or NP gene, or P gene, or M gene, or FIN gene, or L gene of known NDV strains respectively, and comparing the conversed regions of the F gene, or NP gene, or P gene, or M gene, or FIN gene, or L gene. In one aspect of the embodiment, the forward primer has a polynucleotide sequence as set forth in SEQ ID NO:17 or 31 and the reverse primer has a polynucleotide sequence as set forth in SEQ ID NO:18 or 32.

The fusion (F) protein is responsible in mediating fusion of the viral envelope with cellular membranes and the haemagglutinin-neuraminidase (FIN) protein is involved in cell attachment and release (Phillips, et al., Arch. Virol, 143:1993-2002, 1998; Tan et al., Arch. Virol, 155:63-70, 2010). NDV strains are classified into 3 genotypes, highly virulent (velogenic), intermediate (mesogenic) or nonvirulent (lentogenic). Traditionally, NDV genotypes are most commonly distinguished by sequencing and amino acid sequences analysis. The consensus sequence of the F protein cleavage site of velogenic and mesogenic strains is 112(R/K)RQ(R/K)RF117; the consensus sequence of the lentogenic F cleavage site is 112(G/E)(K/R)Q(G/E)RL117. A recent finding documented (Samal S et al. J. Gen. Virol. 2011) that a change of glutamine to basic residue arginine (R) at position 114 of the F cleavage site reduced the viral replication and attenuated the virus pathogenicity. The paper also reported that the pathogenicity was further reduced when isoleucine (I) at position 118 was substituted by valine.

The HRM curve analysis may be performed according to manufacturer's instruction.

The real-time PCR may be carried out using the following parameters: a) initial denaturation at 95° C. for 3 seconds, b) denaturation at 95° C. for 1 minute, c) annealing at 60° C. for 1 minute, d) extension at 72° C. for 1 minute, and e) repeating steps b)-d) for 45 times, followed by melting curve analysis (95° C. for 1 second, 65° C. for 15 seconds and 95° C. continuously) and cooling at 45° C. for 30 seconds.

The method of the present invention may be used to characterize and distinguish known NDV strains. The known NDV strains include, but are not limited to, Avinew strain, LaSota strain, MVP-Mukteswar strain, ND-B1 strain, Korea Dalguban strain, Herts 33 strain, Essex '70 strain, 135/93 strain, 617/83 strain, 34/90 strain, Beaudette C strain, D26 strain, MC110 strain, 1154/98 strain and others that can are documented in the literature.

The invention also provides for the identification of a novel strain of NDV wherein the NDV sequence does not align to any of the one or more NDV sequences with close homology. The method comprises the steps of: a) generating an NDV cDNA from the NDV strain isolated from an animal; b) exposing the cDNA to a primer pair comprising a forward and a reverse primer in a real-time polymerase chain reaction (PCR) to yield an amplicon, wherein the primer pair is specific to the F, NP, P, M, FIN or L gene of NDV genome; c) performing high resolution melt (HRM) curve analysis on a double-stranded product comprising the amplicon immediately after the real-time PCR; d) analyzing and comparing the HRM curve; and e) identifying a novel NDV strain. The novel NDV strain thus identified by HRM curve analysis may be further characterized by sequencing the amplicon and aligning the NDV amplicon sequence with known NDV sequences. The novel NDV strain may have less than 50%, less than 60%, less than 70%, less than 75%, less than 80%, less than 85%, less than 90%, less than 91%, less than 92%, less than 93%, less than 94%, less than 95%, less than 96%, less than 97%, less than 98%, or less than 99% sequence identity with any known NDV sequence. The sequence may be nucleotide sequence. The sequence may also be amino acid sequence (translation of the amplicon sequence).

Another aspect of the method embodiment provides a means for differentiation between infected and vaccinated (DIVA) animals. The method comprises the steps of: a) generating an NDV cDNA from the NDV strain isolated from an animal; b) exposing the cDNA to a primer pair comprising a forward and a reverse primer in a real-time polymerase chain reaction (PCR) to yield an amplicon, wherein the primer pair is specific to the F, NP, P, M, FIN or L gene of NDV genome; c) performing high resolution melt (HRM) curve analysis on a double-stranded product comprising the amplicon immediately after the real-time PCR; and d) analyzing and comparing the HRM curve thereby determining whether the cDNA is derived from a vaccine strain or a strain that infected the animal.

One embodiment of the present invention provides an isolated polynucleotide having the sequence as set forth in SEQ ID NO:17, 18, 31 or 32.

Another embodiment of the present invention provides a kit for detecting an NDV strain comprising: a) a primer pair comprising a forward primer having the sequence as set forth in SEQ ID NO:17 and a reverse primer having the sequence as set forth in SEQ ID NO:18; or a primer pair comprising a forward primer having the sequence as set forth in SEQ ID NO:31 and a reverse primer having the sequence as set forth in SEQ ID NO:32; and b) an instruction describing the parameters and conditions to perform real-time PCR.

Immunogenic Compositions and Vaccines

The present invention also provides isolating the novel stain of IBV, CSFV or NDV. Methods for isolating novel viruses are well known to one of skill in the art (see, e.g., protocols in Ausubel et al., Current Protocols in Molecular Biology, 1991, John Wiley and Sons, New York; Sambrook et al., Molecular Cloning: A laboratory manual, 1989, Cold Spring Harbor Laboratory, Cold Spring Harbor, N.Y.).

Accordingly, the invention further comprehends immunogenic compositions or vaccines comprising the novel IBV, CSFV or NDV. The immunogenic compositions or vaccines according to the invention can include the virus culture or preparation (e.g., inactivated or attenuated), or antigen or immunogen of the virus. The immunogenic composition or vaccines of the invention may further comprise one or more pharmaceutically or veterinarily acceptable carriers, vehicles, adjuvants, or excipients.

The pharmaceutically or veterinarily acceptable carriers, vehicles, adjuvants, or excipients are well known to the one skilled in the art. For example, a pharmaceutically or veterinarily acceptable carrier, vehicle, adjuvant, or excipient can be a 0.9% NaCl (e.g., saline) solution or a phosphate buffer. Other pharmaceutically or veterinarily acceptable carrier, vehicle, adjuvant, or excipients that can be used for methods of this invention include, but are not limited to, poly-(L-glutamate) or polyvinylpyrrolidone. The pharmaceutically or veterinarily acceptable carrier, vehicle, adjuvant, or excipients may be any compound or combination of compounds facilitating the administration of the vector (or protein expressed from an inventive vector in vitro); advantageously, the carrier, vehicle, or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The pharmaceutically or veterinarily acceptable carrier, excipient, vehicle or adjuvant may be a water-in-oil emulsion. Examples of suitable water-in-oil emulsions include oil-based water-in-oil vaccine emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly) ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084, e.g., Example 8. In some embodiments, the antigen-containing aqueous phase comprises a saline solution comprising one or more buffering agents. An example of a suitable buffering solution is phosphate buffered saline. In one embodiment, the water-in-oil emulsion may be a water/oil/water (W/O/W) triple emulsion (U.S. Pat. No. 6,358,500). Examples of other suitable emulsions are described in U.S. Pat. No. 7,371,395.

The immunogenic compositions and vaccines according to the invention may comprise or consist essentially of one or more pharmaceutically or veterinarily acceptable carrier, excipient, vehicle, or adjuvant. Suitable carriers or adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The invention will now be further described by way of the following non-limiting examples.

EXAMPLES

The standard molecular biology techniques described by J. Sambrook et al. (Molecular Cloning: A Laboratory Manual, 2nd Edition, Cold Spring Harbor Laboratory, Cold Spring Harbor, N.Y., 1989) were used in the experiments.

Example 1 HRM Analysis of IBV

A total of 56 samples from different farms and locations were submitted to Vet Food Agro Diagnostics (M) Sdn. Bhd. for routine IBV diagnosis in 2011. The organ samples received ranged from lungs, kidney, caecal tonsils, trachea and pooled organs. These samples were suspected to harbor the IB virus and were sent for detection of the specified virus and confirmation. All these samples were homogenized and tested by reverse transcriptase PCR and real time PCR in this study.

Nucleic acid extraction was carried out using Trizol LS reagent (Invitrogen, USA) according to the standard manufacturer's protocol.
Multiplex Reverse Transcriptase (RT) PCR for the Detection of Mass and 793/B A multiplex, based on S1 gene sequences, from a previously described method (Cavanagh et al., Avian Pathology, 28:593-605, 1999) was employed for the detection and differentiation of two types of IBV: 793/B and Massachusetts. The oligonucleotide (primer) sequences were as follow: XCE2-$^a$: CTCTATAAACACCCTTACA (SEQ ID NO:1); XCE2-$^b$: CACTGGTAATTTTTCAGATGG (SEQ ID NO:2) (RT PCR step); XCE3-: CAGATTGCTTA-CAACCACC (SEQ ID NO:3); BCE1+: AGTAGTTTTGT-GTATAAACCA (SEQ ID NO:4); DCE1+: ATACAAT-TATATCAAACCAGC (SEQ ID NO:5); MCE1+: AATACTACTTTTACGTTACAC (SEQ ID NO:6) (Nested step) (Adzhar et al., Avian Pathology, 25:817-836, 1996; Cavanagh et al., Avian Pathology, 28:593-605, 1999). The reaction conditions were Reverse Transcriptase step at 45° C. for 1 hour, 72° C. for 10 minutes, followed by initial denaturation step at 94° C. for 5 minutes. The amplification steps were 94° C. for 1 minute, 50° C. for 1.5 minutes, 72° C. for 2 minutes repeated for 30 times, followed by final extension at 72° C. for 2 minutes. The nested step was carried out with the following conditions: Initial Denaturation at 94° C. for 5 minutes, Amplification at 94° C. for 1 minute, 50° C. for 1.5 minutes and 72° C. for 2 minutes for a total of 30 times, followed by final extension at 72° C. for 10 minutes and hold at 4° C.

One-Step RT-qPCR for the Detection of IB-QX

Real time PCR was carried out with a reaction volume of 10 μL of SensiFAST SYBR green master mix, 0.8 μl of 20 pmol forward primer (CTTATGCAGTAGTCAA) (SEQ ID NO:29) and reverse primer (CACGTGGAATCATGCCT-GTTAT) (SEQ ID NO:30), 0.2 μL of reverse transcriptase enzyme, 0.4 μL of RNAse inhibitor, 4 μL of template and 3.8 μL of ddH$_2$O. The real time PCR reactions were carried out in a LightCycler 480 real time PCR instrument (Roche, Germany). The reaction conditions were Reverse Transciptase step at 45° C. for 10 min followed by initial denaturation step at 94° C. for 2 minutes. The amplification steps were 94° C. for 5 seconds, 50° C. for 10 seconds and elongation at 72° C. for 5 seconds. The melting curve analysis profile were 95° C. for 3 sec, 58° C. for 1 min and 95° C. continuous, followed by cooling at 45° C. for 30 seconds.

HRM Assay to Differentiate IBN-C90 and IB-QX

The assay was established by using the same primer pair as described above (SEQ ID NO:29 and SEQ ID NO:30) that amplify the hyper-variable region of the S1 gene of IB. The assay consisted of 1 μl of the highly saturated fluorescent dye (EvaGreen), 12.5 μl master mix (Sensimix, Bioline), 2 μl of 25 mM MgCl2, 0.5 μl of the primer pair, template and PCR grade water. The samples were loaded into the 384-well microwell plate and subjected to PCR amplification in a real time PCR machine (LightCycler 480, Roche). The thermal cycling reactions consisted of an initial denaturation (3 sec at 95° C.). The amplification consisted of denaturation (1 min at 95° C.), annealing (1 min at 48° C.) and extension (1 min at 72° C.). The PCR was immediately followed by high resolution melting curve analysis. The differentiations of the samples were achieved by using the known positive controls and in comparison with their melting profiles.

Validation

Sensitivity of the RT Real Time PCR

All concentrations of reference materials were measured by a UV Spectrophotometer. Concentrations were standardized to 10 pg/μl. An end-point dilution (ten-fold serial dilution) was used until the assay could no longer detect the target organism (no detection signals).

Specificity

The specificity of the test was conducted by testing the protocol against 5 other organisms (IBV 793/B, IBV Mass, IBD, NDV, CAV, Reovirus).

Sequencing

Samples for sequencing (direct sequencing) were sent to a commercial sequencing facility. PCR clean up and gel purification was done based on manufacturer's protocol (Analytik Jena, Germany). Results obtained were analyzed by BLAST (Basic Local Alignment Search Tool) for confirmation of the reference material.

Results

Fifteen out of the fifty-six (26.8%) samples tested were positive for 793/B strain, nine out of fifty-six (16%) were positive for Massachusetts strain; thirty-two out of fifty-six (57%) were positive for QX-like strain; eighteen out of the fifty-six cases (32%) which were previously reported as negative for IB were found to be positive for IB-QX when re-tested.

Validation of the Real Time PCR Assay for the Specific Detection of IB-QX

Sensitivity

FIG. 2 illustrates the sensitivity of the assay with an initial concentration of 10 ng/μL. Based on the threshold derived at 18.48 at the final dilution level, it is estimated that the test is highly sensitive and may be able to detect the virus at concentrations as low as 100 ag.

Amplification Curve—IB-QX (Specificity)

Figure 3:
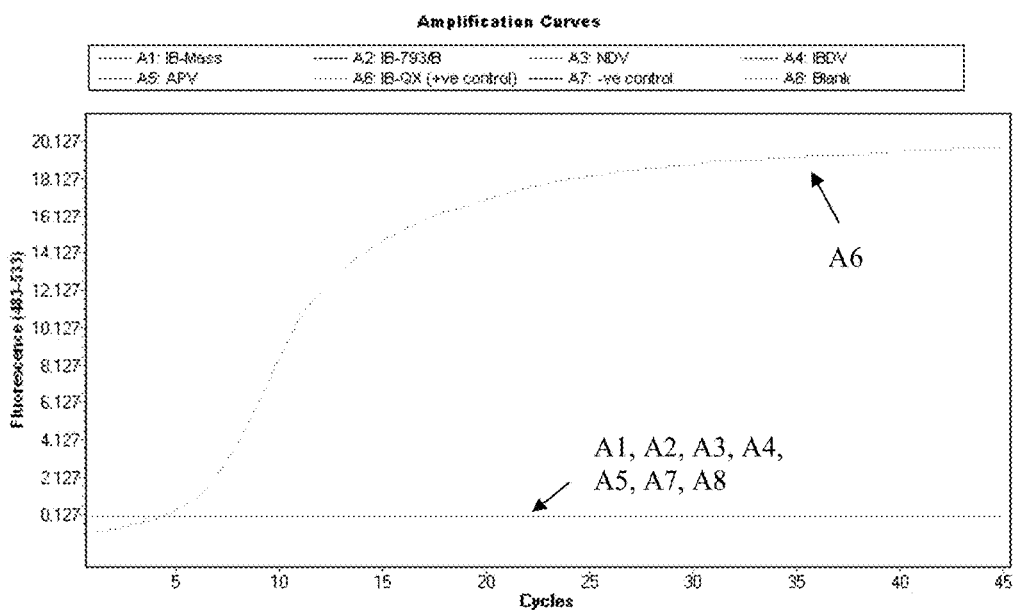
FIG. 3 depicts the amplification curve of IB-QX to show specificity.

The specificity of the assay was tested with other closely related organisms such as IB-Massachusetts, IB-793/B, NDV, IBV and Avian PneumoVirus (APV). FIG. 3 illustrates the amplification curves derived from the specificity assay.

Melting Peak (Tm)—IB-QX (Specificity)

Figure 4:
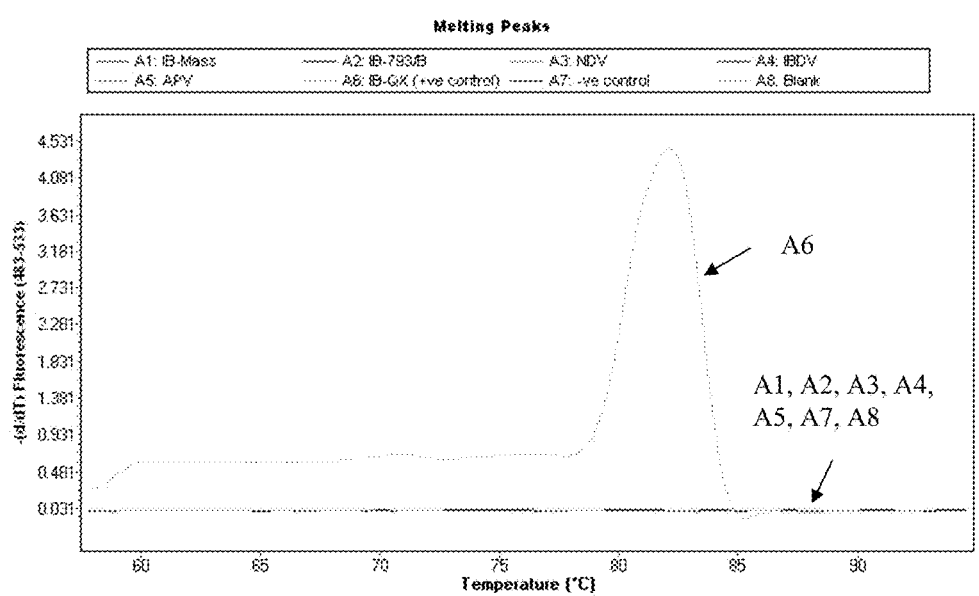
FIG. 4 shows the melting peak of IB-QX to show specificity.

The specificity of the assay was tested with other closely related organisms such as IB-Massachusetts, IB-793/B, NDV, IBV and APV. FIG. 4 illustrates the melting peak derived from the specificity assay.

Confirmation by Sequencing Analysis

The PCR product representing S1 gene of IB-QX strain was sequenced and the sequence is shown in FIG. 5 (SEQ ID NO:7). The sequence was used to BLAST against GenBank database (NCBI). The screen shot of the BLAST results and tabulated nucleotide sequence scores as determined by the BLAST analysis are shown in FIG. 5. The BLAST analysis confirms that the melting peaks and bands obtained from the PCR analysis is IB-QX.

Comparison of the previously reported nepropathogenic IB (MH5365/95) with sequences in Genbank was done and the screen shot of the BLAST results and tabulated nucleotide sequence scores as determined by the BLAST analysis are shown in FIG. 6. The BLAST analysis confirms that the nephropathogenic strain isolated in 1995 is closely related to recent IB strains found in Thailand. FIG. 7 shows the sequence identity matrix of the 7 closely related sequences to the previously isolated IB case in Malaysia (MH5365/95 and v9/04).

Figure 8:
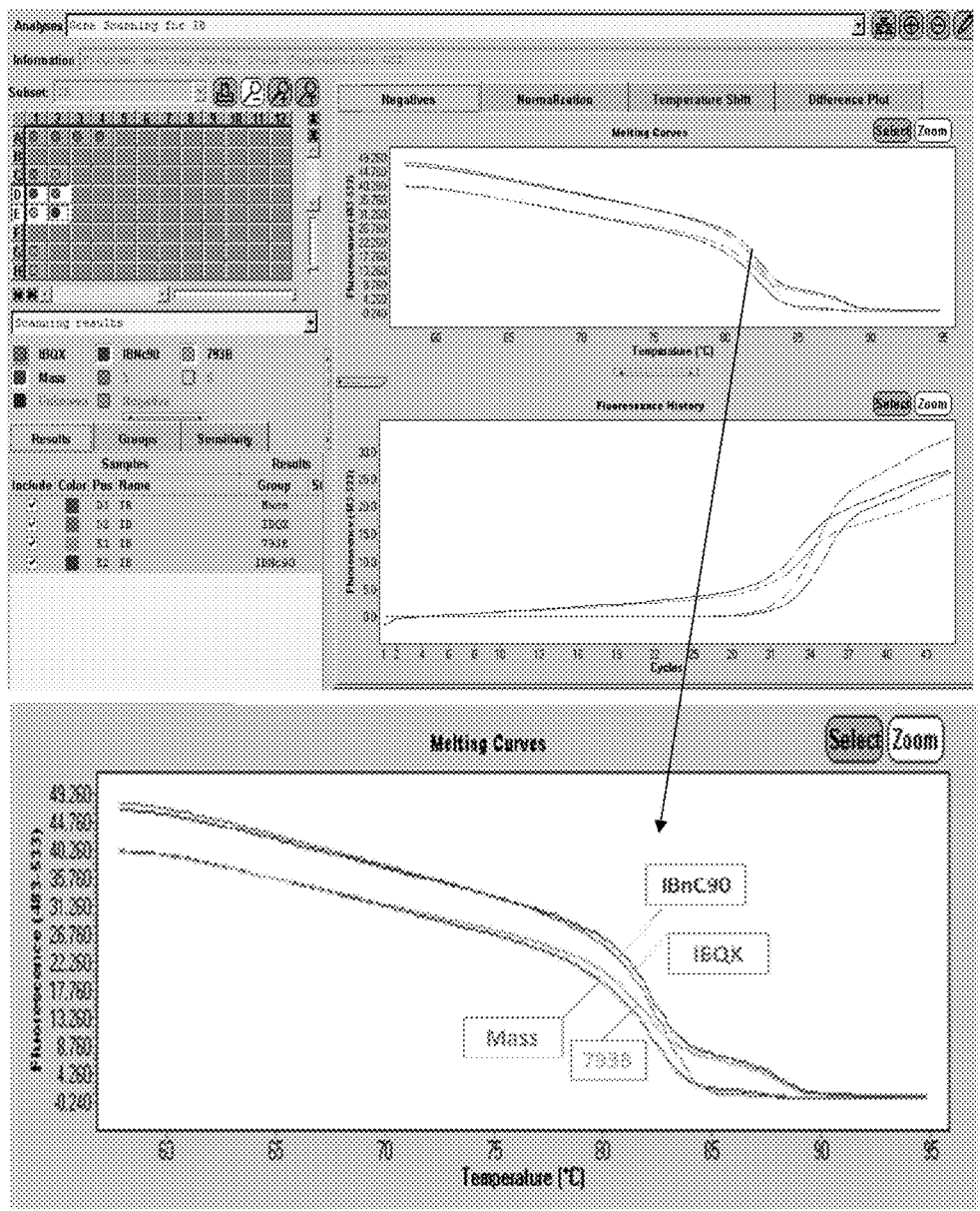
FIG. 8 depicts the HRM analysis of IB-QX, IBnC90, Mass and 793/B strains.
Figure 9:
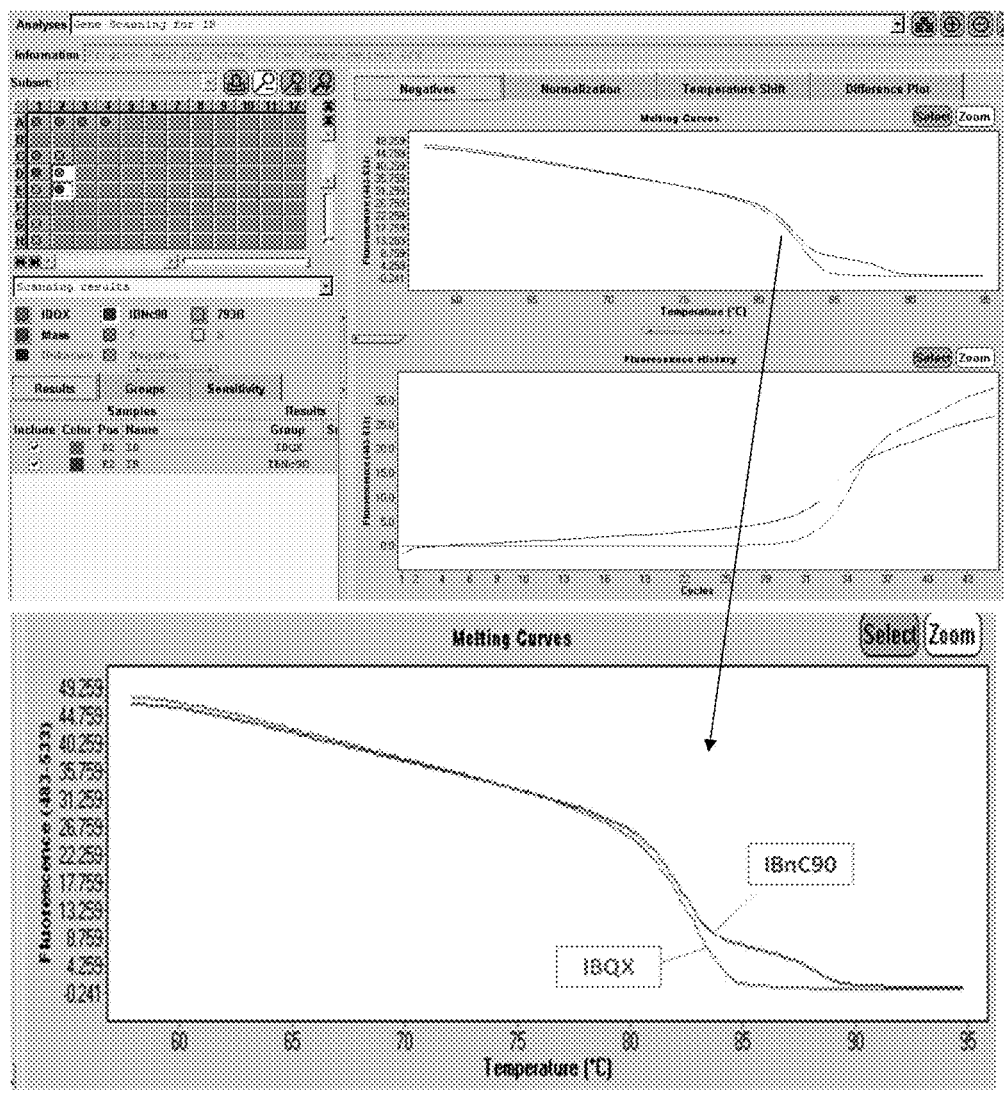
FIG. 9 depicts the HRM analysis of IB-QX and IBnC90 strains.

FIG. 8 illustrates the HRM analysis to compare IB-QX, IBnC90, Mass and 793/B. FIG. 9 depicts the HRM analysis to compare/detect IB-QX and IBnC90.

IB-QX was successfully detected from the retained archived samples. 26.8% samples tested were positive for the variant strain—793/B strain, 16% were positive for the classic IB—Massachusetts; while 57% tested were positive for the new QX-like strain that has been circulating since 2004. 18 out of the 56 cases (32%) which were previously reported as negative for IB were found to be positive for IB-QX when re-tested. Due to lack of controls and lack of detection method for the QX strain, some of the 2011 IB cases were falsely reported as negative. Springing from there, a method was successfully modified from a previously published paper to accurately detect IB-QX (H. J. Geerligs et al., Avian Pathology, 40(1):93-102, 2011). The changes were made to modify the method from 3 hours conventional PCR to a 54 minutes real time PCR assay that could detect nucleic acid as little as 100 ag/μl. However, although the method is highly sensitive and specific, it is foreseen that the new QX detection assay has its limitations as it would not be able to detect other strains that may be present in poultry specimens, not be able to detect several different types of IB strains simultaneously As the results show, a high resolution melt assay (HRM) that employs gene scanning software is able to distinguish single nucleotide differences based on the hyper variable region of the S1 gene to concurrently detect 4 strains (793/B, Mass, QX and IBnC90) as shown in FIG. 8. The possibility of conducting the assay to compare two strains (QX and IBnC90) is also shown in FIG. 9.

Example 2 HRM Analysis of CSFV

In this study, various wild-type and vaccine-type CSFV strains were used. The wild-type strains included archived retained sample labeled as LBK and archived retained sample labeled as VRI (derived from challenged pigs-pigs with the LBK virus). The vaccine type strains included Pestiffa (live vaccine—C strain), MVP (live vaccine—GPE strain), QYHC (live vaccine), ZBC (live vaccine), YST (live vaccine), YSC (live vaccine).

Reverse Transcriptase Step

The reverse transcriptase step to generate the complimentary DNA of the CSF was carried out as follow: the assay was established by using primer sets that amplify the NS5B and 3'NTR regions of the CSFV sequences encompassing the T-rich insertion site that is unique to the lapinized CSFV vaccine strains. The primer sets are as follows: forward primer 5'-GTAGCAAGACTGGRAAYAGGTA-3' (SEQ ID NO:8) (Y=C or T, R=A or G) and reverse primer 5'-AAAGTGCTGTTAAAAATGAGTG-3' (SEQ ID NO:9) (Pan et al., 2008). The real time PCR mixtures consisted of 10 µl of SYBR green master mix (Bioline), 1.6 µl of the respective primer sets (10 µM), 0.2 ul of reverse transcriptase enzyme, 0.4 µl of RNAse Inhibitor and 3.8 µl of PCR grade water to make up the final volume of 20 µl per reaction. The PCR mixtures were subjected to real time PCR amplification in a 384-well microplate in the LC480 Real Time PCR instrument (LC 480, Roche).

HRM Curve Analysis of CSFV to Distinguish its Genotype

The samples were subjected to the HRM assay. The assay consisted of 1 µl of the highly saturated fluorescent dye (EvaGreen), 12.5 µl of HRM master mix (Sensimix Bioline), 2 µl of 25 mM MgCl2, 1 µl of the primer pair (5 µM), 2 µl of template and PCR grade water. The same primer pairs (SEQ ID NO:8 and SEQ ID NO:9) as used for the reverse tranceriptase step were used for the HRM assay. The uniqueness of the primer pairs is that it would generate an amplicon size of 367 bp for wild-type strains and 379 bp for vaccine-type strains making it very obvious to accurately distinguish between the wild-type and vaccine-type strains. The samples were loaded into the 384-well microwell plate and subjected to PCR amplification in a real time PCR machine (Light-Cycler 480, Roche). The thermal cycling reactions consisted of an initial denaturation (3 s at 95° C.). The amplification consisted of denaturation (1 min at 95° C.), annealing (1 min at 55° C.) and extension (1 min at 72° C.). The PCR was immediately followed by high resolution melting curve analysis. The differentiation of the genotypes was achieved by using the known positive controls and comparing their melting profiles.

Nucleotide Sequence Analysis

Sequence assembly and nucleotide sequence analysis were done using various Bioinformatics software such as ClustalX/W for multiple sequence alignment and Bioedit 7.0 (Sequence Alignment Editor version 7.0.5.2, Tom Hall, US). All sequences were subjected to BLAST analysis (blastn) against Genbank database (NCBI).

The LBK sequence (SEQ ID NO:10) and blast results are shown in FIG. 10. The PCR generated a 367 bp PCR product. Sequencing of LBK and blast results confirmed that LBK is a wild-type ALD strain.

The VRI sequence (SEQ ID NO:11) and the blast results are shown in FIG. 11. The PCR generated a 367 bp PCR product. Sequencing of VRI and blast results confirmed that VRI is a wild-type ALD strain.

The Pestiffa sequence (SEQ ID NO:12) and the blast results are shown in FIG. 12. The PCR generated a 379 bp PCR product. Sequencing of Pestiffa and blast results confirmed that it belongs to the vaccine strain, "Chinese" strain (C strain).

The MVP sequence (SEQ ID NO:13) and the blast results are shown in FIG. 13. The PCR generated a 379 bp PCR product. Sequencing of MVP and blast results confirmed that it belongs to the vaccine strain GPE, Japanese strain.

The QYHC sequence (SEQ ID NO:14) and the blast results are shown in FIG. 14. The PCR generated a 379 bp PCR product. Sequencing of QYHC and blast results confirmed that it belongs to the vaccine strain C/HVRI, from China, genotype 1.1.

The ZBC sequence (SEQ ID NO:15) and the blast results are shown in FIG. 15. The PCR generated a 379 bp PCR product. Sequencing of ZBC and blast results confirmed that it belongs to the vaccine strain C/HVRI, from China, genotype 1.1.

The YSC sequence (SEQ ID NO:16) and the blast results are shown in FIG. 16. The PCR generated a 379 bp PCR product. Sequencing of YSC and blast results confirmed that it belongs to the vaccine strain Riems, Chinese strain.

Results of HRM Curve Analysis of CSFV

The HRM assay was able to differentiate and group the vaccine-type (Pestiffa) and wild-type strains (LBK/VRI) (FIG. 17). A portion of the nucleotide sequence alignment shows the T-rich insertion in the vaccine-type and the deletions in the wild-type that enables the differentiation of the wild-type (LBK) and vaccine-type (Pestiffa) strains respectively (FIG. 17). The HRM assay was also able to differentiate and group the different vaccine-types (FIG. 18). A portion of the nucleotide sequence alignment of the wild-type (LBK) and the vaccine-types (Pestiffa, ZBC, YSC, QYHC and MVP) shows the varying sizes of the T-rich insertions in the vaccine-type and the deletions in the wild-type that enables the differentiation of the wild-type (LBK/VRI) and vaccine-type (Pestiffa) strains (FIG. 19).

Validation—Sensitivity and Specificity

The sensitivity of the assay was carried out by a serial dilution with an initial virus concentration of 10 ng/µL. Based on the threshold derived, it is estimated that the test is sensitive and is able to detect the target at concentrations as low as 100 ag. The specificity of the assay was tested with other swine viruses such as PCV2, PRRS, Parvovirus, SIV. Our analysis showed that the primer pairs did not amplify these other viruses and was found specific for the detection of CSFV.

The study shows that the assay is unique as the primer pair is able to generate different amplicon sizes for wild-type (367 bp) and vaccine-type (379 bp). The analysis by high resolution melting combined with nucleic acid sequencing confirms that the assay is able to rapidly detect and differentiate wild-type and vaccine-type strains.

Example 3 HRM Analysis of NDV

Organ samples consisting of trachea, brain, bone marrow, lungs, kidney, spleen, intestine, lymph nodes, caecal tonsil, bursa, proventriculus, liver, heart, thymus and pooled organs were collected from 14 poultry farms in Malaysia from animals displaying classic NDV clinical signs. The organ samples were subjected to nucleic acid extraction by using the Trizol LS reagent following the standard manufacturer's protocol. The real time PCR was established with modifications from a method previously described. The real time PCR mixtures consisted of 10 ul of SYBR green master mix, the respective primer sets and PCR grade water to make up the final volume of 20 ul per reaction. The PCR mixtures were subjected to real time PCR amplification in a 384-well microplate in the LC480 Real Time PCR instrument (LC 480, Roche). The melting peaks and melting curves were observed by using the Absolute Quant Software provided with the instrument.

Sequencing, Amino Acid Sequence Analysis, Phylogenetic Construction

Primer sets (5'-ATG GGCY CCA GAY CTT CTA C-3' (forward) (SEQ ID NO:17), 5'-CTG CCA CTG CTA GTT GTG ATA ATC C-3' (reverse)(SEQ ID NO:18) were used for amplifying the fusion protein gene of Newcastle Disease Virus. The PCR protocol was established with modifications from the method previously described (Berhanu et al., Virol J., 7:183, 2010). The real time PCR mixtures consisted of 10 µl of SYBR green master mix, the respective primer sets and PCR grade water to make up the final volume of 20 µl per reaction. The PCR mixtures were subjected to real time PCR amplification in a 384-well microplate in the LC480 Real Time PCR instrument (LC 480, Roche). The melting peaks and melting curves were observed by using the Absolute Quant Software provided with the instrument. The thermal profile was set at: pre-denaturation at 95° C. for 3 seconds, followed by 45 cycles of 1 minute denaturation at 95° C., 1 minute for annealing at 56° C. and 1 minute for elongation at 72° C. Melting curve analysis was performed to measure the specificity of PCR product. After PCR cycling, samples were heated to 95° C. for 1 second and 65° C. for 15 seconds and then heated to 95° C. continuously at a linear transition rate. The real time PCR cycle was run using the LightCycler 480 (Roche®).

The same primer sets were used for sequencing. The PCR products of the expected amplicon sizes were purified by using the PCR clean-up gel extraction kit according to the manufacturer's protocol with slight modifications (Analytik Jena, Germany). Sequencing of the fusion protein gene of NDV was done in a commercial sequencing facility using the BigDye Terminator v3.1 cycle sequencing kit. In order to confirm that all positive cases were true Newcastle disease virus, a Basic Local Alignment Search Tool (BLAST) search of the sequence was done in the Genbank database. The sequence editing and assembly were done by using BioEdit Sequence Alignment Editor version 7.0.5.2 (Tom Hall, US). Sequence alignments were done by using ClustalX. The phylogenetic tree was constructed by using the distance-based neighbor joining method by using Mega 5 software (Biodesign Institute, Tempe, Ariz.) and evaluated using the bootstrapping method calculated on 1000 repeats of the alignment. The sequence identity matrix was generated with BioEdit Sequence Alignment Editor version 7.0.5.2 (Tom Hall, US).

DIVA (Differentiation of Infected Versus Vaccine) Assay

Positive NDV samples were subjected to the DIVA assay. The DIVA assay was established by using primer sets: forward primer 5'-CTG CCA CTG CTA GTT GIG ATA ATC C-3' (SEQ ID NO:31, I=inosine), reverse primer 5'-CCT TGG TGA ITC TAT CCG IAG G-3' (SEQ ID NO:32, I=inosine) that amplify the hyper-variable region of the fusion protein gene of NDV. The assay consisted of 10 µl of the highly saturated fluorescent dye master mix (Roche), 2 µl of 25 mM MgCl2, 0.5 µl of the primer pair, template and PCR grade water. The samples were loaded into the 384-well microwell plate and subjected to PCR amplification in a real time PCR machine (LightCycler 480, Roche). The thermal cycling reactions consisted of an initial denaturation (3 s at 95° C.). The amplification consisted of denaturation (1 min at 95° C.), annealing (1 min at 60° C.) and extension (1 min at 72° C.). The PCR was immediately followed by high resolution melting curve analysis. The differentiation of the true NDV virus isolates versus the vaccine strains was achieved by using vaccines as positive controls and comparing their melting curve signatures.

NDV Genotype Differentiation by High Resolution Melting (HRM) Curve Analysis

Positive NDV samples were subjected to the HRM assay. The HRM assay was established by using primer sets (SEQ ID NO:17 and SEQ ID NO:18) that amplify the fusion protein gene of NDV. The assay consisted of 10 µl of the highly saturated fluorescent dye master mix (Roche), 2 µl of 25 mM MgCl2, 0.5 µl of the primer pair, template and PCR grade water. The samples were loaded into the 384-well microwell plate and subjected to PCR amplification in a real-time PCR machine (LightCycler 480, Roche). The thermal cycling reactions consisted of an initial denaturation (3 s at 95° C.). The amplification consisted of denaturation (1 min at 95° C.), annealing (1 min at 60° C.) and extension (1 min at 72° C.). The PCR was immediately followed by high resolution melting curve analysis. The differentiation of the NDV genotypes was achieved by using known positive NDV genotypes as positive controls and comparing their melting curve signatures. Confirmation of the assay was done by sequencing the positive NDV isolates.

Validation

A typical validation based on ISO 17025 and MIQE (Minimum Information for Publication of Quantitative Real-Time PCR Experiments has 8 parameters (Analytical sensitivity, specificity, repeatability, recovery, reproducibility, ruggedness/robustness and purity/concentration) that should be tested. Upon completion of the development of the assays, a simple validation of the protocols was carried out to distinguish its analytical sensitivity, specificity and confirmation by sequencing and amino acid sequence analysis.

Analytical Sensitivity

The aim of the study is to determine the limit of detection (LOD)/lowest concentration of the target agent of interest that can be detected. All concentration of reference materials were measured by using a UV Spectrophotometer. Concentrations were standardized to 10 pg/µl. An end-point dilution (ten-fold serial dilution) was used until the assay could no longer detect the target organism (no detection signals).

Specificity

The aim of the study is to assess the specificity of the assay to detect the target agent of interest in the presence of other infectious agents. The specificity of the test was conducted by testing the protocol against 5 other organisms (Infectious Bronchitis Virus, Infectious Bursal Disease Virus, *Mycoplasma synoviae*, *Mycoplasma gallisepticum*, Avian pneumovirus). To pass this parameter, the assay should not produce the same detection signals (melting peaks) or should not produce any detection signals for other organisms. The method should be specific enough to detect only the target agent of interest even in the presence of other flora.

Sequencing and Amino Acid Sequence Analysis.

The parameter was conducted as described above.

Results

Sampling

Samples from all 14 farms were found to be positive for NDV.

Sequencing, Amino Acid Sequence Analysis, Phylogenetic Construction

BLAST analysis showed that all sequences samples were true NDV cases when compared with other sequences in Genbank. Amino acid sequence analysis of the fusion (F) gene of fourteen Malaysian NDV isolates showed that eleven (11) of the isolates were categorized as velogenic virus and three (3) were lentogenic. The 11 velogenic strains had the F cleavage site motif 112R-R-R-K-R-F117 (SEQ ID NO:33) while 2 of the lentogenic strains had the F cleavage site motif 112G-R-Q-G-R-L117 (SEQ ID NO:34), whilst 1 sequence had the F cleavage site motif 112G-K-Q-G-R-L117 (SEQ ID NO:35) at the C-terminus of the F2 protein and phenylalanine (F) residue at amino acid position 117 of the N-terminus of the F1 protein (Berhanu et al., Virol J., 7:183, 2010). Phylogenetic analysis revealed that 11 of the Malaysian isolates clustered tightly with the genotype VIId strains, 1 Malaysian isolate grouped together with genotype I and 2 of our isolates grouped with genotype II. Of the 11 Malaysian isolates that grouped to form genotype VIId, 10 (F1, F2, F3, F4, F9, F10, F11, F12, F13, F14) had between 97.9 to 98.7% sequence identity similarities with other Malaysian isolates responsible for the Newcastle disease outbreaks in 2004-2005 and 2007 which were previously reported by researchers from UPM. All these isolates have between 91-92% similarities with the Indonesian strain (cockatoo/14698/90). One (F8) of the Malaysian isolate which grouped with genotype VIId had 96.1% similarities with the China strain (Ch/2000). Of the 3 lentogenic strain isolates from this study, two (F5, F6) had between 97.4-97.5% nucleotide sequence similarities with strain Lasota, genotype 2 while one isolate (F7) had around 88.8% nucleotide sequence similarities with strain Ulster/67.

DIVA (Differentiation of Infected Versus Vaccine) Assay

DIVA assay for all the positive Malaysian isolates showed that they had no relationship with the Avinew or Lasota (FIG. 24). The assay was analyzed by using the Gene Scanning software supplied with the instrument. The clustering algorithm of the software allows all melting curves to be normalized and it subsequently clusters all samples and data that have the same melting signatures.

NDV Genotype Differentiation by High Resolution Melting (HRM) Curve Analysis

The HRM assay to distinguish the NDV genotypes correlated with the gene scanning analysis and amino acid sequence analysis (FIG. 25). Similar to the DIVA assay described above, the same Gene Scanning software from Roche was used for analyzing the data. Amino acid sequence analysis of the fusion (F) gene of fourteen Malaysian NDV isolates showed that eleven (11) of the isolates were categorized as velogenic virus and three (3) was lentogenic. The 11 velogenic strain had the F cleavage site motif 112 R-R-R-K-R-F 117 (SEQ ID NO:33) while 2 of the lentogenic strain had the F cleavage site motif 112 G-R-Q-G-R-L 117 (SEQ ID NO:34) and 1 sequence had the F cleavage site motif 112 G-K-Q-G-R-L 117 (SEQ ID NO:35) at the C-terminus of the F2 protein and phenylalanine (F) residue at amino acid position 117 of the N-terminus of the F1 protein. This confirms that the HRM assay is fit for its intended use.

Validation

The assay could detect as low as 0.05 ag for a total reaction volume of 20 μl. The primers were specific for NDV F gene and had no relationship with other organisms as stated in the methodology.

Analysis of More NDV Vaccines Using HRM

More NDV vaccine strains were analysed by HRM. These vaccines include: Avinew (Merial Limited), Clone 30 (Intervet), KBNP—Dalguban (KBNP, Korea), ND-B1 (Merial Limited), and Mukteswar (Malaysian Vaccine Pharmaceuticals).

The assay consisted of 1 μl of the highly saturated fluorescent dye master mix, 2 μl of 25 mM MgCl2, 12.5 μl of HRM mastermix, 1 μl of the primer pair (SEQ ID NO:31 and 32), template and PCR grade water. The samples were loaded into the 384-well microwell plate and subjected to PCR amplification in a real time PCR machine (LightCycler 480, Roche). The thermal cycling reactions consisted of an initial denaturation (3 sec at 95° C.). The amplification consisted of denaturation (1 min at 95° C.), annealing (1 min at 56° C.) and extension (1 min at 72° C.). The PCR was immediately followed by high resolution melting curve analysis.

Figure 20:
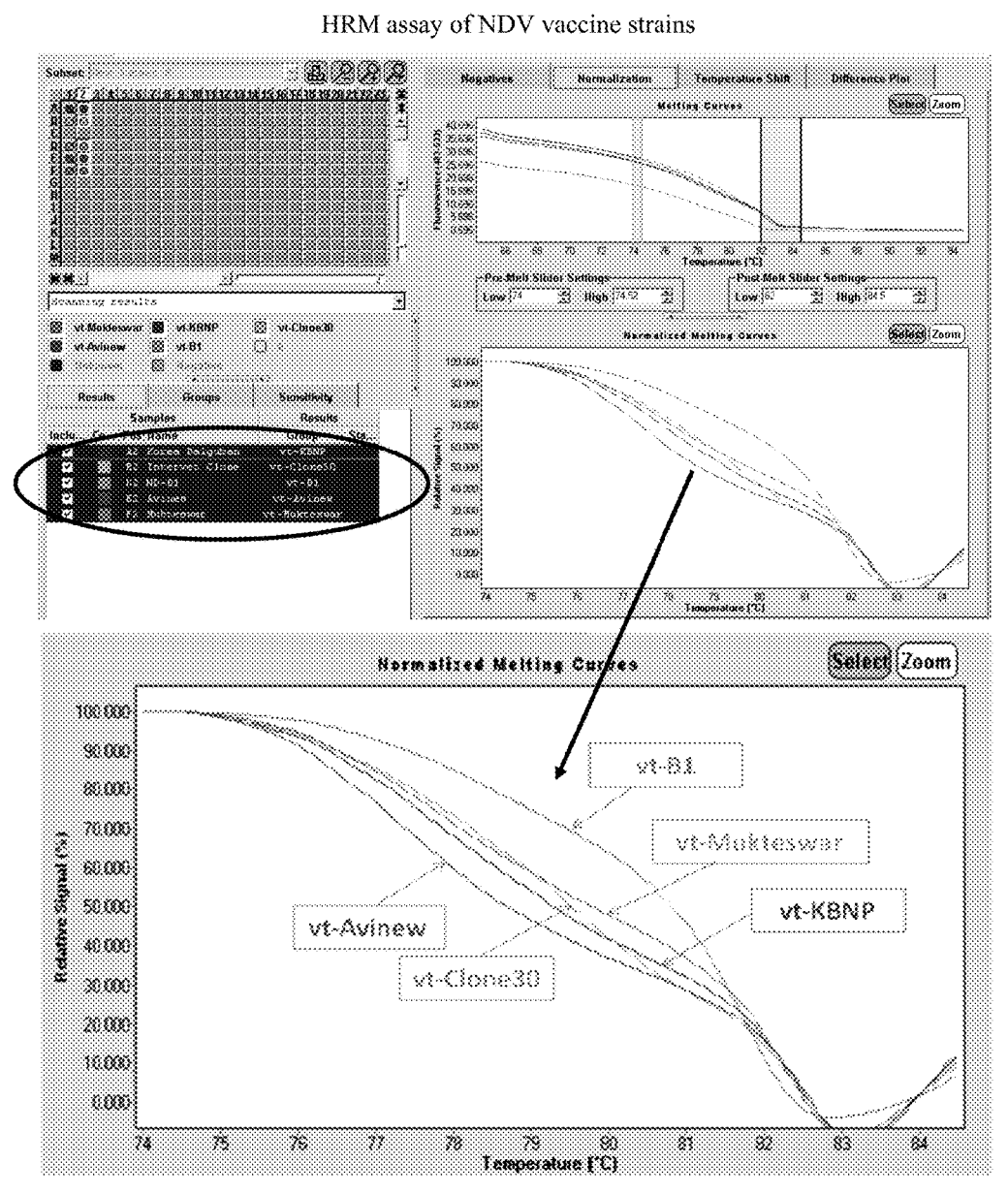
Figure 21A:
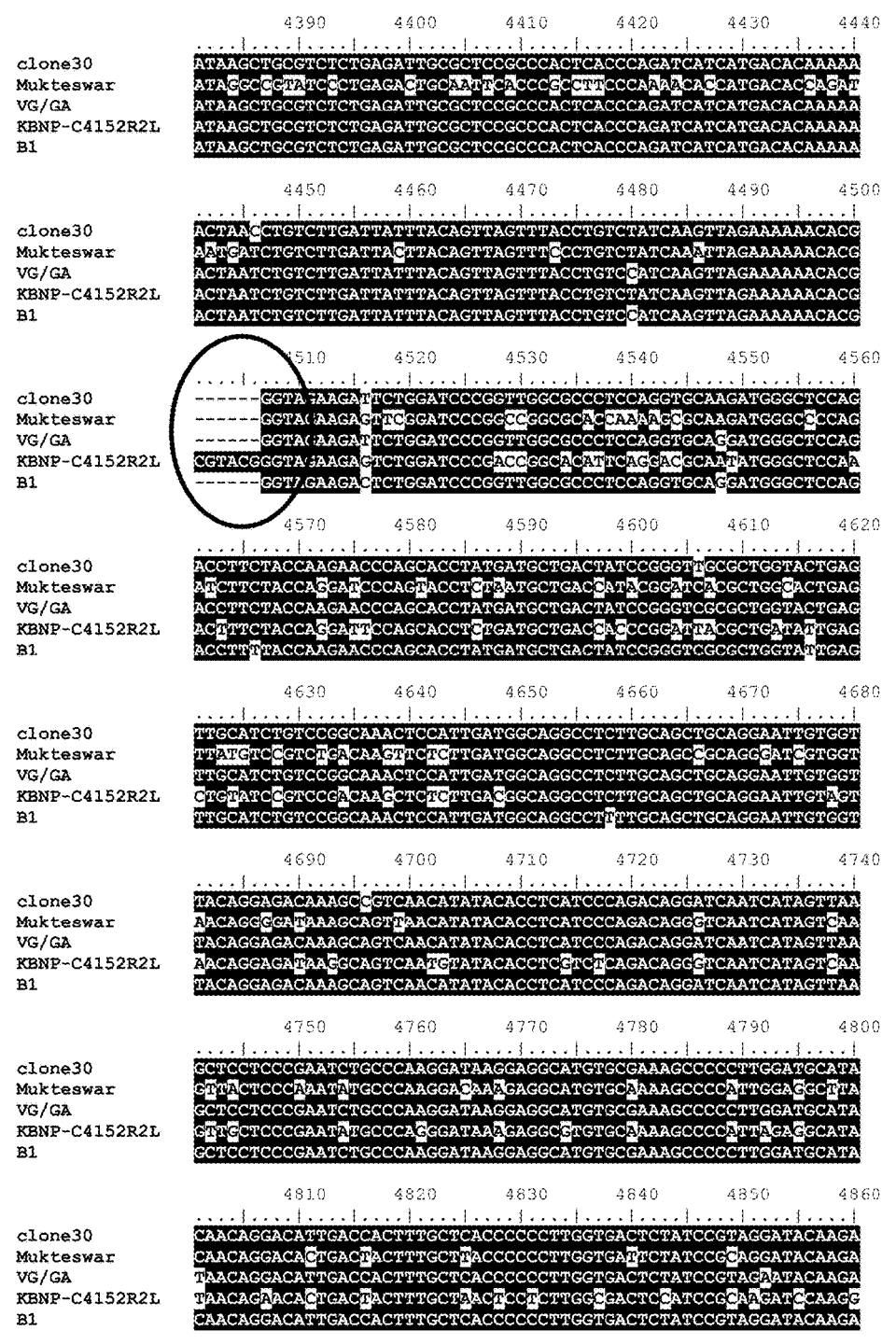

The HRM assay was able to differentiate the vaccine-types tested (FIG. 20). A portion of the nucleotide sequence alignment of the whole genome of the five vaccine-type strains of NDV is shown in FIG. 21. Various nucleotide differences can be observed throughout the genome of the viruses which account for the distinction of the melting curves. Multiple alignment of the amino acid sequence of the fusion protein gene of the five vaccine-type strains of NDV is shown in FIG. 22. Similarly various differences could be observed at various sites.

The sequence identity matrix of the whole genome of the vaccine-type NDV and the sequence identity matrix of the amino acids for the fusion (F) protein of the vaccine-type NDV are depicted in FIGS. 23A-23B.

The results showed that the HRM (high resolution melt) analysis could distinctly separate the melting curves into exclusive groups for each vaccine-type. Multiple alignments of the sequences of the whole genome and amino acid of the fusion protein gene of the five vaccine-types showed various nucleotide variations at multiple sites throughout the whole genome. Of the five studies, the KBNP-vaccine type showed six nucleotide insertions "CGTACG" at nucleotide position 4500 to 4506. None of the other vaccines tested had this sequence. It is reported that KBNP is a recombinant La Sota strain (KBNP-C4152R2L) in which fusion (F) and hemagglutinin-neuraminidase (HN) genes were replaced with the F and FIN gene from genotype VIId virus by mutating the F cleavage motif from $^{112}$RRQKR$^{116}$ (SEQ ID NO:45) to $^{112}$GRQAR$^{116}$ (SEQ ID NO:46) (FIG. 22). The six nucleotide sequence was inserted into the intergenic region between the matrix protein and F genes for attenuation without breaking the "rule of six" as a marker (Cho et al., Clinical and Vaccine Immunology, 15(10):1572-9, 2008). This serves as a good marker for differentiating the KBNP vaccine with Avinew. Similarly, the other vaccines have nucleotide differences at various sites making it possible to differentiate the vaccine-types by HRM.

Scoring of the sequences by identity matrices tool for the whole virus genome showed 99% similarity between Avinew and ND Clone 30 (Intervet), 87.7% between Avinew and Mukteswar (MVP), 94.9% between Avinew and KBNP (Korea Dalguban) and 99.5% between Avinew and ND-B1 (Merial).

Scoring of the amino acid sequence by identity matrices tool for the fusion protein gene of the vaccine-types showed 99% similarity between Avinew and ND Clone 30 (Intervet), 88.9% between Avinew and Mukteswar (MVP), 88.6% between Avinew and KBNP (Korea Dalguban) and 99% between Avinew and ND-B1 (Merial).

The scoring matrices suggest that the dissimilarity between the NDV viruses are varying at 12.7% between Avinew and Mukteswar (MVP) based on nucleotide dissimilarity and 11.4% between Avinew and KBNP (Korea Dalguban) and 11.1% between Avinew and Mukteswar (MVP) based on amino acid sequence dissimilarity of its fusion protein gene.

Validations were carried to assess the assay and the assay was found to fit for its intended use in terms of sensitivity and specificity.

The results further demonstrated that the HRM assay was able to generate unique melting profiles to distinctly identify each vaccine-type.

What we claim is:

1. A method of characterizing one or more Newcastle Disease Virus (NDV) strains isolated from one or more animals comprising the steps of:

a) generating an NDV cDNA from the NDV strains isolated from the animals;

b) exposing the cDNA to a primer pair comprising a forward primer and a reverse primer in a real-time polymerase chain reaction (PCR) to yield an amplicon, wherein the primer pair is specific to the F or M gene of NDV genome, and wherein the real-time PCR comprises the steps of:

i) initial denaturation at 95° C. for 3 seconds;

ii) denaturation at 95° C. for 1 minute;

iii) annealing at 60° C. for 1 minute;

iv) extension at 72° C. for 1 minute;

v) repeating steps ii)-iv) 45 times;

c) performing high resolution melt (HRM) curve analysis on a double-stranded product comprising the amplicon immediately after the real-time PCR; and d) analyzing the HRM curve thereby characterizing the NDV strain, wherein the primer pair comprises a forward primer having the sequence as set forth in SEQ ID NO:17 and a reverse primer having the sequence as set forth in SEQ ID NO:18, or a forward primer having the sequence as set forth in SEQ ID NO:31 and a reverse primer having the sequence as set forth in SEQ ID NO:32;

wherein a saturating dye suitable for HRM is used.

2. The method of claim 1, wherein the one or more NDV strains are selected from the group consisting of, Avinew strain, LaSota strain, MVP-Mukteswar strain, ND-B1 strain, Korea Dalguban strain, Herts 33 strain, Essex'70 strain, 135/93 strain, 617/83 strain, 34/90 strain, Beaudette C strain, D26 strain, MC110 strain, and 1154/98 strain.

3. The method of claim 1 further comprising the steps of sequencing the amplicon and identifying a novel strain of NDV wherein the F or M sequence of the NDV strain has less than 95% sequence identity to known NDV F or M sequences.

4. The method of claim 3 further comprising the step of isolating the novel strain of NDV.

5. The method of claim 1, wherein the process further comprises the step of identifying whether the NDV strain is a vaccine-type strain or a wild-type strain that infected the animals.

* * * * *